(12) United States Patent
Cardon et al.

(10) Patent No.: US 12,193,939 B2
(45) Date of Patent: Jan. 14, 2025

(54) PATIENT SPECIFIC HUMERAL IMPLANT COMPONENTS

(71) Applicant: HOWMEDICA OSTEONICS CORP., Mahwah, NJ (US)

(72) Inventors: Jean-Emmanuel Cardon, Domene (FR); Benjamin Dassonville, Saint Hilaire du Touvet (FR); Shawn M. Gargac, Fort Wayne, IN (US); Delphine Claire Michelle Henry, Saint Ismier (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 421 days.

(21) Appl. No.: 16/910,663

(22) Filed: Jun. 24, 2020

(65) Prior Publication Data

US 2020/0383792 A1 Dec. 10, 2020

Related U.S. Application Data

(63) Continuation of application No. PCT/US2018/068006, filed on Dec. 28, 2018.

(60) Provisional application No. 62/612,201, filed on Dec. 29, 2017.

(51) Int. Cl.
*A61F 2/40* (2006.01)
*A61F 2/30* (2006.01)

(52) U.S. Cl.
CPC .............. *A61F 2/30942* (2013.01); *A61F 2002/30476* (2013.01); *A61F 2002/30593* (2013.01); *A61F 2002/30616* (2013.01); *A61F 2002/30952* (2013.01); *A61F 2002/30985* (2013.01); *A61F 2002/4022* (2013.01); *A61F 2002/4062* (2013.01); *A61F 2002/4077* (2013.01)

(58) Field of Classification Search
CPC ........ A61F 2/30942; A61F 2002/30476; A61F 2002/30985; A61F 2002/30952; A61F 2002/4022; A61F 2002/4062
See application file for complete search history.

(56) References Cited

U.S. PATENT DOCUMENTS

| 3,314,420 | A | 4/1967 | Smith et al. |
| D243,286 | S | 2/1977 | Deyerle |
| 4,919,670 | A | 4/1990 | Dale et al. |

(Continued)

FOREIGN PATENT DOCUMENTS

| CA | 2927086 | 4/2015 |
| CA | 2927811 | 4/2015 |

(Continued)

OTHER PUBLICATIONS

US 9,451,972 B2, 09/2016, Lang et al. (withdrawn)

(Continued)

*Primary Examiner* — Alvin J Stewart
(74) *Attorney, Agent, or Firm* — DUANE MORRIS LLP

(57) ABSTRACT

In one embodiment, a humeral implant is provided that includes a hollow stem and a mounting end. The hollow stem has a sharp distal edge. The mounting end has a mounting hole and a mounting channel disposed about the mounting hole. The mounting hole is configured to receive a tapered projection of an anatomic articular body. The mounting channel is configured to receive an annular projection of a reverse articular body.

8 Claims, 38 Drawing Sheets

(56) References Cited

U.S. PATENT DOCUMENTS

| | | | |
|---|---|---|---|
| 5,030,219 A | 7/1991 | Matsen, III et al. | |
| 5,329,846 A | 7/1994 | Bonutti | |
| 5,383,938 A | 1/1995 | Rohr et al. | |
| 5,458,637 A | 10/1995 | Hayes | |
| 5,531,793 A | 7/1996 | Kelman et al. | |
| 5,610,966 A | 3/1997 | Martell et al. | |
| 5,665,118 A | 9/1997 | LaSalle et al. | |
| 5,725,586 A | 3/1998 | Sommerich | |
| 5,768,134 A | 6/1998 | Swaelens et al. | |
| 5,769,856 A | 6/1998 | Dong et al. | |
| 5,779,710 A | 7/1998 | Matsen, III | |
| 5,800,555 A | 9/1998 | Gray | |
| 5,807,437 A | 9/1998 | Sachs et al. | |
| 5,824,078 A | 10/1998 | Nelson et al. | |
| 5,824,085 A | 10/1998 | Sahay et al. | |
| 6,002,859 A | 12/1999 | DiGioia, III et al. | |
| 6,102,953 A | 8/2000 | Huebner | |
| 6,129,764 A | 10/2000 | Servidio | |
| 6,155,812 A | 12/2000 | Smith et al. | |
| 6,162,226 A | 12/2000 | DeCarlo, Jr. et al. | |
| 6,172,856 B1 | 1/2001 | Jang | |
| 6,183,519 B1 | 2/2001 | Bonnin et al. | |
| D440,630 S | 4/2001 | Gottwald | |
| 6,277,121 B1 | 8/2001 | Burkinshaw et al. | |
| 6,364,910 B1 | 4/2002 | Shultz et al. | |
| 6,385,475 B1 | 5/2002 | Cinquin et al. | |
| 6,432,142 B1 | 8/2002 | Kamiya et al. | |
| 6,459,948 B1 | 10/2002 | Ateshian et al. | |
| 6,530,957 B1 | 3/2003 | Jack | |
| 6,648,894 B2 | 11/2003 | Abdelgany et al. | |
| 6,679,916 B1 | 1/2004 | Frankle et al. | |
| 6,719,799 B1 * | 4/2004 | Kropf | A61F 2/4014 623/19.12 |
| 6,772,026 B2 | 8/2004 | Bradbury et al. | |
| 6,797,006 B2 | 9/2004 | Hodorek | |
| 6,849,223 B2 | 2/2005 | Dean et al. | |
| 6,915,150 B2 | 7/2005 | Cinquin et al. | |
| 6,944,518 B2 | 9/2005 | Roose | |
| 6,989,034 B2 | 1/2006 | Hammer | |
| 7,175,665 B2 | 2/2007 | German et al. | |
| 7,468,075 B2 | 12/2008 | Lang et al. | |
| 7,469,474 B2 | 12/2008 | Farrar | |
| 7,534,263 B2 | 5/2009 | Burdulis, Jr. et al. | |
| 7,599,539 B2 | 10/2009 | Kunz et al. | |
| 7,618,451 B2 | 11/2009 | Berez et al. | |
| 7,634,119 B2 | 12/2009 | Tsougarakis et al. | |
| 7,648,530 B2 | 1/2010 | Habermeyer et al. | |
| 7,678,150 B2 * | 3/2010 | Tornier | A61F 2/40 623/19.13 |
| 7,702,380 B1 | 4/2010 | Dean | |
| 7,717,956 B2 | 5/2010 | Lang | |
| 7,747,305 B2 | 6/2010 | Dean et al. | |
| 7,796,791 B2 | 9/2010 | Tsougarakis et al. | |
| 7,799,077 B2 | 9/2010 | Lang et al. | |
| 7,802,503 B2 | 9/2010 | Couvillion et al. | |
| 7,822,588 B2 | 10/2010 | Mueller et al. | |
| 7,831,079 B2 | 11/2010 | Kunz et al. | |
| 7,892,287 B2 | 2/2011 | Deffenbaugh | |
| 7,927,338 B2 | 4/2011 | Laffargue et al. | |
| 7,981,158 B2 | 7/2011 | Fitz et al. | |
| 7,983,777 B2 | 7/2011 | Melton et al. | |
| 7,993,408 B2 | 8/2011 | Meridew et al. | |
| 8,007,448 B2 | 8/2011 | Barrera | |
| 8,014,984 B2 | 9/2011 | Iannotti et al. | |
| 8,055,487 B2 | 11/2011 | James | |
| 8,062,302 B2 | 11/2011 | Lang et al. | |
| 8,066,708 B2 | 11/2011 | Lang et al. | |
| 8,077,950 B2 | 12/2011 | Tsougarakis et al. | |
| 8,083,745 B2 | 12/2011 | Lang et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,234,097 B2 | 7/2012 | Steines et al. | |
| 8,337,501 B2 | 12/2012 | Fitz et al. | |
| 8,337,503 B2 | 12/2012 | Lian | |
| 8,337,507 B2 | 12/2012 | Lang et al. | |
| 8,343,218 B2 | 1/2013 | Lang et al. | |
| 8,350,186 B2 | 1/2013 | Jones et al. | |
| 8,366,771 B2 | 2/2013 | Burdulis, Jr. et al. | |
| 8,377,073 B2 | 2/2013 | Wasielewski | |
| 8,377,129 B2 | 2/2013 | Fitz et al. | |
| 8,439,926 B2 | 5/2013 | Bojarski et al. | |
| 8,457,930 B2 | 6/2013 | Schroeder | |
| 8,460,304 B2 | 6/2013 | Fitz et al. | |
| 8,475,463 B2 | 7/2013 | Lian | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski et al. | |
| 8,532,806 B1 | 9/2013 | Masson | |
| 8,535,319 B2 | 9/2013 | Ball | |
| 8,545,509 B2 | 10/2013 | Park et al. | |
| 8,545,569 B2 | 10/2013 | Fitz et al. | |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,579,984 B2 | 11/2013 | Borowsky | |
| 8,585,708 B2 | 11/2013 | Fitz et al. | |
| 8,608,749 B2 | 12/2013 | Meridew et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,663,333 B2 * | 3/2014 | Metcalfe | A61F 2/4059 623/19.14 |
| 8,682,052 B2 | 3/2014 | Fitz et al. | |
| 8,690,945 B2 | 4/2014 | Fitz et al. | |
| 8,709,089 B2 | 4/2014 | Lang et al. | |
| 8,731,885 B2 | 5/2014 | Iannotti et al. | |
| 8,735,773 B2 | 5/2014 | Lang | |
| 8,744,148 B2 | 6/2014 | Nord et al. | |
| 8,768,028 B2 | 7/2014 | Lang et al. | |
| 8,771,365 B2 | 7/2014 | Bojarski et al. | |
| 8,774,900 B2 | 7/2014 | Buly et al. | |
| 8,775,133 B2 | 7/2014 | Schroeder | |
| 8,781,557 B2 | 7/2014 | Dean et al. | |
| 8,814,942 B2 | 8/2014 | Anthony et al. | |
| 8,843,229 B2 | 9/2014 | Vanasse et al. | |
| 8,864,769 B2 | 10/2014 | Stone et al. | |
| 8,882,847 B2 | 11/2014 | Burdulis, Jr. et al. | |
| 8,884,618 B2 | 11/2014 | Mahfouz | |
| 8,888,855 B2 * | 11/2014 | Roche | A61F 2/40 623/19.12 |
| 8,898,043 B2 | 11/2014 | Ashby et al. | |
| 8,906,102 B2 | 12/2014 | Viscardi et al. | |
| 8,906,107 B2 | 12/2014 | Bojarski et al. | |
| 8,926,706 B2 | 1/2015 | Bojarski et al. | |
| 8,932,361 B2 | 1/2015 | Tornier et al. | |
| 8,932,363 B2 | 1/2015 | Tsougarakis et al. | |
| 8,934,961 B2 | 1/2015 | Lakin et al. | |
| 8,945,230 B2 | 2/2015 | Lang et al. | |
| 8,951,259 B2 | 2/2015 | Fitz et al. | |
| 8,951,260 B2 | 2/2015 | Lang et al. | |
| 8,965,088 B2 | 2/2015 | Tsougarakis et al. | |
| 8,971,606 B2 | 3/2015 | Chaoui | |
| 8,974,539 B2 | 3/2015 | Bojarski et al. | |
| 8,984,731 B2 | 3/2015 | Broeck et al. | |
| 8,989,460 B2 | 3/2015 | Mahfouz | |
| 8,992,538 B2 | 3/2015 | Keefer | |
| 8,998,915 B2 | 4/2015 | Fitz et al. | |
| 9,020,788 B2 | 4/2015 | Lang | |

(56) References Cited

U.S. PATENT DOCUMENTS

| | | |
|---|---|---|
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| D744,612 S | 12/2015 | Peterson et al. |
| 9,208,558 B2 | 12/2015 | Dean et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,275,191 B2 | 3/2016 | Dean et al. |
| 9,278,413 B2 | 3/2016 | Sperling |
| 9,292,920 B2 | 3/2016 | Dean et al. |
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| D757,252 S | 5/2016 | Von Moger et al. |
| 9,326,780 B2 | 5/2016 | Wong et al. |
| 9,326,862 B2 * | 5/2016 | Smith .................. A61F 2/40 |
| 9,330,206 B2 | 5/2016 | Dean et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,498,344 B2 * | 11/2016 | Hodorek ................ A61B 17/17 |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,615,839 B2 | 4/2017 | Olson |
| 9,626,756 B2 | 4/2017 | Dean et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,672,302 B2 | 6/2017 | Dean et al. |
| 9,672,617 B2 | 6/2017 | Dean et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,313 B1 | 8/2017 | Sohn et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,068,671 B2 | 9/2018 | Dean et al. |
| 10,085,839 B2 | 10/2018 | Wong et al. |
| 10,143,558 B2 * | 12/2018 | Frankle ................ A61F 2/4014 |
| 10,405,993 B2 | 9/2019 | Deransart et al. |
| 10,433,969 B2 * | 10/2019 | Humphrey .......... A61F 2/30771 |
| 10,537,390 B2 * | 1/2020 | Varadarajan ......... A61B 34/10 |
| 10,548,737 B2 * | 2/2020 | Hodorek .............. A61F 2/4612 |
| 10,716,676 B2 | 7/2020 | Tornier et al. |
| D938,590 S | 12/2021 | Wolfe et al. |
| 11,229,522 B2 | 1/2022 | Nerot et al. |
| 11,364,127 B2 * | 6/2022 | Deransart ............. A61F 2/4014 |
| 2001/0041940 A1 | 11/2001 | Pearl |
| 2001/0047210 A1 | 11/2001 | Wolf |
| 2002/0007294 A1 | 1/2002 | Bradbury et al. |
| 2002/0025358 A1 | 2/2002 | Nelson et al. |
| 2002/0082741 A1 | 6/2002 | Mazumder et al. |
| 2002/0151982 A1 | 10/2002 | Masini |
| 2003/0028253 A1 * | 2/2003 | Stone .................... A61F 2/4014 |
| | | 623/19.14 |
| 2003/0074080 A1 * | 4/2003 | Murray ................ A61F 2/4637 |
| | | 623/23.23 |
| 2003/0139818 A1 | 7/2003 | Rogers et al. |
| 2004/0002765 A1 | 1/2004 | Maroney et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0153161 A1 | 8/2004 | Stone et al. |
| 2004/0171924 A1 | 9/2004 | Mire et al. |
| 2004/0181144 A1 | 9/2004 | Cinquin et al. |
| 2004/0199258 A1 | 10/2004 | Macara |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0098915 A1 | 5/2005 | Long et al. |
| 2005/0112397 A1 | 5/2005 | Rolfe et al. |
| 2005/0197814 A1 | 9/2005 | Aram |
| 2005/0216305 A1 | 9/2005 | Funderud |
| 2006/0074353 A1 | 4/2006 | Deffenbaugh et al. |
| 2006/0074430 A1 | 4/2006 | Deffenbaugh et al. |
| 2006/0100714 A1 | 5/2006 | Ensign |
| 2006/0136058 A1 | 6/2006 | Pietrzak |
| 2006/0161167 A1 | 7/2006 | Myers et al. |
| 2006/0276905 A1 | 12/2006 | Calamel |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0173945 A1 * | 7/2007 | Wiley ................ A61F 2/30734 |
| | | 623/19.13 |
| 2007/0191741 A1 | 8/2007 | Tsai et al. |
| 2007/0198094 A1 * | 8/2007 | Berelsman ............ A61F 2/4014 |
| | | 623/22.42 |
| 2007/0244562 A1 | 10/2007 | Roche et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0010900 A1 | 5/2008 | Maroney et al. |
| 2008/0109000 A1 | 5/2008 | Maroney et al. |
| 2008/0140209 A1 | 6/2008 | Iannotti et al. |
| 2008/0183297 A1 | 7/2008 | Boileau et al. |

(56) References Cited

U.S. PATENT DOCUMENTS

| | | |
|---|---|---|
| 2008/0228269 A1 | 9/2008 | McLeod et al. |
| 2008/0243127 A1 | 10/2008 | Lang et al. |
| 2009/0099662 A1* | 4/2009 | Splieth .................. A61F 2/4684 |
| | | 623/19.12 |
| 2009/0182336 A1 | 7/2009 | Brenzel et al. |
| 2009/0204225 A1 | 8/2009 | Meridew et al. |
| 2009/0210065 A1 | 8/2009 | Nerot et al. |
| 2009/0226068 A1 | 9/2009 | Fitz et al. |
| 2009/0254091 A1 | 10/2009 | Long et al. |
| 2009/0264894 A1 | 10/2009 | Wasielewski |
| 2009/0270863 A1 | 10/2009 | Maisonneuve |
| 2009/0270865 A1 | 10/2009 | Poncet et al. |
| 2009/0292464 A1 | 11/2009 | Fuchs et al. |
| 2010/0076572 A1 | 3/2010 | Jamali |
| 2010/0082035 A1 | 4/2010 | Keefer |
| 2010/0087927 A1* | 4/2010 | Roche ...................... A61F 2/40 |
| | | 606/86 R |
| 2010/0094292 A1 | 4/2010 | Parrott |
| 2010/0114326 A1 | 5/2010 | Winslow et al. |
| 2010/0125336 A1 | 5/2010 | Johnson et al. |
| 2010/0161066 A1 | 6/2010 | Iannotti et al. |
| 2010/0191100 A1 | 7/2010 | Anderson et al. |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0035013 A1 | 2/2011 | Winslow et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0118846 A1* | 5/2011 | Katrana ................ A61F 2/4059 |
| | | 623/19.13 |
| 2011/0119884 A1 | 5/2011 | Ratron |
| 2011/0137424 A1 | 6/2011 | Lappin et al. |
| 2011/0144760 A1 | 6/2011 | Wong et al. |
| 2011/0213372 A1 | 9/2011 | Keefer et al. |
| 2011/0282403 A1 | 11/2011 | Anthony et al. |
| 2012/0010711 A1 | 1/2012 | Antonyshyn et al. |
| 2012/0078258 A1 | 3/2012 | Lo et al. |
| 2012/0116203 A1 | 5/2012 | Vancraen et al. |
| 2012/0123419 A1 | 5/2012 | Purdy et al. |
| 2012/0130434 A1 | 5/2012 | Stemniski |
| 2012/0141034 A1 | 6/2012 | Iannotti et al. |
| 2012/0143267 A1 | 6/2012 | Iannotti et al. |
| 2012/0197258 A1 | 8/2012 | Chavarria et al. |
| 2012/0209394 A1 | 8/2012 | Bojarski et al. |
| 2012/0221112 A1 | 8/2012 | Lappin |
| 2012/0232670 A1 | 9/2012 | Bojarski et al. |
| 2012/0245646 A1 | 9/2012 | Gustilo et al. |
| 2012/0253350 A1 | 10/2012 | Anthony et al. |
| 2012/0253467 A1* | 10/2012 | Frankle ................ A61F 2/4014 |
| | | 623/19.11 |
| 2012/0276509 A1 | 11/2012 | Iannotti et al. |
| 2012/0279933 A1 | 11/2012 | Hensler et al. |
| 2012/0290272 A1 | 11/2012 | Bryan |
| 2012/0296339 A1 | 11/2012 | Iannotti et al. |
| 2013/0006369 A1 | 1/2013 | Wiley et al. |
| 2013/0053968 A1 | 2/2013 | Nardini et al. |
| 2013/0110116 A1 | 5/2013 | Kehres et al. |
| 2013/0110470 A1 | 5/2013 | Vanasse et al. |
| 2013/0110471 A1 | 5/2013 | Lang et al. |
| 2013/0114873 A1 | 5/2013 | Chaoui |
| 2013/0145609 A1 | 6/2013 | Sperling |
| 2013/0150858 A1 | 6/2013 | Primiano et al. |
| 2013/0150975 A1 | 6/2013 | Iannotti et al. |
| 2013/0172898 A1 | 7/2013 | Iannotti et al. |
| 2013/0190882 A1 | 7/2013 | Humphrey |
| 2013/0204375 A1* | 8/2013 | Winslow ................ A61F 2/4014 |
| | | 623/19.13 |
| 2013/0211531 A1 | 8/2013 | Steines et al. |
| 2013/0245631 A1 | 9/2013 | Bettenga |
| 2013/0261629 A1 | 10/2013 | Anthony et al. |
| 2013/0274752 A1 | 10/2013 | Trouilloud et al. |
| 2013/0325134 A1* | 12/2013 | Viscardi ................ A61F 2/4684 |
| | | 623/19.14 |
| 2013/0338673 A1 | 12/2013 | Keppler |
| 2014/0039633 A1 | 2/2014 | Roche et al. |
| 2014/0074246 A1* | 3/2014 | Huebner ................ A61F 2/3804 |
| | | 623/20.11 |
| 2014/0159282 A1 | 6/2014 | Smith et al. |
| 2014/0236304 A1* | 8/2014 | Hodorek .................. A61F 2/40 |
| | | 623/19.14 |
| 2014/0257304 A1 | 9/2014 | Eash |
| 2014/0257499 A1 | 9/2014 | Winslow et al. |
| 2014/0276867 A1 | 9/2014 | Kelley et al. |
| 2014/0371863 A1 | 12/2014 | Vanasse et al. |
| 2015/0045802 A1 | 2/2015 | Kelley |
| 2015/0045903 A1 | 2/2015 | Neal |
| 2015/0054195 A1 | 2/2015 | Greyf |
| 2015/0093283 A1 | 4/2015 | Miller et al. |
| 2015/0150688 A1 | 6/2015 | Vanasse et al. |
| 2015/0202045 A1 | 7/2015 | Early et al. |
| 2015/0223941 A1 | 8/2015 | Lang |
| 2015/0250552 A1 | 9/2015 | Radermacher et al. |
| 2015/0250597 A1 | 9/2015 | Lang et al. |
| 2015/0250601 A1 | 9/2015 | Humphrey |
| 2015/0265411 A1* | 9/2015 | Deransart ............. A61F 2/4014 |
| | | 623/19.14 |
| 2015/0320430 A1 | 11/2015 | Kehres et al. |
| 2015/0328004 A1 | 11/2015 | Mafhouz |
| 2016/0015466 A1 | 1/2016 | Park et al. |
| 2016/0030196 A1 | 2/2016 | Eraly et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0136904 A1 | 5/2016 | Murai et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0249939 A1 | 9/2016 | Richter et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0310285 A1 | 10/2016 | Kovacs et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0374697 A1 | 12/2016 | Kehres et al. |
| 2017/0000614 A1 | 1/2017 | Mahfouz |
| 2017/0000615 A1 | 1/2017 | Mahfouz |
| 2017/0007330 A1* | 1/2017 | Britton ................ A61B 5/4528 |
| 2017/0027587 A1 | 2/2017 | Fraone et al. |
| 2017/0027593 A1 | 2/2017 | Bojarski et al. |
| 2017/0027702 A1 | 2/2017 | Goldstein et al. |
| 2017/0056024 A1 | 3/2017 | Chao |
| 2017/0056187 A1* | 3/2017 | Humphrey ............ A61F 2/4014 |
| 2017/0071748 A1* | 3/2017 | Humphrey ............ A61F 2/4014 |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0143494 A1 | 5/2017 | Mahfouz |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1* | 10/2017 | Hatzidakis ................ A61F 2/40 |
| 2017/0340449 A1* | 11/2017 | Deransart ............. A61F 2/4014 |
| 2017/0360567 A1 | 12/2017 | Fitz et al. |

(56) References Cited

U.S. PATENT DOCUMENTS

| | | |
|---|---|---|
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0028325 A1 | 2/2018 | Bojarski et al. |
| 2018/0036019 A1 | 2/2018 | Iannotti et al. |
| 2018/0161176 A1 | 6/2018 | Vivanz et al. |
| 2018/0228614 A1 | 8/2018 | Lang et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2018/0289380 A1 | 10/2018 | Mauldin et al. |
| 2019/0015113 A1 | 1/2019 | Morvan |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0038360 A1 | 2/2019 | Chaoui |
| 2019/0175354 A1* | 6/2019 | Knox ................... A61F 2/4014 |
| 2019/0343658 A1 | 11/2019 | Deransart et al. |
| 2020/0188121 A1 | 6/2020 | Boux De Casson et al. |
| 2020/0188123 A1* | 6/2020 | Hodorek ............. A61F 2/30749 |
| 2020/0214845 A1 | 7/2020 | Knox et al. |
| 2020/0289276 A1* | 9/2020 | Lefebvre ............... A61F 2/4059 |
| 2021/0228371 A1* | 7/2021 | Deransart ............. A61F 2/4014 |
| 2021/0228372 A1* | 7/2021 | Knox ................... A61F 2/4059 |
| 2022/0287850 A1* | 9/2022 | Daudet ............... A61F 2/30749 |
| 2022/0354658 A1* | 11/2022 | Knox .................... A61B 17/15 |

FOREIGN PATENT DOCUMENTS

| | | |
|---|---|---|
| CA | 2938709 | 5/2015 |
| CA | 211535 | 5/2022 |
| CA | 211538 | 5/2022 |
| CN | 105213010 A | 1/2016 |
| DE | 10 2006 047663 | 4/2008 |
| EP | 0927548 A2 | 7/1999 |
| EP | 1 249 213 | 10/2002 |
| EP | 1 563 810 | 8/2005 |
| EP | 1265555 | 11/2005 |
| EP | 1 862 151 | 12/2007 |
| EP | 1 902 689 | 3/2008 |
| EP | 1952788 | 8/2008 |
| EP | 2 135 576 | 12/2009 |
| EP | 1 917 051 B1 | 6/2010 |
| EP | 2 243 445 | 10/2010 |
| EP | 2 324 801 A1 | 5/2011 |
| EP | 2 335 655 | 6/2011 |
| EP | 2 501 313 | 9/2012 |
| EP | 2 544 601 | 1/2013 |
| EP | 2583242 | 4/2013 |
| EP | 2 653 136 | 10/2013 |
| EP | 2 845 547 | 3/2015 |
| EP | 2 965 720 | 1/2016 |
| EP | 3057518 | 8/2016 |
| EP | 3057524 | 8/2016 |
| EP | 3065671 | 9/2016 |
| EP | 3068317 | 9/2016 |
| EP | 2 874 570 B1 | 1/2017 |
| EP | 3 117 801 | 1/2017 |
| FR | 2 579 454 | 10/1986 |
| FR | 2 859 099 | 3/2005 |
| FR | 2962573 A1 | 1/2012 |
| FR | 2982694 B1 | 11/2016 |
| FR | 2982979 B1 | 11/2016 |
| FR | 2982693 B1 | 12/2016 |
| GB | 2501494 A | 10/2013 |
| JP | 2012143562 A | 8/2012 |
| JP | 3179628 U | 11/2012 |
| WO | WO 93/025157 | 12/1993 |
| WO | WO 00/35346 | 6/2000 |
| WO | WO 00/59411 | 10/2000 |
| WO | WO 02/061688 | 8/2002 |
| WO | 2006106419 A2 | 10/2006 |
| WO | 2008067400 A2 | 6/2008 |
| WO | WO 2010/120346 | 10/2010 |
| WO | WO 2011/110374 | 9/2011 |
| WO | WO 2011/154891 | 12/2011 |
| WO | WO 2011/157961 | 12/2011 |
| WO | WO 2012/021241 | 2/2012 |
| WO | WO 2012/058349 | 5/2012 |
| WO | WO 2012/125319 | 9/2012 |
| WO | WO 2013/060851 | 5/2013 |
| WO | WO 2013/062848 | 5/2013 |
| WO | WO 2013/062851 | 5/2013 |
| WO | WO 2013/142998 | 10/2013 |
| WO | 2014005644 A1 | 1/2014 |
| WO | WO 2014/020561 | 2/2014 |
| WO | WO 2014/035991 | 3/2014 |
| WO | WO 2014/180972 | 11/2014 |
| WO | WO 2015/052586 | 4/2015 |
| WO | WO 2015/056097 | 4/2015 |
| WO | WO 2015/068035 | 5/2015 |
| WO | WO 2015/071757 | 5/2015 |
| WO | WO 2015/175397 | 11/2015 |
| WO | WO 2015/185219 | 12/2015 |
| WO | WO 2017/005514 | 1/2017 |
| WO | WO 2017/007565 | 1/2017 |
| WO | WO 2017/091657 | 6/2017 |
| WO | WO 2017/105815 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |
| WO | WO 2019/014281 | 1/2019 |
| WO | WO 2019/033037 | 2/2019 |
| WO | WO 2019/060780 | 3/2019 |

OTHER PUBLICATIONS

Communication issued in European Patent Application No. 18837131. 4, Jul. 13, 2022, 6 pages.

Boileau, et al., "The three-dimensional geometry of the proximal humerus: implications for surgical technique and prosthetic design." The Journal of bone and joint surgery. British vol. 79.5 (1997): 857-865.

Dougherty, "Digital Image Processing for Medical Applications," May 11, 2009 (May 11, 2009), Cambridge University Press, XP002615721.

Favre, et al., "Influence of component positioning on impingement in conventional total shoulder arthroplasty," Clinical Biomechanics, Butterworth Scientifics, Nov. 5, 2007, pp. 174-183, vol. 23, No. 2, Guilford, GB.

Gregory, et al.,"Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.

Habets, et al., Computer assistance in orthopaedic surgery. Technische Universiteit Eindhoven, 2002.

Hempfing, et al. "Surgical landmarks to determine humeral head retrotorsion for hemiarthroplasty in fractures." Journal of shoulder and elbow surgery 10.5 (2001): 460-463.

Hernigou, et al., "Determining humeral retroversion with computed tomography." Journal of bone and joint surgery. Oct. 2002;84-A(10):1753-62.

Iannotti et al., "Prosthetic positioning in total shoulder arthroplasty," Journal of Shoulder and Elbow Surgery, Jan. 1, 2005, vol. 14, No. 1S, pp. S111-S121.

Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.

Lee, C.C et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.

Lee, C.C. et al., "Recognizing Abdominal Organs in CT Images Using Contextual Neural Network and Fuzzy Rules", Engineering in Medicine and Biology Society, 2000. Proceedings of the 22nd

(56) References Cited

OTHER PUBLICATIONS

Annual International Conference of the IEEE Jul. 23-28, 2000, Piscataway, NJ, USA, IEEE, vol. 3, Jul. 23, 2000 (Jul. 23, 2000), pp. 1745-1748, XP010530837.
Ma, et al., "Robust registration for computer-integrated orthopedic surgery: laboratory validation and clinical experience." Medical image analysis 7.3 (2003): 237-250.
"Olympia Total Shoulder System Surgical Technique", Wright Medical Technology, 2001, in 19 pages.
Nguyen, et al., "A New Segmentation Method for MRI Images of the Shoulder Joint", Computer and Robot Vision, 2007. CRV '07. Fourth Canadian Conference on, IEEE, PI, May 1, 2007 (May 1, 2007), pp. 329-338, XP031175821.
Radermacher, K., et al., "Computer Assisted Orthopaedic Surgery with Image Based Individual Templates," Clinical Orthopaedics and Related Research, No. 354, Sep. 1998, pp. 28-38.
Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.
Tamez-Pena et al., "The Integration of Automatic Segmentation and Motion Tracking for 4D Reconstruction and Visualization of Musculoskeletal Structures," Biomedical Image Analysis, 1998. Proceedings. Workshop on Santa Barbara, CA US, Jun. 26-27, 1998, Los Alamitos, CA, USA, IEEE Comput. Soc. US, Jun. 26, 1998 (Jun. 26, 1998), pp. 154-163, XP010291418.
Tornier, "Salto Talaris, Total Ankle Prosthesis", 2009.
Valstar, et al. "Towards computer-assisted surgery in shoulder joint replacement." ISPRS journal of photogrammetry and remote sensing 56.5-6 (2002): 326-337.
Valstar, et al. "The use of Roentgen stereophotogrammetry to study micromotion of orthopaedic implants." ISPRS journal of photogrammetry and remote sensing 56.5-6 (2002): 376-389.
Welsh, et al., "CT-based preoperative analysis of scapula morphology and glenohumeral joint geometry." Computer Aided Surgery 8.5 (2003): 264-268.
Wu, et al. "An interface for the data exchange between CAS and CAD/CAM systems." International Congress Series. vol. 1256. Elsevier, 2003.
Zimmer, "Zimmer® PSI Shoulder Trabecular Metal™ Reverse Glenoid Base Plate Surgical Technique", Dec. 30, 2013.
"Zimmer® PSI Shoulder Planning", Zimmer Biomet TV, posted Jul. 11, 2014, retrieved from internet on Jan. 9, 2020, <https://zimmerbiomet.tv/videos/1025?a=surgeon&version=1190>.
International Search Report and Written Opinion issued in PCT Application No. PCT/US2018/068006, dated Apr. 3, 2019, in 18 pages.
1 Final Rejection issued in connection with U.S. Appl. No. 16/717,339, Oct. 13, 202, 28 pages.
Non-Final Office Action issued in connection with U.S. Appl. No. 16/904,345, filed Feb. 15, 2022, 35 pages.
Med Gadget, "Tornier Announces First Implant in U.S. Trial of Its Simpliciti Stemless Shoulder Joint Replacement System", first available Aug. 5, 2011. (https:/Avwww.medgadget.com/2011/08tornier-announces-first-implant-in-u-s-trial-of-its-simpliciti-stemless-shoulder-joint-replacement-system.html) (Year: 2011), 1 page.
Wright Media, "Tornier Aequalis Reversed FX", first available May 19, 2016. (https:/Avww.wrightemedia.com/ProductFiles/Files/PDFs/ CAW-1146_EN_LR_LE.pdf) (Year: 2016), 6 pages.
Arthrex, "Univers Revers Shoulder System", first available Apr. 24, 2019. (https:/Awww.arthrex.com/resources/surgical-technique-guide/ qkv6M00_50qt2QFBx1PKnA/univers-revers-shoulder-system) (Year: 2019).
First Office Action issued in connection with Japanese Patent Application No. 2022-183335, Aug. 15, 2023, 3 pages.
Communication Pursuant to Article 94(3) issued in connection with European Patent Application No. 19759204.1, May 9, 2023, 6 pages.
Communication Pursuant to Article 94(3) issued in connection with European Patent Application No. 18746503.4, Oct. 17, 2023, 5 pages.
International Preliminary Report on Patentability issued in connection with International Patent Application No. PCT/US2022/070304, Sep. 28, 2023, 11 pages.
First Office Action issued in corresponding Japanese Patent Application No. 2021-506973, Jun. 5, 2023, 5 pages.
1 Non-Final Office Action issued in connection with U.S. Appl. No. 17/149,527, filed Jan. 3, 2024, 17 pages.
Non-Final Office Action issued in connection with U.S. Appl. No. 17/359,745, filed Nov. 16, 2023, 7 pages.
First Office Action issued in connection with Chinese Patent Application No. 201910099418.5, Feb. 7, 2024, 14 pages.
Non-Final Office Action issued in connection with U.S. Appl. No. 17/227,971, filed Feb. 16, 2024, 17 pages.
Extended European Search Report issued in connection with European Patent Application No. 23210681.5, Feb. 12, 2024, 9 pages.
1 Non-Final Office Action issued in connection with U.S. Appl. No. 17/451,499, filed Feb. 9, 2024, 7 pages.
Non-Final Office Action issued in connection with U.S. Appl. No. 17/215,242, filed Feb. 1, 2024, 7 pages.
Extended European Search Report issued in connection with European Patent Application No. 23214740.9, 7 pages, Apr. 29, 2024.
Notice of Allowance issued in connection with U.S. Appl. No. 16/648,128, Feb. 16, 2024, 9 pages.
Non-Final Office Action issued in connection with U.S. Appl. No. 17/643,436, filed May 22, 2024, 13 pages.
Extended European Search Report issued in connection with European Patent Application No. 24162840.3, Jun. 21, 2024, 11 pages.

\* cited by examiner

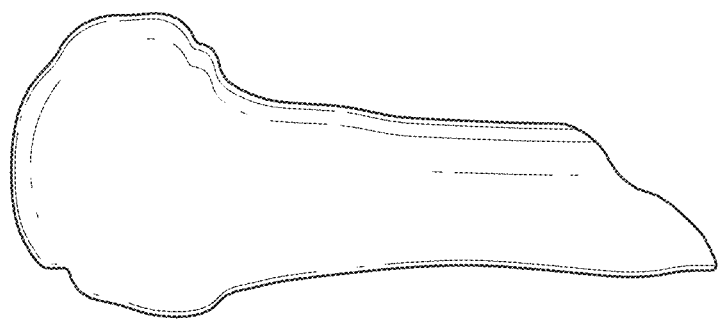
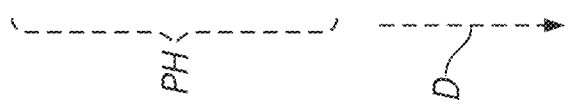
FIG. 1A
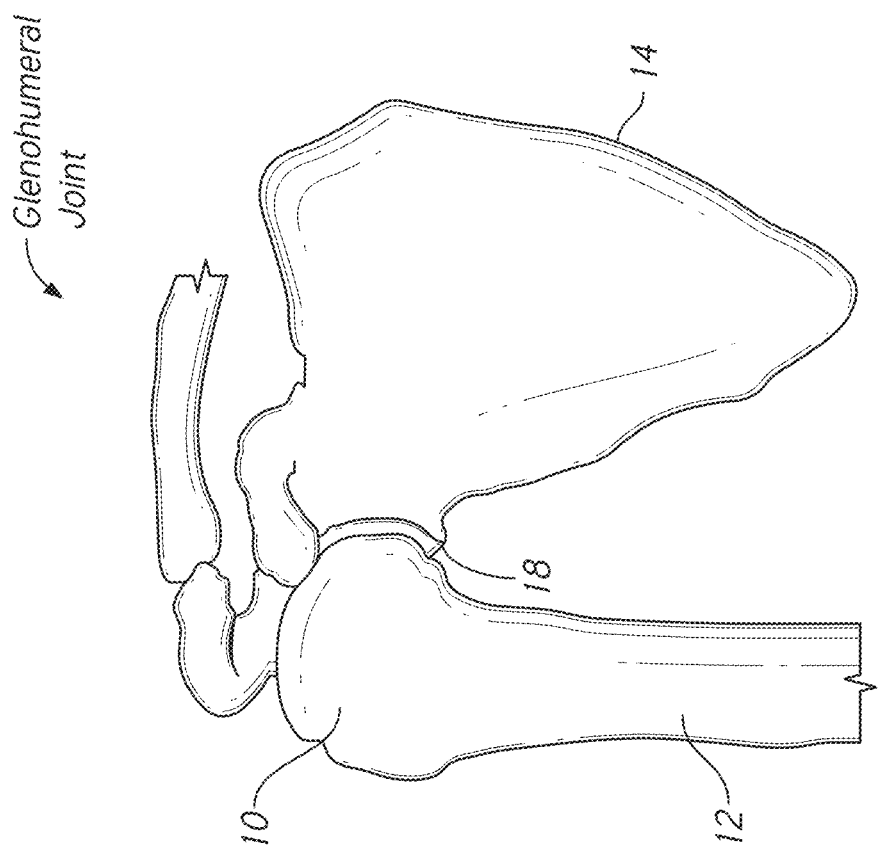
FIG. 1

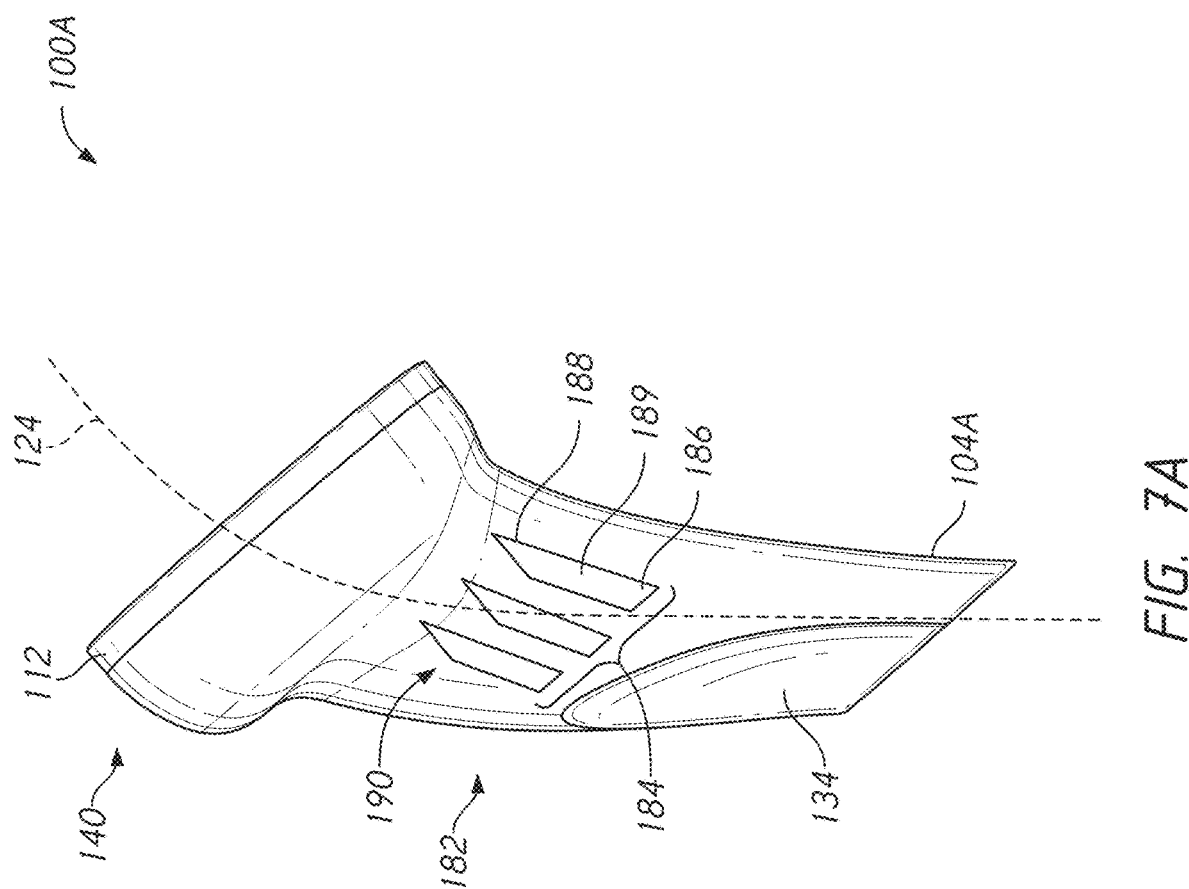

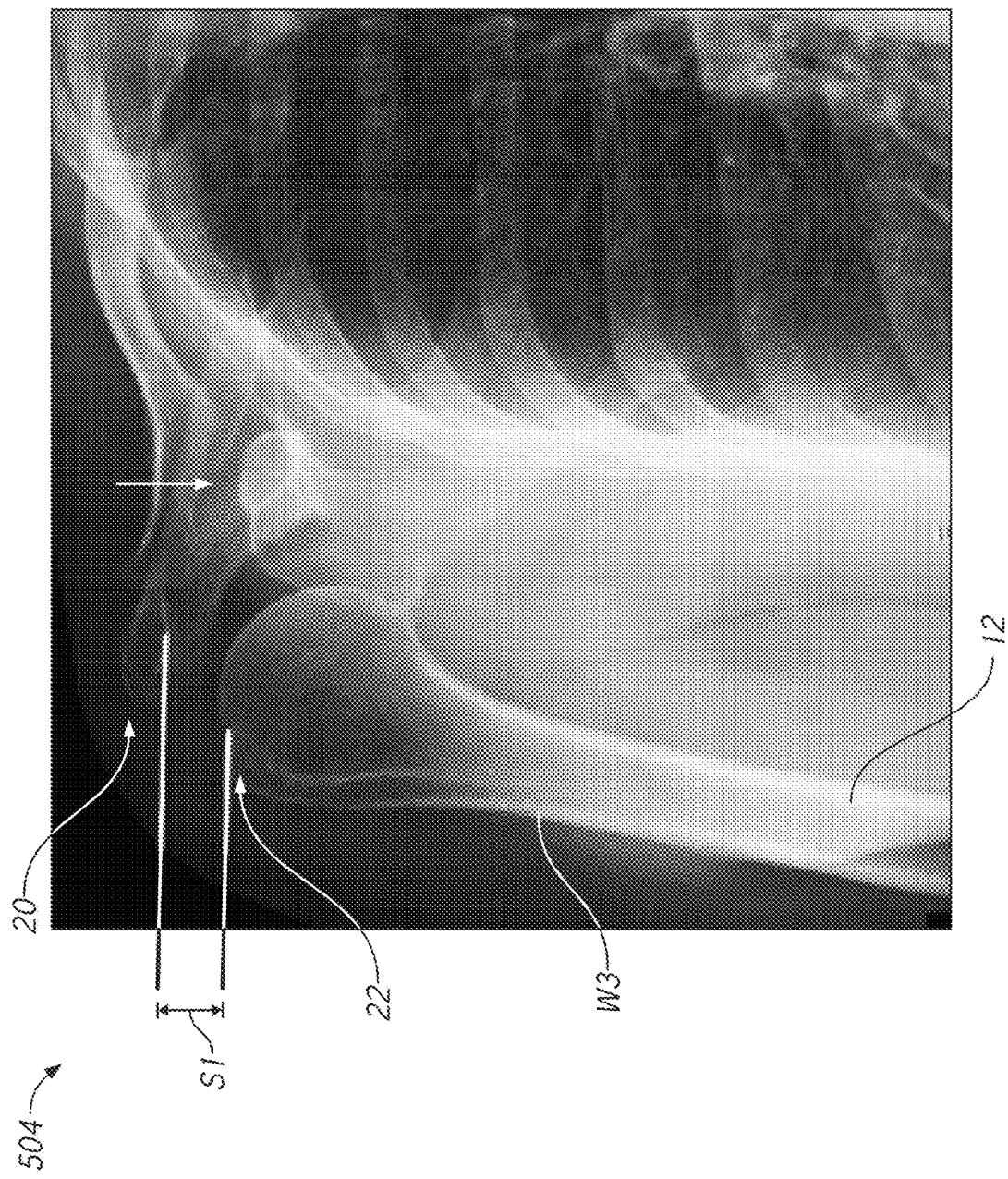

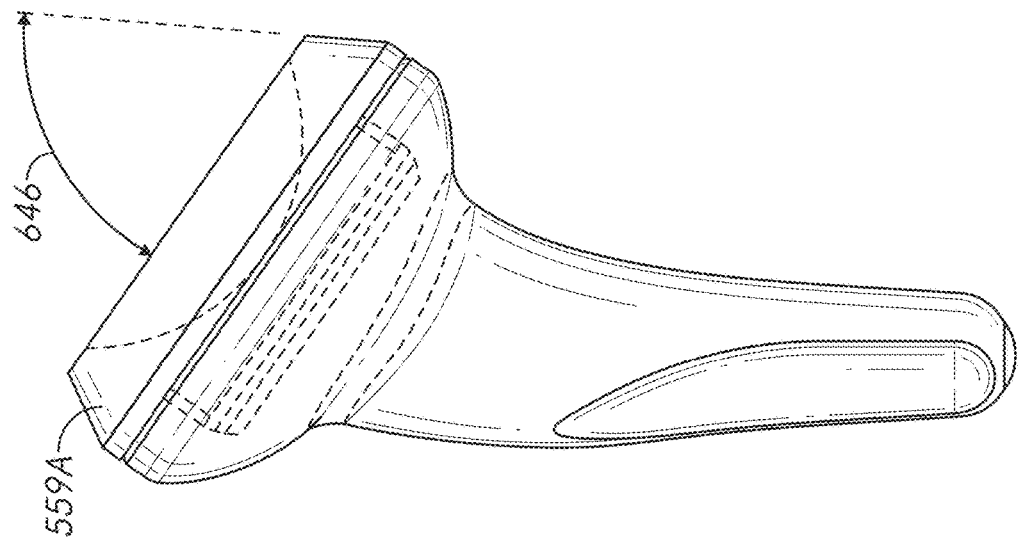
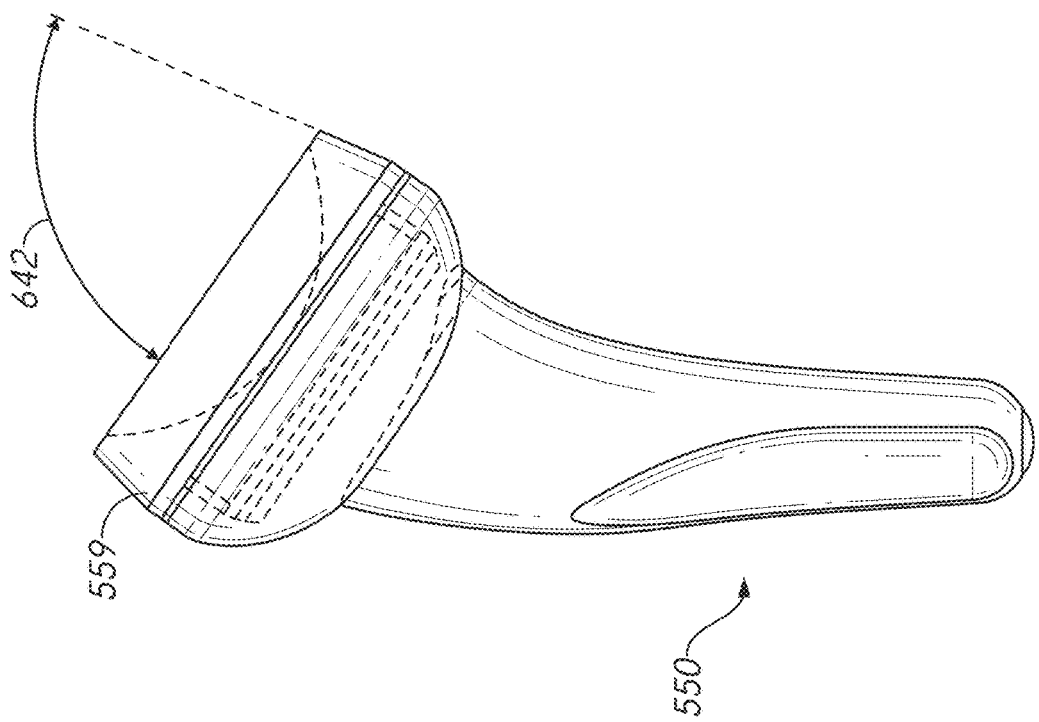
FIG. 26

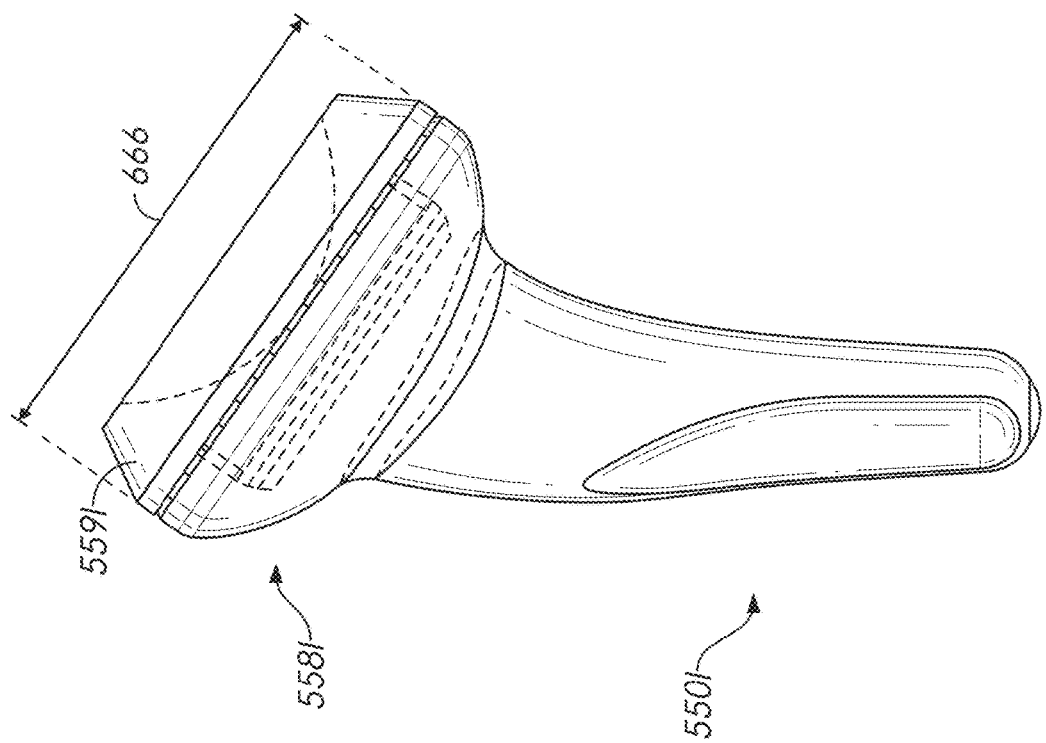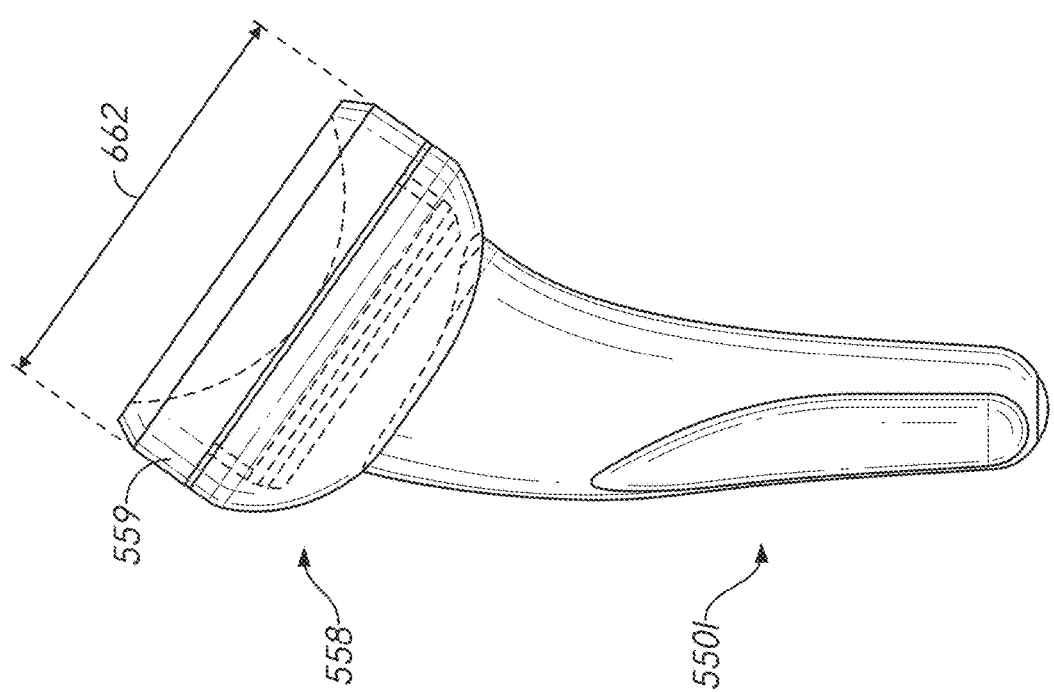
FIG. 27

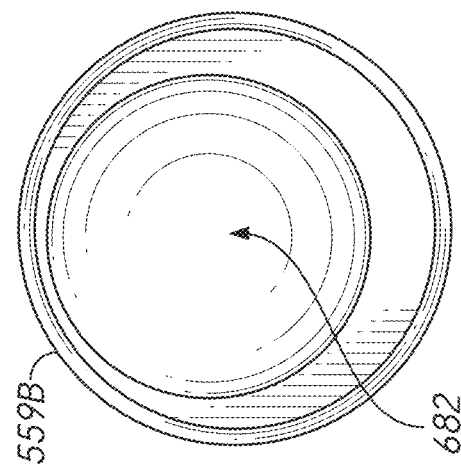
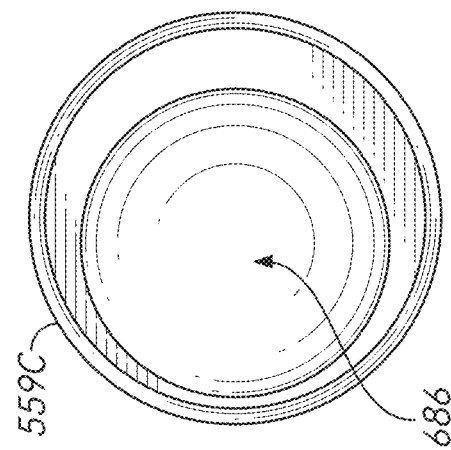
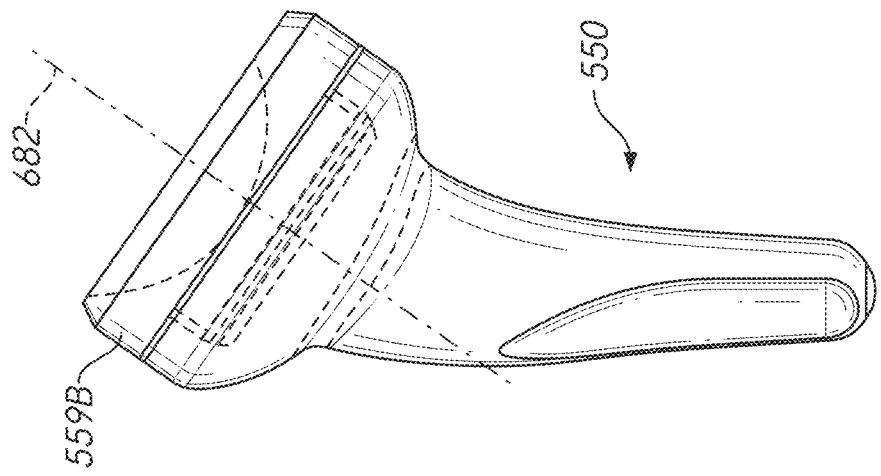
FIG. 28

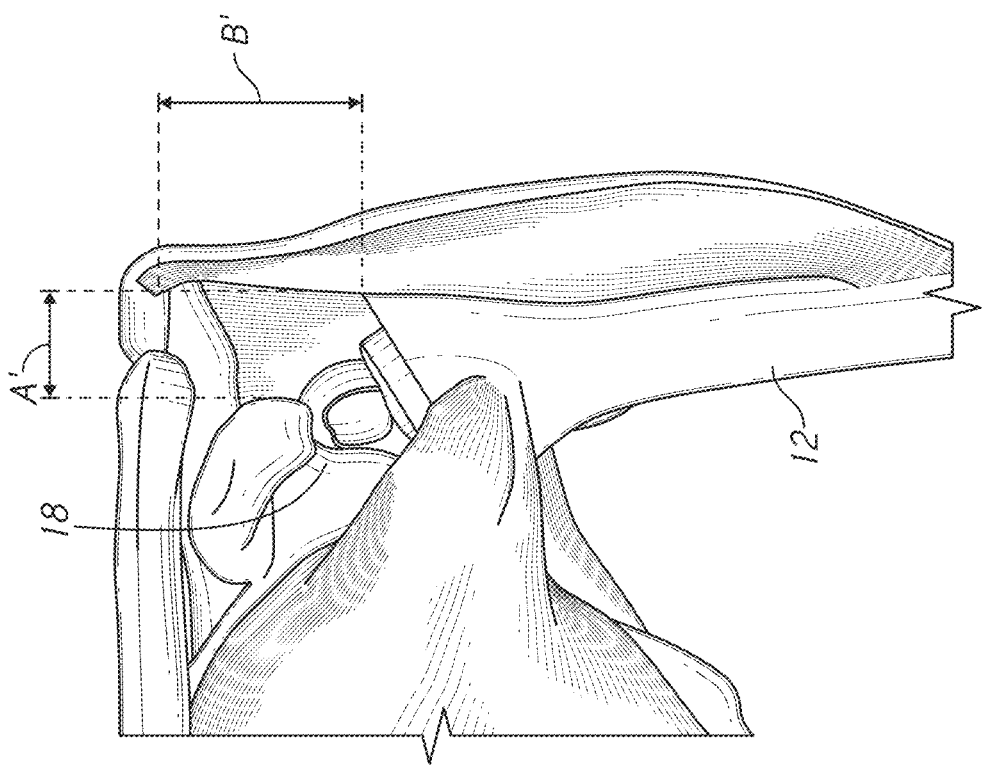
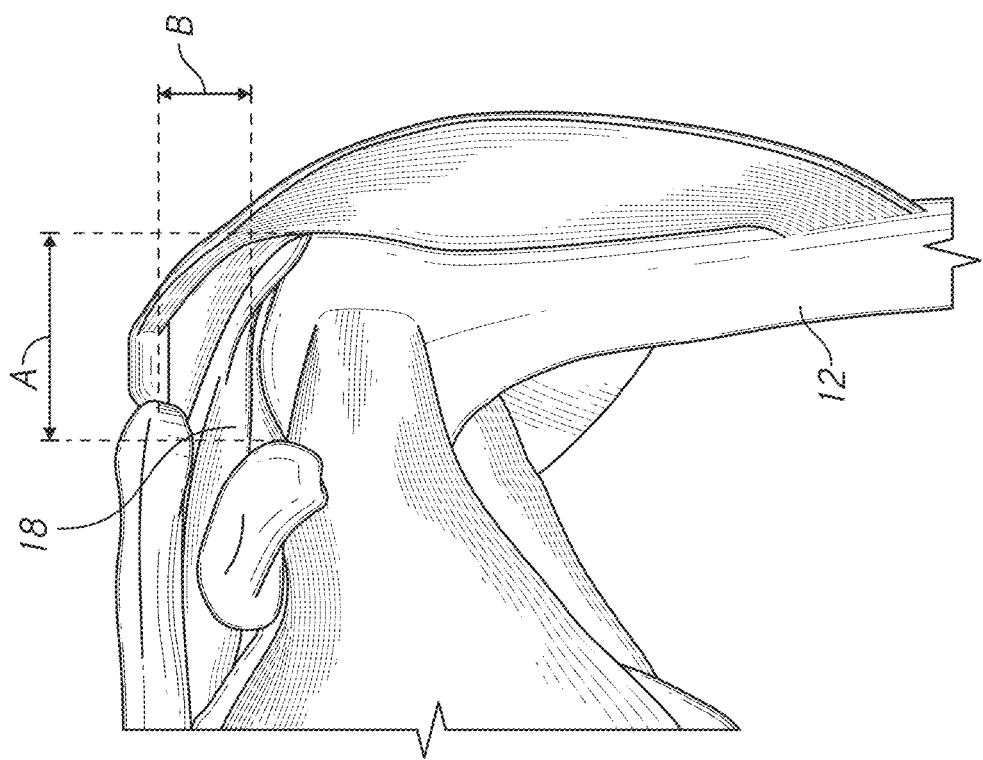
FIG. 32

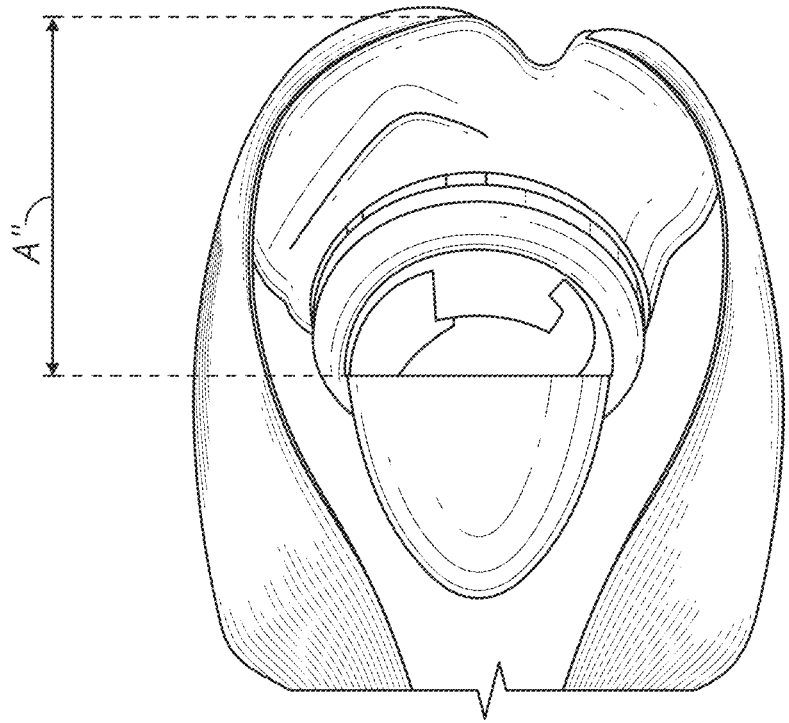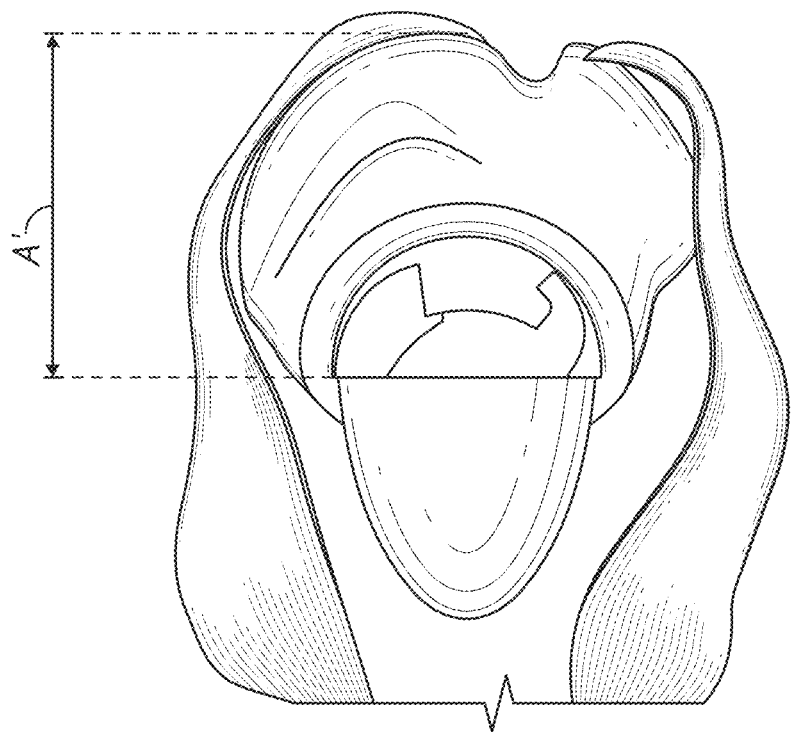
FIG. 33

PATIENT SPECIFIC HUMERAL IMPLANT COMPONENTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to enhanced fit, e.g., patient specific, shoulder implant components and instruments, and the use of the same in surgical methods.

Description of the Related Art

Arthroplasty is the standard of care for the treatment of shoulder joint arthritis. A typical anatomical shoulder joint replacement attempts to mimic anatomic conditions. For example, a metallic humeral stem and a humeral head replacement are attached to the humerus of the arm and replace the humeral side of the arthritic shoulder joint. Such humeral head replacement can articulate with the native glenoid socket or with an opposing glenoid resurfacing device.

For more severe cases of shoulder arthritis, the standard treatment is a reverse reconstruction, which includes reversing the kinematics of the shoulder joint. A reverse shoulder prosthesis can be provided by securing a semi-spherical articular component (sometimes called a glenoid sphere) to the glenoid and implanting a humeral component with a concave surface capable of receiving the glenoid sphere.

As patient disease may progress after anatomic treatment, revision surgery may be necessary to perform a reverse reconstruction of the shoulder. In the known art, the change in the type of prosthesis is addressed either below the plane of resection or above the plane of resection. In prostheses that are converted from anatomic to reverse by a modularity below the plane of resection, removal of anatomic devices that have integrated into the patient's bony anatomy proves to be difficult for the surgeon, and could potentially cause excessive patient bone loss. One advantage of such conversion is that the reverse insert could partially reside below the resection plane and therefore reduce the distance between the cavity and the lateral contour of the humerus. Such position has proven to be beneficial to reversed shoulder kinematics.

Commercial systems capable of being originally implanted as anatomic shoulder prostheses and later converted to reverse shoulder prostheses require a large array of components. For example, one system includes cemented and press-fit stems that are provided in eight different sizes. To provide for adjustment in location of center of rotation, anatomic articular components with two off-set configurations are provided and reverse articular assemblies with two off-set tray configurations are provided. In the end only two or three of these many components are used for a specific surgery resulting in waste or in supply chain complexities in maintaining inventory or in retrieving and refurbishing components that are not used in the specific surgery.

SUMMARY OF THE INVENTION

It would be desirable to provide improved shoulder implants that provide for a good initial fit in a specific patient, revision capabilities, and a more streamlined manner of equipping surgeons to serve patients in an efficient manner in some embodiments.

In one embodiment, a humeral implant is provided that includes a hollow stem and a mounting end. The hollow stem has a sharp distal edge. The mounting end has a mounting hole and a mounting channel disposed about the mounting hole. The mounting hole is configured to receive a tapered projection of an anatomic articular body. The mounting channel is configured to receive an annular projection of a reverse articular body.

In another embodiment a humeral implant assembly is provided that includes a stem, a locking mechanism, and an articular body. The stem has an inferior end and a superior mounting end. The mounting end has a peripheral wall and a mounting channel disposed within the peripheral wall. The locking mechanism has a plurality of flexible flanges that extend away from the peripheral wall. The flexible flanges have a free end. The free end is disposed away from the peripheral wall in a first configuration. The articular body has a mounting projection on an inferior side of the body. In one embodiment, the mounting projection has a superior facing taper.

In the foregoing embodiment, in a second configuration, when the mounting projection of the articular body is initially inserted into the mounting channel, the flexible flanges are disposed toward the peripheral wall of the mounting end of the stem. In a third configuration, when the mounting projection of the articular body is further inserted into the mounting channel, the free ends are disposed away from the peripheral wall to face or abut the superior facing taper. The free ends block the mounting portion from being removed from the mounting channel in the third configuration.

In another embodiment a humeral stem is provided. The stem has an inferior end and a superior mounting end. The mounting end has a peripheral wall and a mounting channel disposed within the peripheral wall. The locking mechanism has a plurality of flexible flanges that extend away from the peripheral wall. The flexible flanges have a free end. The free end is disposed away from the peripheral wall in a first configuration. In various embodiments, the stem has four, ten, twenty, and more than thirty flexible flanges. In various embodiments the stem has a continuous expanse of material within its outer surface. In various embodiments the stem is hollow.

In the foregoing embodiment, a second configuration can be provided when an articular body is initially inserted into the mounting channel, the flexible flanges are disposed toward the peripheral wall of the mounting end of the stem. In a third configuration, when the articular body is further inserted into the mounting channel, the free ends are disposed away from the peripheral wall to face or abut the superior facing taper. The free ends block the mounting portion from being removed from the mounting channel in the third configuration.

In another embodiment, a method is provided. In the method, access is provided to a metaphyseal portion of a humeral stem disposed in a proximal end of a humerus. The metaphyseal portion has a plurality of flexible flanges that extend away from a peripheral wall that surrounds a mounting channel. The mounting channel is accessible from a superior end of the metaphyseal portion. The flexible flanges have a free end disposed away from the peripheral wall. A mounting projection disposed on an inferior side of an articular body is advanced into the mounting channel and into contact with the flexible flanges. The mounting projection has a superior facing taper. The mounting projection is further advanced to move the flexible flanges toward the peripheral wall. The mounting projection is further advanced until the free ends of the flexible flanges are disposed away from the peripheral wall. When so disposed the flexible flanges face or abut the superior facing taper. When so disposed the flexible flanges block egress of the mounting projection from the mounting channel. When so disposed the flexible flanges secure the articular body to the stem.

In another embodiment a kit is provided that includes a humeral stem and a reamer head. The humeral stem has a diaphysis portion and a metaphysis portion. The metaphysis portion has a patient specific inferior, exterior surface. The reamer head has a patient specific inferior, exterior surface. The inferior, exterior surface of the reamer head corresponds to the patient specific inferior, exterior surface of the metaphysis portion.

In another embodiment, a method provides a reverse shoulder joint humeral implant. The humeral implant has a humeral anchor and an articular body. Glenohumeral joint information of a specific patient is obtained. An initial manufacturing plan is provided for making at least part of the humeral implant with reference to the glenohumeral joint information. The humeral implant has a patient specific characteristic in one or more of inclination angle, center of rotation offset, version angle, tensioning dimension, lead angle, metaphysis transverse size, articular surface offset, inlay depth, jump distance, jump distance asymmetry, or humeral anchor shape. A biomechanical analysis of a virtual humeral implant is performed in a virtual glenohumeral joint based upon the manufacturing plan. A final manufacturing plan for making at least part of the humeral implant is confirmed based on the biomechanical analysis of the glenohumeral joint. At least part of the humeral implant is manufactured following the final manufacturing plan.

In another embodiment a reverse shoulder humeral implant is provided. The humeral implant includes a humeral anchor and an articular body. The humeral anchor has a stem disposed at an inferior end thereof and an enlarged mounting portion disposed at a superior end thereof. The superior end of the enlarged mounting portion has a mounting face. The articular body has a concave articular portion, and outer surface, and a mounting portion. The concave articular portion has a superior edge. The outer surface extends away from the superior edge. The mounting portion is disposed opposite the articular portion and is configured to mate with the enlarged mounting portion of the humeral anchor. The humeral implant is configured for a specific patient based on pre-operative imaging with respect to one or more of inclination angle, center of rotation offset, version angle, tensioning dimension, lead angle, metaphysis transverse size, articular surface offset, inlay depth, jump distance, jump distance asymmetry, or humeral anchor shape.

An aspect of good initial fit involves soft tissue considerations. It is preferred to sufficiently (but not overly) tension the soft tissues around the shoulder joint. This can be achieved by a component that can lengthen the arm to take up laxity in the deltoid muscles or connective tissues at the shoulder. This can be achieved by a component that can lateralize the proximal humerus to take up laxity in the relevant soft tissue. In some embodiments soft tissue adjustments can be made independently in medial-lateral and in superior-inferior direction to improve overall fit.

In one embodiment, a humeral positioning system is disclosed. The humeral positioning system can include a humeral anchor disposed at an inferior end thereof and an enlarged mounting portion disposed at a superior end thereof. The superior end of the enlarged mounting portion can have a mounting face, with an axis perpendicular to the superior end intersecting a center of rotation of a neutral configuration of the humeral positioning system. The humeral positioning system can include an articular component having an engagement portion configured to connect to the mounting surface of the humeral anchor and an articular surface opposite the engagement portion. A center of rotation of the articular surface can be offset relative to the center of rotation of the neutral configuration in at least one of a medial-lateral direction and an inferior-superior direction when the engagement portion is coupled with the mounting surface of the humeral anchor.

In another embodiment, a humeral positioning system is disclosed. The humeral positioning system can include a humeral anchor comprising a first surface configured be disposed in bone inferior to a resection of a humerus to secure the humeral anchor to the humerus and a mounting portion disposed at a superior end thereof, the mounting portion having a mounting face. The humeral positioning system can include an articular component having an engagement portion configured to connect to the mounting face of the humeral anchor and an articular surface opposite the engagement portion. The center of rotation of the articular surface can be offset from an axis disposed perpendicular to the superior end by different amounts in a medial-lateral direction and in an inferior-superior direction.

In another embodiment, a method is disclosed. The method can include accessing a shoulder joint of a patient and removing a humeral head from a distal humerus. The method can include securing a humeral anchor to the distal humerus. The method can include assessing a position of the scapula and/or the humerus to determine a desired position of an articular surface of a humeral positioning system. The method can include selecting an articular component from a plurality of pre-made humeral components including at least one humeral components capable of independently adjusting medial-lateral and inferior-superior offsets, such that the selected articular component provides the desired position of the articular surface when the articular component is coupled with the humeral anchor and is in contact with an articular component coupled with the scapula.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 1 is a schematic view of anatomy around the shoulder joint;

FIG. 1A is a schematic view of a portion of a humerus;

FIG. 7A is an anterior view of another embodiment of a humeral stem a bone integration feature that can be incorporated into various embodiments;

FIG. 20C shows analyses that can inform considerations of soft tissue tensioning in providing an initial or a final manufacturing plan;

FIG. 26 includes anterior views of view of two embodiments of a humeral anchor, each having a different level of a lead angle between a side surface of an articular body and a superior plane of the articular body;

FIG. 27 includes anterior views of view of two embodiments of a humeral anchor, each having a metaphysis portion with a different width;

FIG. 28 includes anterior and superior views of one embodiments of humeral anchor and a superior view of a second embodiment of a humeral anchor, the superior views showing embodiments with different levels of offset between a geometric center of an articular body and a center of rotation of the articular body;

FIG. 32 is a schematic representation of a shoulder joint illustrating deltoid muscle tensioning before and after implantation of a shoulder prosthesis illustrating anatomical dimensions in a medial-lateral direction and in an inferior-superior direction;

FIG. 33 is a schematic representation of a shoulder joint, illustrating cuff tensioning with different shoulder joint implant configurations;

DETAILED DESCRIPTION OF THE PREFERRED EMBODIMENT

Figure 3:
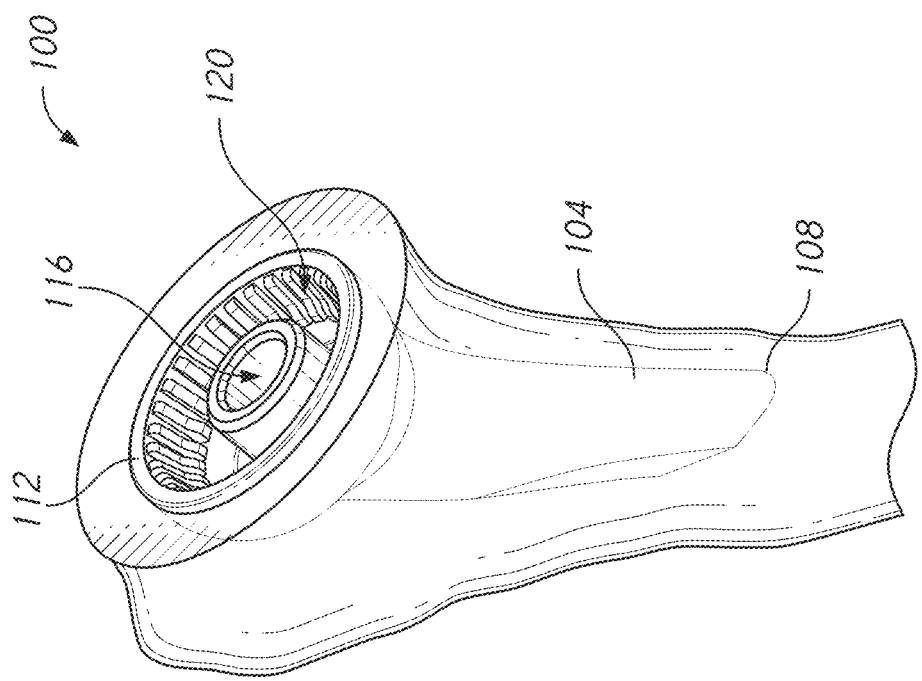
FIG. 3 is a perspective view of a humeral stem disposed in a schematic humerus.

This application is directed to enhanced reversible shoulder implants that better serve patients and the surgeons who implant them. The enhanced reversible shoulder implants can be deployed without a separate tray or adapter in a reverse configuration. The enhanced reversible shoulder implants can be made patient specific in some embodiments such that the implants provide excellent fit and also eliminate the need to size for a specific patient during the surgery. In other embodiments, a portion of a shoulder joint assembly can be fit to a patient by selection or use of a component that can adjust soft tissue tension in one or more directions relative to the shoulder joint. A portion of a shoulder joint assembly can be fit to a patient to increase tension in a medial-lateral direction (e.g., of rotator cuff tissue) without changing tension in an inferior-superior direction (e.g., of the deltoid muscle). A portion of a shoulder joint assembly can be fit to a patient to increase tension in an inferior-superior direction (e.g., of the deltoid muscle) without changing tension in a medial-lateral direction (e.g., of rotator cuff tissue). The tension-adjusting component can be patient generic or patient specific. These improvements can greatly simplify the kits supplied for a surgery as well as reducing waste and systems to recover and refurbish un-used components of kits.

I. Shoulder Anatomy

FIG. 1 shows anatomy of a glenohumeral joint. The joint is formed in part by a head 10 of a humerus 12 and a glenoid 18 of a scapula 14. The head 10 is located at the superior end the humerus and includes a convex articular structure that is generally spherical. The glenoid 18 includes a concave articular surface upon which the convex surface of the head 10 moves. FIG. 1A shows that the humerus has a medial side (right side in the view) and a lateral side (left side in the view). The proximal humerus PH includes the head 10 and a portion of the humerus distal the neck. The distal humerus D is located between the proximal humerus and the elbow end of the humerus. The proximal humerus is also superior to the distal humerus D. The elbow end of the humerus is also inferior to the proximal humerus PH.

II. Humeral Stem Innovations

Various humeral component and method innovations are discussed herein. Various methods of making humeral components patient specific are discussed below. Embodiments of inventive humeral components that are, in some embodiments, well adapted for patient specific applications are discussed below. As discussed further below, patient specific shoulder, e.g., humeral, components can be made by obtaining imaging of a relevant bone, e.g., of a humerus, a glenoid or other scapular region to be replaced and/or in some cases of a bone being treated on an opposite side of the shoulder joint. That imaging can be obtained any time, such as in a portion of a pre-operative analysis of the patient but even intra-operatively in some cases. The imaging can include 3D imaging as can be captured using MRI, CT scan, X-ray imaging or similar technologies. That imaging can be used to inform the specific configuration of portions of one or more implants as discussed below to provide improved performance including, for example, improved fit, bone integration, soft tissue tensioning, and reduction in dislocation risk. In Sections II(A)-II(D) below, a number of strategies to make a reversible shoulder implant are discussed. In Section III below a number of strategies to make a humeral component patient specific are discussed, with a focus on reversible patient specific humeral implant.

A. Hollow Humeral Stem Improvements

Figure 2:
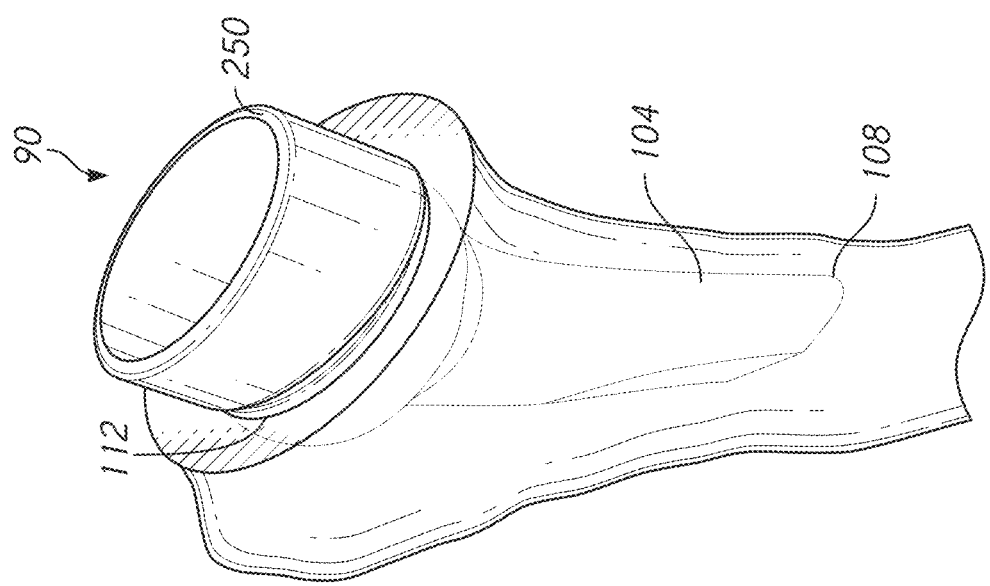
FIG. 2 is a perspective view of a humeral implant disposed in a schematic humerus.

FIG. 2 shows a humeral implant 90 according to one embodiment disclosed herein. The humeral implant 90 includes a humeral stem 100 and a reverse articular body 250. The humeral stem 100 is shown embedded in the humerus 12. An example procedure for positioning the humeral stem 100 in the humerus 12 is discussed below in connection with FIGS. 16-18. The humeral stem 100 is generally disposed in a portion of the proximal humerus PH adjacent to a resection surface, which is formed in the method of implanting. The humeral stem 100 includes an inferior edge 108 and a mounting end 112. The inferior edge 108 can be sharp to assist in implanting the humeral stem 100 as discussed further below. The sharp inferior edge 108 is located at an inferior or distal end of the humeral stem 100. Also, the humeral stem 100 can include a hollow shaft 104, which also assist in implanting the humeral stem 100.

Figure 7:
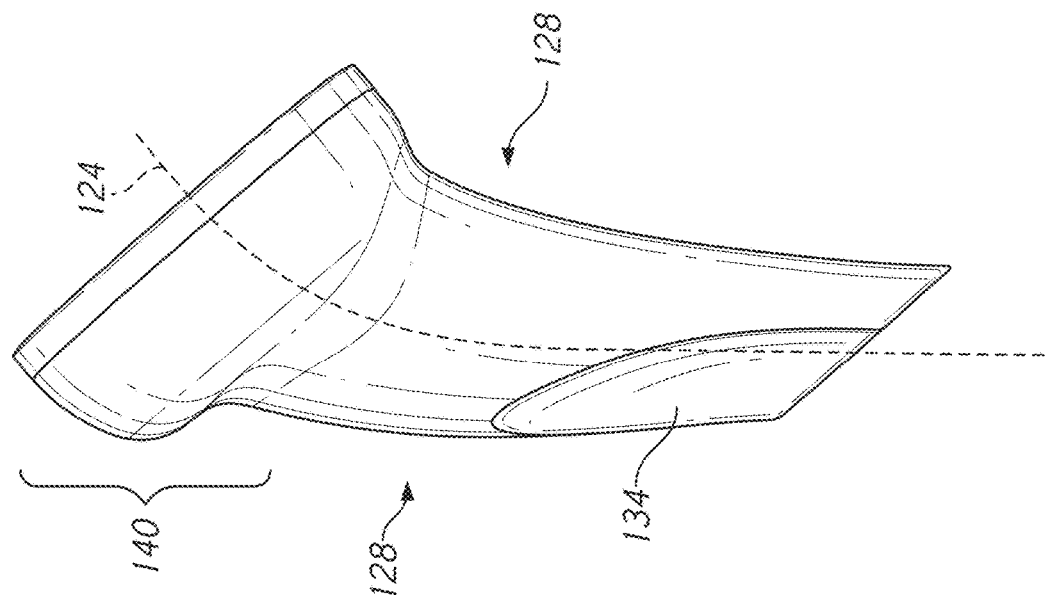
FIG. 7 is an anterior view of the humeral stem illustrated in FIG. 4 showing patient specific aspect of metaphyseal shape of a mounting end of the humeral stem.

The mounting end 112 is located on a superior or proximal end of the humeral stem 100. The mounting end 112 can be generally bowl shaped. In some cases, the mounting end 112 has an inferior curvature that can be characterized by a radius of curvature. The mounting end 112 can have a superior end that can be generally planar as indicated by FIG. 7. In some cases, the superior end of the humeral stem 100 is angled medially and the inferior end of the humeral stem 100 is angled laterally.

Figure 5:
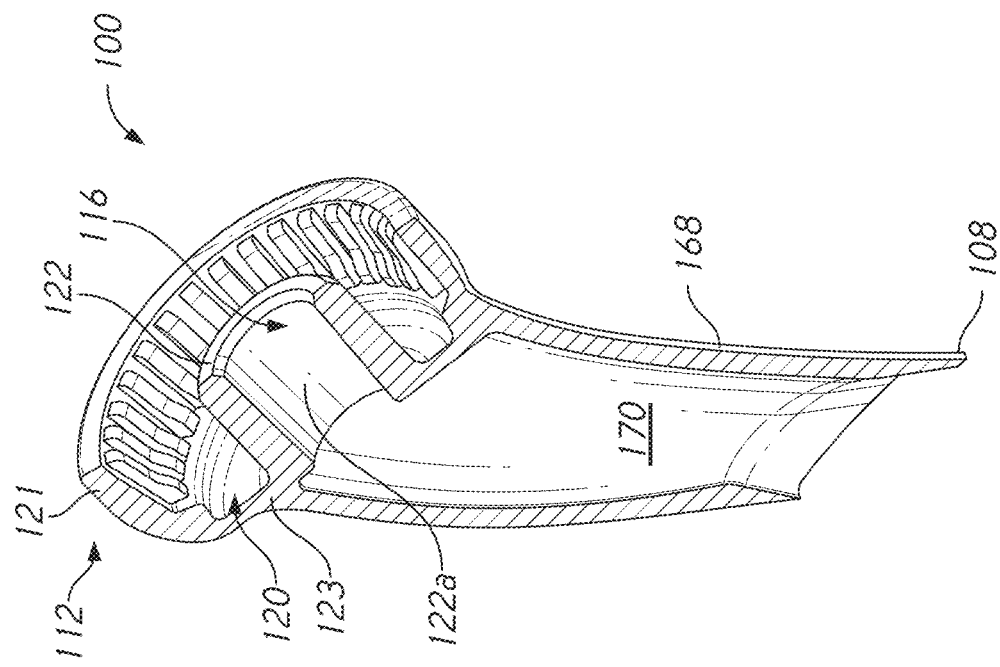
FIG. 5 is a cross-section of the humeral stem taken through a longitudinal axis of the humeral stem.
Figure 4:
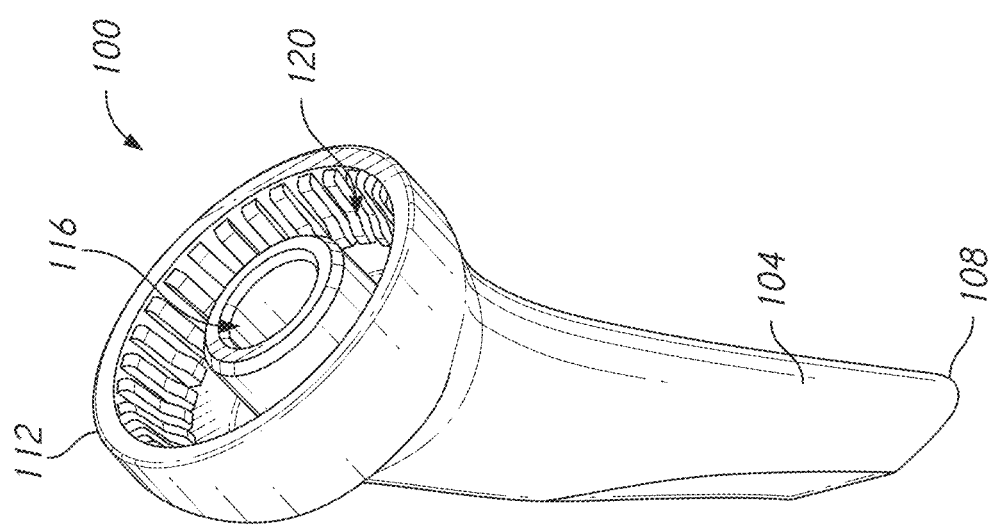
FIG. 4 is a perspective view of the humeral stem illustrated in FIG. 3 removed from the humerus.
Figure 9:
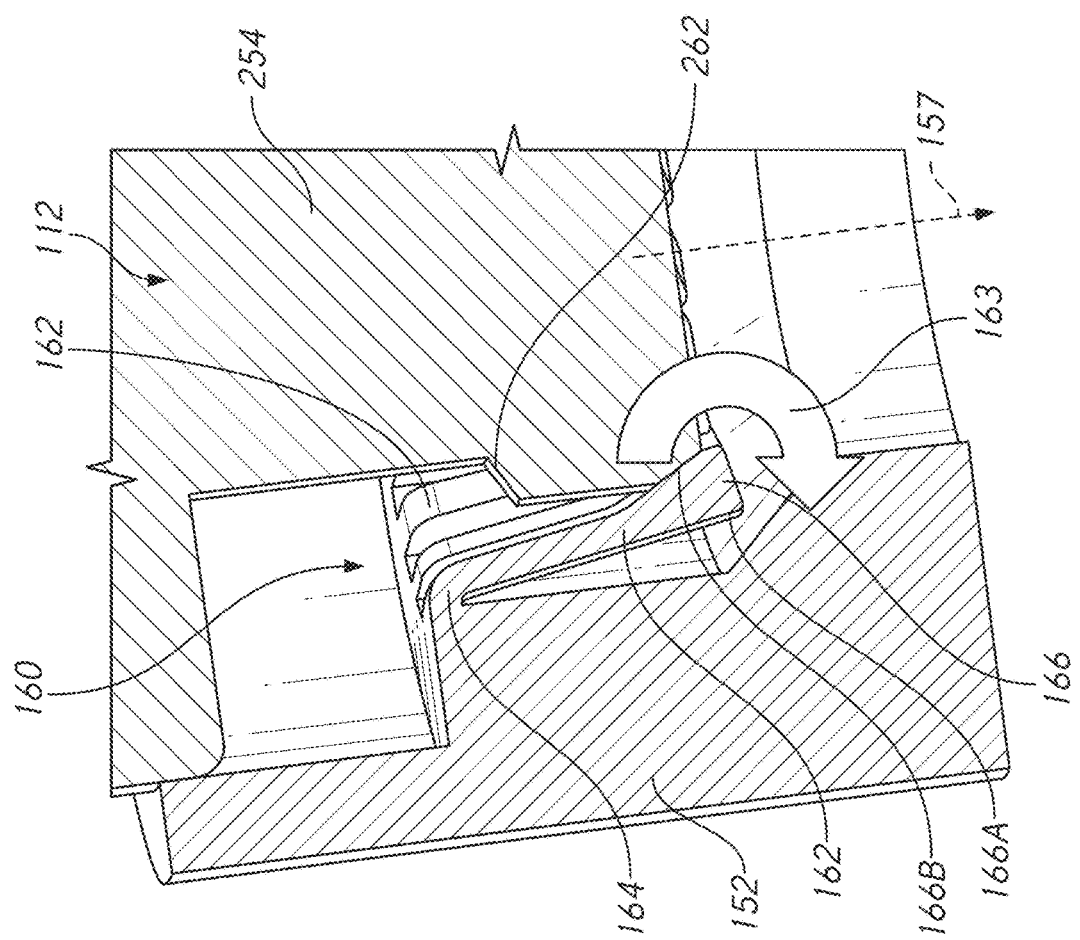
FIG. 9 is a detail view of the mounting end of the embodiment of FIG. 8 with a projection of a reverse articular body further inserted into the mounting end compared to the position of FIG. 8.

The humeral stem 100 can be made to couple directly with an anatomic articular body and also to directly couple with a reverse configuration articular body. FIG. 3 shows that in one embodiment the humeral stem 100 has a mounting hole 116 and also has a mounting channel 120. The mounting hole 116 is discussed further below. The mounting channel 120 includes an annular space that is exposed and accessible during the shoulder replacement procedure at the mounting end 112. FIG. 5 shows that the mounting channel 120 can be disposed between an outer wall 121 and an inner wall 122. In one embodiment, the mounting channel 120 extends entirely around the inner wall 122 to include a complete annular space. The mounting channel 120 can have other shapes, such as having one, two, three, or four discrete arcuate zones that are separated by radial walls. The mounting channel 120 could be one or more radial spaces rather than a circumferential space as illustrated in FIGS. 3-5. As discussed further below, the mounting channel 120 can include a locking mechanism 160. The locking mechanism 160 can be disposed at the outer wall 121, e.g., integrally formed with or extending from the outer wall 121 as illustrated in FIG. 9. In other embodiments the locking mechanism 160 can be disposed at the inner wall 122, e.g., integrally formed with or extending from the inner wall 122. The locking mechanism 160 can be disposed at the outer wall 121 and at the inner wall 122 in some embodiments, e.g., integrally formed with or extending from the outer wall 121 and from the inner wall 122.

In some variations, the mounting channel 120 is disposed around, e.g., surrounds the mounting hole 116. The mounting hole 116 can be defined by a portion of the inner wall 122 that faces a central zone of the mounting end 112. In one embodiment, the outer wall 121 and the inner wall 122 comprise circular peripheries that surround a common center. A portion of the inner wall 122 that faces the common center can surround the mounting hole 116. A portion of the inner wall 122 that faces the common center can define the mounting hole 116. In one embodiment, an inside surface 122a of the inner wall 122 is configured for mating with an anatomic articular body 208. For example, the inside surface 122a can be tapered, e.g., having a progressively smaller diameter along a length between a superior end of the humeral stem 100 and the inferior end thereof, e.g., from an opening into the mounting hole 116 to the transverse wall 123. Engagement of the anatomic articular body 208 with the mounting hole 116 at the mounting end 112 can be by an interference fit, such as by a Morse taper as discussed further below.

The hollow shaft 104 can have a form that is suitable for a patient. The form of the hollow shaft 104 can include a shape as defined along a longitudinal axis 124. For example, the hollow shaft 104 can be elongate along the longitudinal axis 124. The hollow shaft 104 can have a curvature along the longitudinal axis 124. As discussed further below a degree of curvature of the longitudinal axis 124 can be sized for classes of patient or can be patient specific based on an analysis of 3D imaging of a same curvature in the humerus of the patient. A patient specific curvature, e.g., radius, can be defined as corresponding to the curvature between the hollow shaft 104 and the mounting end 112 that best fits a characteristic such as providing enhanced bone filling or engagement or providing enhanced range of motion. This fit can be based on 3D imaging of the specific patient for which the humeral stem 100 is made.

Figure 6:
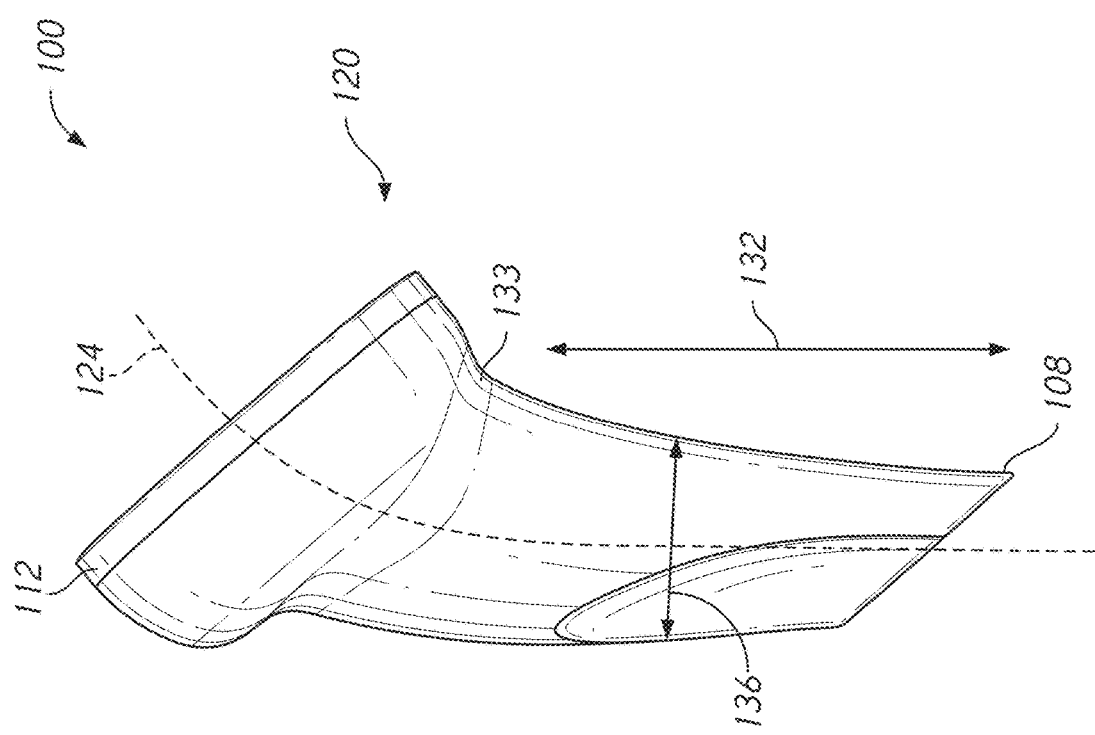
FIG. 6 is an anterior view of the humeral stem illustrated in FIG. 4 showing patient specific aspect of a shaft of the humeral stem.

The form of the hollow shaft 104 also can include a length 132 and a diameter 136. The length 132 can be a dimension as measured from the inferior edge 108 to the location of a base 133 of the mounting end 112. FIG. 6 shows that due to the orientation of the mounting end 112 relative to the hollow shaft 104 the length 132 defined on the inside of the curvature of the longitudinal axis 124 (also on the medial side of the humeral stem 100) is less than a similar length on the outside of the curvature of the longitudinal axis 124 (also on the lateral side of the humeral stem 100). Although FIG. 6 shows the length 132 as measured on the medial side of the humeral stem 100 the length 132 could be measured on the lateral side. In some techniques, the length on the lateral side is more critical. In some cases, the length on the lateral side follows from defining the orientation of the mounting end 112 (e.g., of a plane intersecting the superior end of the mounting end 112) and by defining the length 132 on the medial side of the humeral stem 100.

The form of the hollow shaft 104 can also be in part defined by a diameter 136 of the shaft 104. The diameter 136 can be defined transverse to the longitudinal axis 124. The diameter 136 can vary along the length of the shaft 104, e.g., larger toward the mounting end 112 and smaller toward the sharp inferior edge 108. The diameter 136 can be selected to be patient specific, enabling the hollow shaft 104 to fill the shaft of the humerus 12 to a degree that provides advantageous filling of the humerus 12. The diameter 136 can be constant along the length 132. The diameter 136 can be varying along the length 132. For example, the diameter 136 can increase along the longitudinal axis 124 between the sharp inferior edge 108 and the base 133 of the mounting end 112. In some embodiments, the diameter 136 can progressively increase from the sharp inferior edge 108 of the hollow shaft 104 to the base 133 of the mounting end 112.

The humeral stem 100 can have other lengths that are patient specific. For example, a length including the length 132 and a length of the mounting end 112 can be provided that is patient specific. The distance from the base 133 to the superior plane of the mounting end 112 on the medial side of the head 10 can be patient specific. The combination of the length 132 and the distance from the base 133 to the superior plane of the mounting end 112 on the medial side of the head 10 can be patient specific.

In some embodiments, the hollow shaft 104 is not circular or is not uniformly circular in cross-sections transverse to the longitudinal axis 124 along the length 132 of the hollow shaft 104. For example, in one embodiment an inferior portion disposed away from the mounting end 112 can have a flattened portion 134. The flattened portion 134 causes the hollow shaft 104 to extend outwardly to a lesser extent in the area of the flattened portion 134. The lesser extent of the flattened portion 134 can enable the hollow shaft 104 to be less close to the exterior surface of the humerus 12 at the location where the flattened portion 134 is placed. The flattened portion 134 can be provided in a specific region for a patient where the specific patient's humerus 12 is narrower transverse to the longitudinal axis of the humerus 12. The flattened portion 134 can be seen in transverse cross-section were a portion of the outer periphery of the hollow shaft 104 can be seen to have a circular portion in one region and an adjusted zone adjacent to the circular portion. The adjusted zone can have a non-circular periphery away from the circular portion. The adjusted zone can have a second circular periphery away from the circular portion, the second circular periphery being of a larger radius of curvature to provide a shallower area in the flattened portion 134.

Another aspect in which the humeral stem 100 can be made patient specific is in the mounting end 112. For example, the mounting end 112 can have a metaphyseal shape 140 that is patient specific. The metaphyseal shape 140 can be made patient specific with reference to 3D imaging, as discussed elsewhere herein. The metaphyseal shape 140 can have a patient specific metaphyseal volume with reference to 3D imaging. The metaphyseal shape 140 can include a radius of curvature of the base 133. The metaphyseal shape 140 can include a depth between the inferior plane of the mounting end 112 and the apex of the base 133 at a boundary with the hollow shaft 104. Other aspects of the configurations of the mounting end 112 and of the hollow shaft 104 that can be made patient specific are discussed below in connection with Section III.

1. Bone Integration Features

The stem embodiments disclosed herein can have various bone integration features formed therein or thereon. FIG. 7A shows that in one embodiment a humeral stem 100A includes a bone integration feature 182. The humeral stem 100A is similar to the humeral stem 100 except as described differently below. The humeral stem 100A can include a hollow shaft 104A that is similar to the hollow shaft 104 but that has the bone integration feature 182 formed therein. The bone integration feature 182 can include a plurality of apertures 184. The apertures of the plurality of apertures 184 can be arranged in any suitable manner. In one embodiment, the plurality of apertures 184 includes apertures that each have an inferior portion 186, a superior portion 188, and a space 189 disposed therethrough between the inferior portion 186 and the superior portion 188. The apertures of the plurality of apertures 184 can be generally aligned the longitudinal axis 124 of the humeral stem 100A. For example, the superior portion 188 of one of the apertures 184 can be superior of and medial of the inferior portion 186 of the aperture. The apertures of the plurality of apertures 184 can each be angled relative to a longitudinal axis of the hollow shaft 104A. The apertures of the plurality of apertures 184 can each be aligned to a normal to the mounting end 112. An angle between the aperture of the plurality of apertures 184 and a normal to the mounting end 112 can be less than an angle between the aperture and a longitudinal axis of the hollow shaft 104. The apertures can have a tapered end 190, e.g., at the superior portion 188 of the aperture. In other embodiments, the apertures can have a tapered end at the inferior portion 186 of the aperture. Both ends of the apertures of the plurality of apertures 184 can be tapered or non-tapered in other embodiments.

In use the humeral stem 100A is implanted in cancellous bone of the humerus 12 distal a resection plane 290. When so implanted, bone tissue can grow across the space 189 in the apertures of the plurality of apertures 184. Such bone growth can create a bridge of bone from outside the hollow shaft 104 to the open area 170 disposed within the hollow shaft 104A. In the illustrated embodiment, the bridged bone is concentrated in, e.g., entirely within a central zone of the hollow shaft 104A. The apertures of the plurality of apertures 184 can be focused in, e.g., only in, the zone between the flattened portion 134 and the base 133 of the mounting end 112. The plurality of apertures 184 can extend through the inferior wall 168. The plurality of apertures 184 can extend through a superior portion of the inferior wall 168. The plurality of apertures 184 can extend through an inferior portion of the inferior wall 168, e.g., through a zone including the flattened portion 134.

Although shown as being on the anterior side of the hollow shaft 104A the plurality of apertures 184 can include apertures formed on posterior side. The plurality of apertures 184 can include apertures formed on the anterior and posterior sides. The plurality of apertures 184 can include apertures formed on the medial side. The plurality of apertures 184 can include apertures formed on the lateral side. The plurality of apertures 184 can include apertures formed on the medial and lateral sides. The plurality of apertures 184 can include apertures formed at intervals around the entire outer surface of the inferior wall 168 in at least one zone, e.g., in a superior portion of the inferior wall 168 disposed between the flattened portion 134 and the base 133 of the mounting end 112, in the inferior wall 168 inferior of the base 133 of the mounting end 112, in an inferior portion of the inferior wall 168 including being disposed through the flattened portion 134.

Other structures can be provided for enhancing bone integration within the cancellous bone inferior of a resection plane. For example, the exterior surface of the inferior wall 168 can have a rough surface finish or a coating that enhances or hastens bone ingrowth. The interior surface of the inferior wall 168 can have a rough surface finish or a coating that enhances or hastens bone ingrowth. The exterior surface and the interior surface of the inferior wall 168 can have a rough surface finish or a coating that enhances or hastens bone ingrowth.

B. Articular Component Retention Configurations

Figure 8:
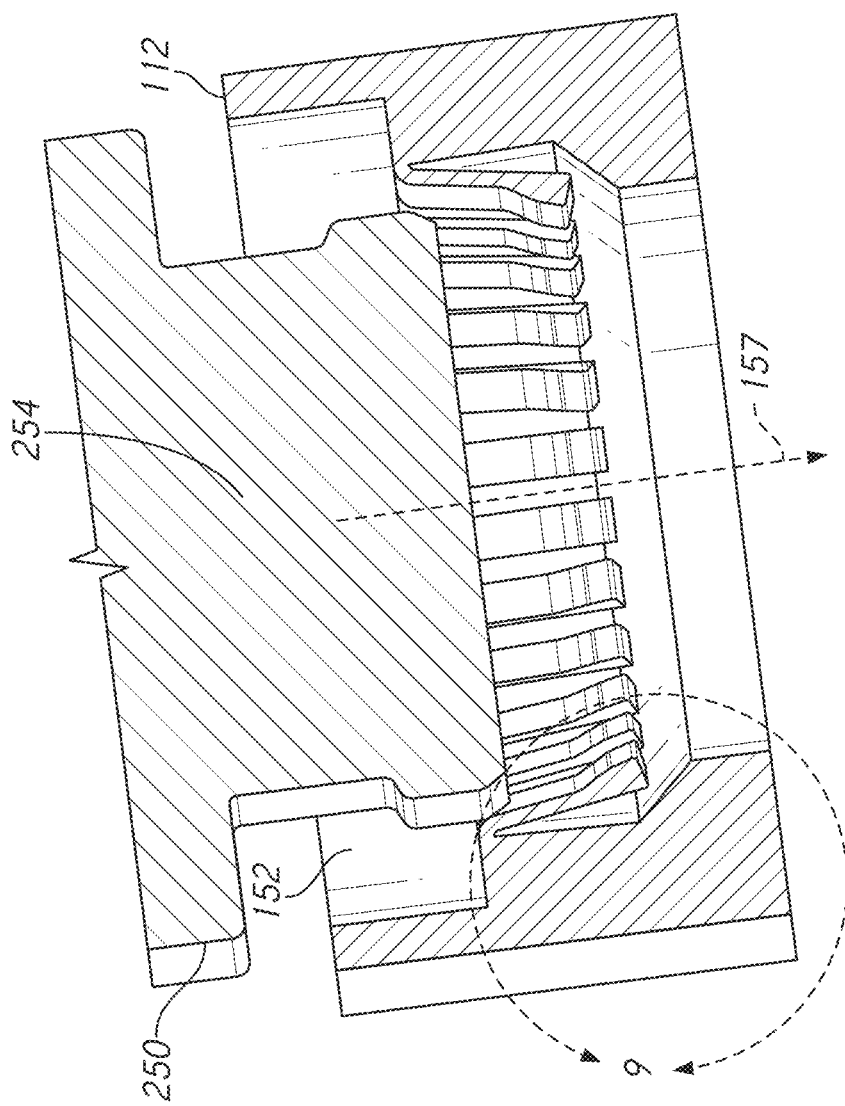
FIG. 8 is a cross-sectional schematic view of a mounting end of a humeral stem according to one embodiment with a projection of a reverse articular body partially inserted into the mounting end.

Various advantageous component retention configurations are provided in various embodiments. FIG. 8 shows an example of a connection between a reverse articular body 250 and the mounting end 112 of one variant of the humeral stem 100. The mounting end 112 includes a peripheral wall 152 that surrounds a space provided in the humeral stem 100. The peripheral wall 152 enables an annular projection 254 of the reverse articular body 250 to be inserted into the mounting end 112. The insertion of the annular projection 254 into the mounting end 112 can be along the direction of the arrow 157. FIG. 9 shows that in some embodiments further insertion of the annular projection 254 through the peripheral wall 152 causes the inferior end of the annular projection 254 to engage one or more flexible flanges 162 of a locking mechanism 160 at the mounting end 112 of the humeral stem 100. Following engagement, continued movement along the direction of the arrow 157 causes the flexible flanges 162 to move. For example, the flexible flanges 162 can include a first end 164 that is coupled with the peripheral wall 152 and a second end 166. The second end 166 is spaced away from the first end 164. The second end 166 is a free end. The second end 166 is disposed in a space or an open area 170 surrounded by the peripheral wall 152 and located away from the peripheral wall 152.

The second end 166 can have a wedge shape. The second end 166 can include an inner edge 166A and an outer edge 166B. A thickness defined between the inner edge 166A and the outer edge 166B can vary along the length of the flexible flanges 162 between the first end 164 and the second end 166. The thickness defined between the inner edge 166A and the outer edge 166B can increase between the first end 164 and the second end 166. The thickness defined between the inner edge 166A and the outer edge 166B can increase to the second end 166 from a location between the second end 166 and the flexible flanges 162. In one embodiment, the thickness defined between the inner edge 166A and the outer edge 166B increases by a first amount in a superior zone and by a second amount in an inferior zone. The first amount can be less than the second amount in various embodiments.

Figure 10:
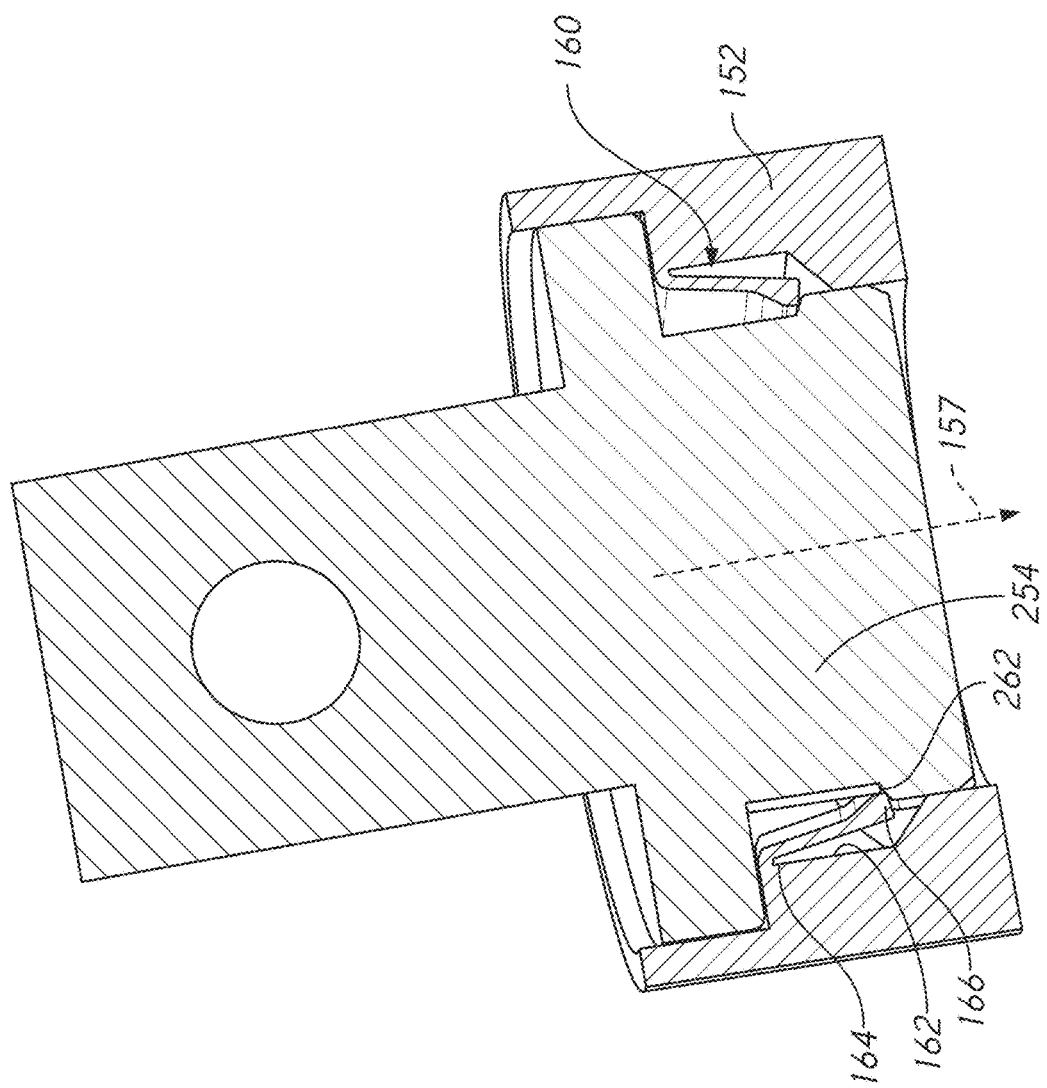
FIG. 10 is a detail view of the mounting end of the embodiment of FIG. 8 with a projection of a reverse articular body fully inserted into the mounting end.

FIG. 10 shows that the locking mechanism 160 actuates to a locked configuration upon final advancement of the annular projection 254 into the space or open area 170 surrounded by the peripheral wall 152. Upon full insertion of the annular projection 254 the flexible flanges 162 deflect into the open area 170 and away from the peripheral wall 152. Deflection of the flexible flanges 162 away from the peripheral wall 152 preferably results in a locking engagement between the annular projection 254 and the flexible flanges 162. The locking engagement can be provided between an inferior edge of the second end 166 and a superior facing taper 262 of the annular projection 254. The flexible flanges 162 can deflect away from the peripheral wall 152 until the inferior edge of the second end 166 is disposed over, e.g., facing or in some cases contacting the superior facing taper 262. If the inferior edge of the second end 166 is not touching the superior facing taper 262 the inferior edge is generally disposed directly above the superior facing taper 262 such that movement the opposite direction of the arrow 157 induces such contact which opposes and prevent further movement in the direction opposite the direction of the arrow 157.

Figure 11:
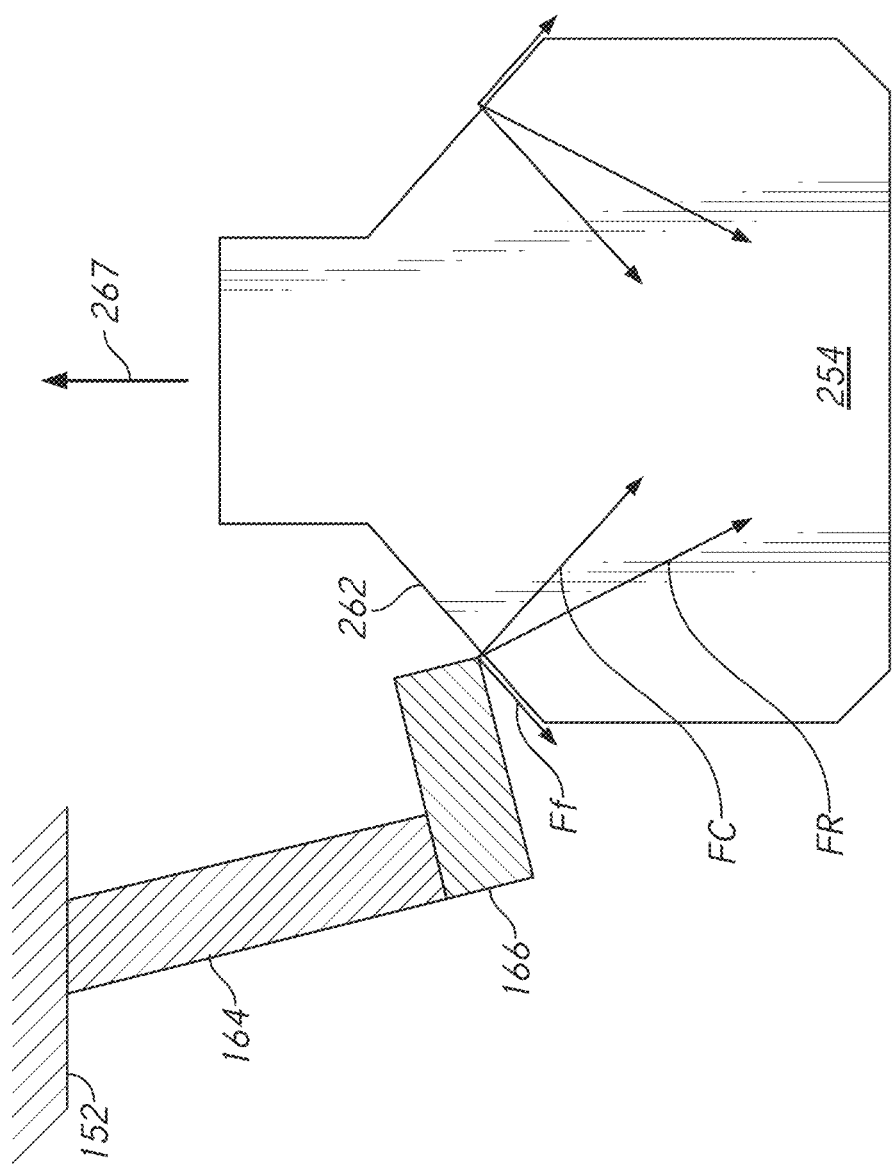
FIG. 11 is a schematic view of a force diagram for a flexible flange member of a locking mechanism of a humeral stem.
Figure 13:
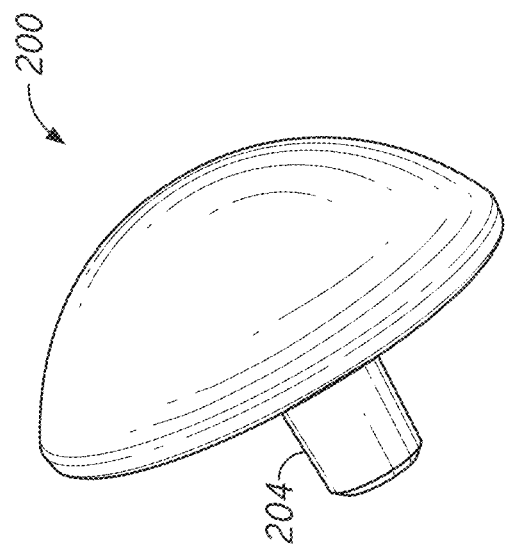
FIG. 13 is a side view of the anatomic articular body shown in FIG. 12.

FIG. 11 shows a model of the operation of the locking mechanism 160. A single one of the flexible flanges 162 is shown with the second end 166 thereof in contact with the superior facing taper 262 of a model of the annular projection 254 of a reverse articular body 250. An arrow 267 indicated a load being applied in a direction away from the humeral stem 100, e.g., superiorly. The first end 164 is shown in the analysis affixed to a ground surface, which is the peripheral wall 152. This is because the flexible flanges 162 are coupled with the mounting end 112 and are relatively inflexible in compressive loading. The relative inflexibility of the flexible flanges 162 causes force from the load along the arrow 267 to be opposed by an opposing force Fc from the peripheral wall 152 from which the flexible flanges 162 extend. The opposing force from the peripheral wall 152 is applied from the second end 166 to the superior facing taper 262. The opposing force Fc applied to the taper 262 and a friction force F1 are directed inferiorly and combine to a resultant force FR directed inferiorly. FIG. 11 shows that the inferiorly directed forces can be applied symmetrically on opposite sides of the annular projection 254. These forces can be applied all around the projection 254. These inferiorly directed forces counteract that force along the arrow 267 and as resolved result in great security to retain the articular body 250.

Figure 12:
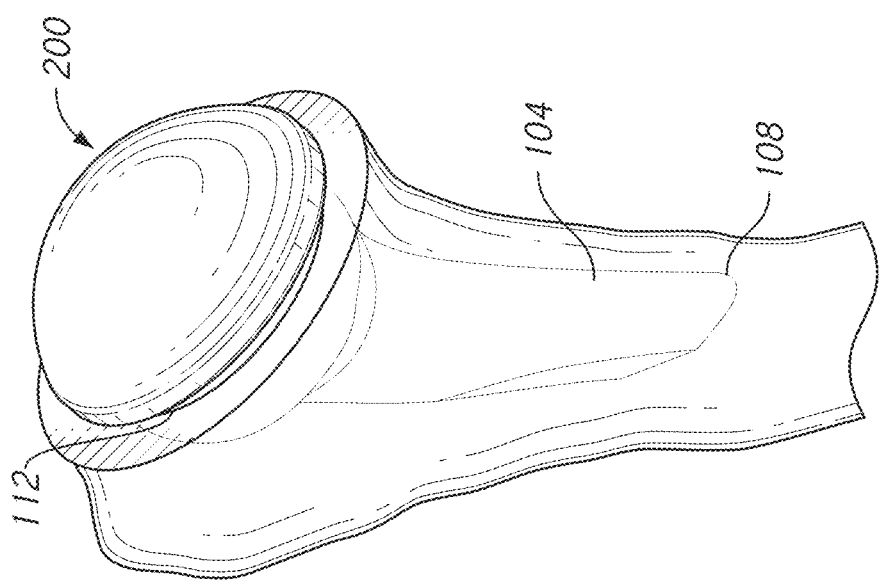
FIG. 12 is a perspective view of the humeral stem of FIG. 3 coupled with an anatomic articular body.
Figure 15:
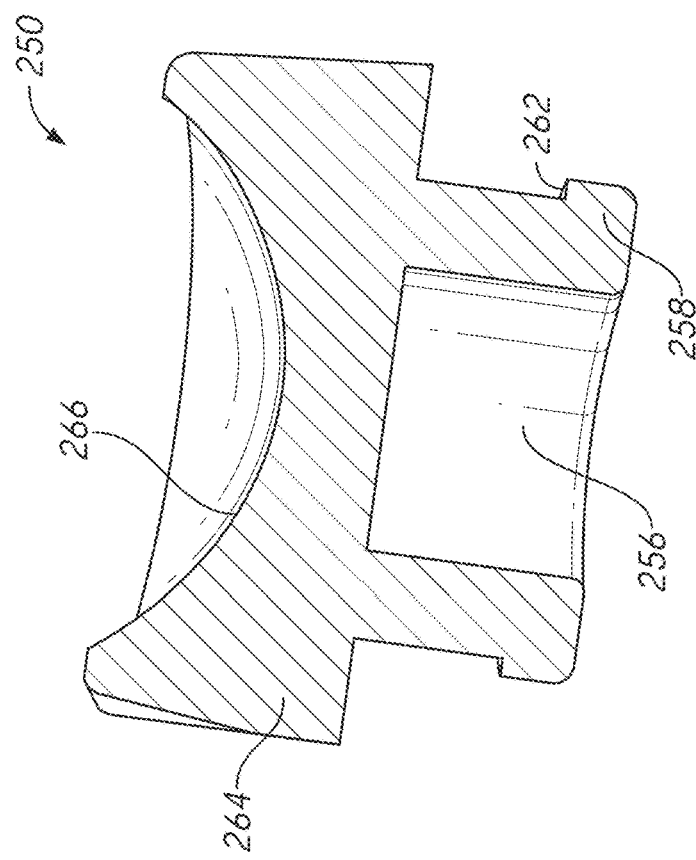
FIG. 15 is a cross-sectional view of the reverse articular body shown in FIG. 14 taken at section plane 15-15.
Figure 14:
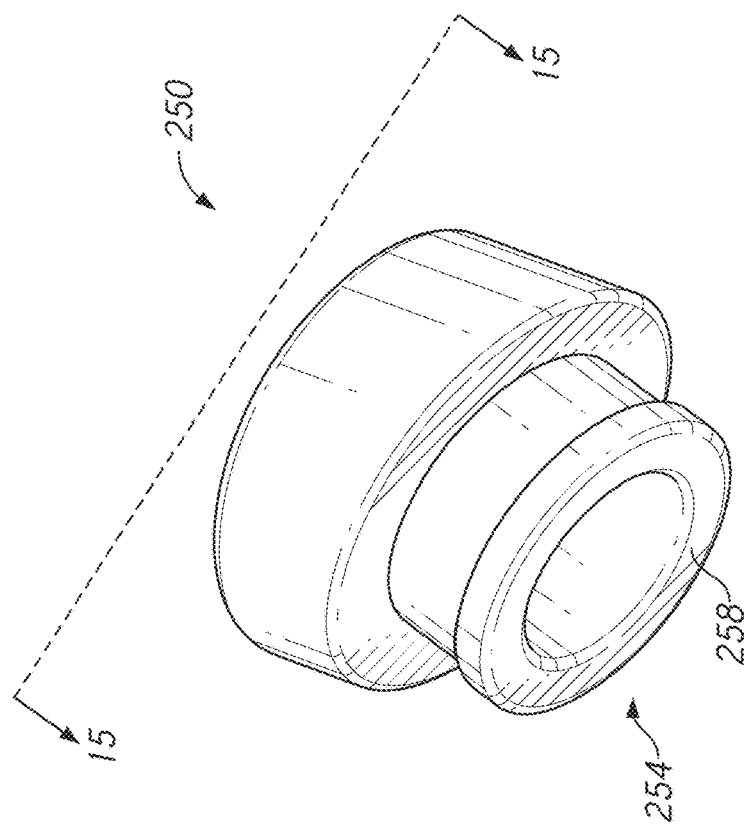
FIG. 14 is an inferior perspective view of the reverse articular body shown in FIG. 2.

FIGS. 12-15 show different combinations of the humeral stem 100 and various articular bodies. FIG. 12 show an anatomic articular body 200 coupled with the humeral stem 100. The anatomic articular body 200 includes a tapered projection 204 that is configured to mate with the inside surface 122a disposed about the mounting hole 116. The tapered projection 204 has a tapered profile that create an interference fit, e.g., a Morse taper, with a tapered profile of the inside surface 122a.

For certain patients there is a need to convert the anatomic assembly of FIG. 12 to a reverse assembly of FIG. 2. The anatomic articular body 200 can be removed by a convention technique such as by prying the anatomic articular body 200 off of the inner wall 122 of the humeral stem 100. After the mounting end 112 has been exposed by removing the anatomic articular body 200, a reverse articular body 250 illustrated in FIGS. 14 and 15 can be coupled with the mounting end 112 of the humeral stem 100. The reverse articular body 250 can include an annular projection 254 which is shown schematically in FIGS. 8-10. The annular projection 254 surrounds a space 256 formed in the reverse articular body 250. The space 256 is configured to receive the inner wall 122 when the reverse articular body 250 is coupled with the locking mechanism 160. The annular projection 254 includes an inferior facing taper 258. The inferior facing taper 258 is configured to engage the flexible flanges 162 to deflect the flexible flanges 162 away from the inner wall 122 and toward the outer wall 121. The reverse articular body 250 includes a superior body 264 that is disposed superiorly of the annular projection 254. The superior body 264, on one side, encloses the superior end of the space 256. The superior body 264, on the opposite side provides an articular surface 266 to engage a glenosphere in a reverse shoulder assembly.

C. Method of Implanting Stem With Patient Specific Metaphysis

Figure 16:
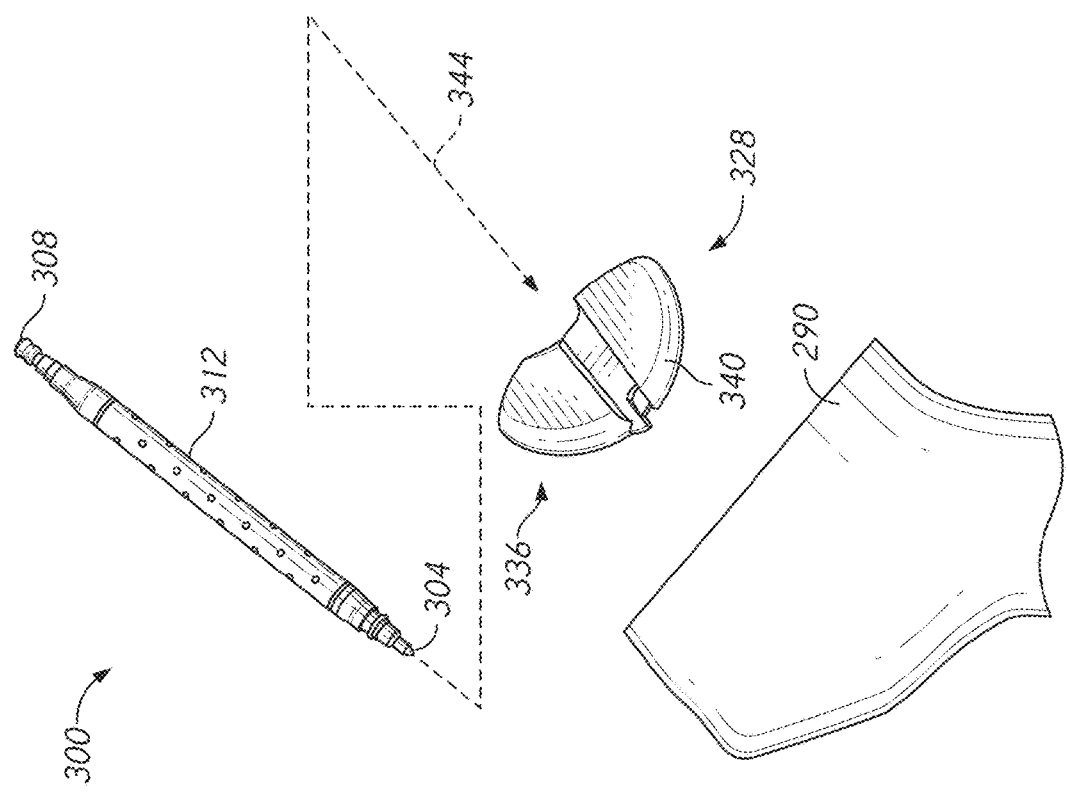
FIG. 16 is a schematic view of a step of a method of implanting a humeral stem according to the present application.
Figure 17:
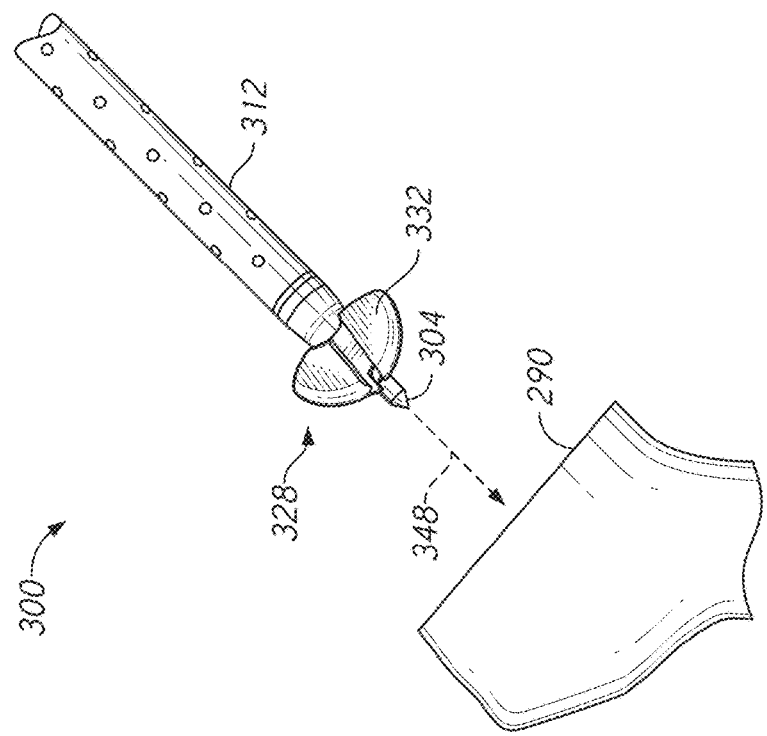
FIG. 17 is a schematic view of a step of the method of implanting a humeral stem following the step of FIG. 16.
Figure 18:
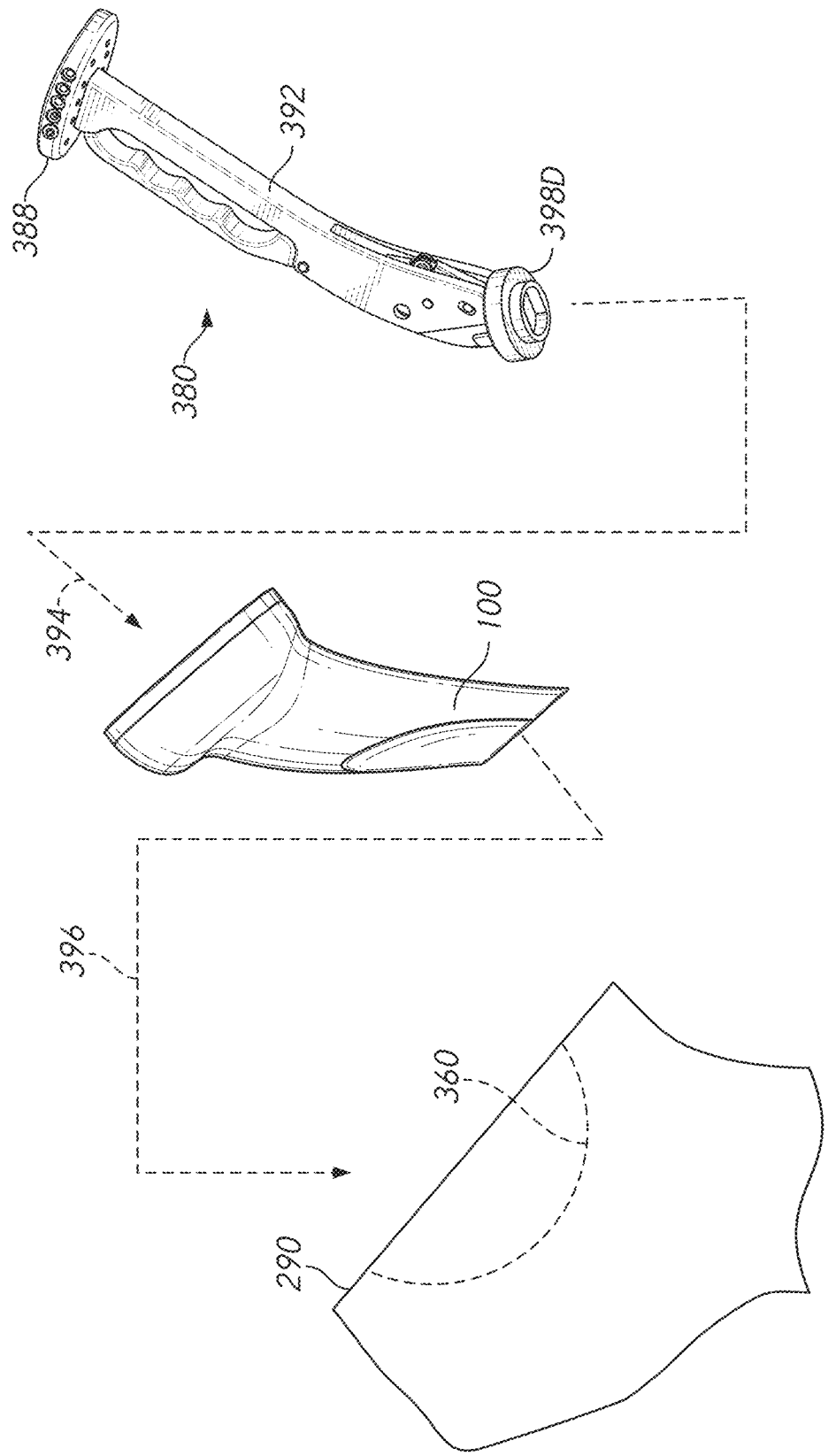
FIG. 18 is a schematic view of a step of the method of implanting a humeral stem following the step of FIG. 17.

FIGS. 16-18 show steps that can be performed in a method of implanting a humeral stem, e.g., a patient specific variation of the humeral stem 100. Prior to the steps illustrated in FIGS. 16-18 the humerus 12 can be resected in a convention manner. In some cases, the humerus 12 can be resected using a patient specific guide to cause the resection plane 290 to be in a specific location along the length of the humerus 12. Another aspect of these methods that can be patient specific is the preparation of the humerus 12 to receive the humeral stem 100.

FIG. 16 shows a reamer head 328 that can be coupled with a reamer shaft 300 in a process for forming the bone inferior of the resection plane 290. The reamer head 328 can be made patient specific to form a concave recess in the humerus 12 inferior of the resection plane 290. For example 3D imaging of the humerus 12 can be obtained. An appropriate configuration of the humeral stem 100 can be determined based upon the 3D imaging. For example, the metaphyseal shape 140 can be determined based on an analysis of the shape, volume, and bone quality of the humerus 12. In one example the metaphyseal shape 140 can include an outer, inferior surface of the mounting end 112. The outer, inferior surface of the metaphyseal shape 140 can be at least partially spherical.

A spherical surface of the metaphyseal shape 140 of the humeral stem 100 can be mirrored in the reamer head 328. For example, the reamer head 328 can include an outer surface, e.g., an exterior reaming surface 332, configured for reaming the cancellous bone inferior of the resection plane 290 of the humerus 12. The reamer head 328 can have a patient specific feature 336, in one embodiment the reamer head 328 can have a patient specific curvature 340. The radius of curvature of the reamer head 328 can match a desired radius of curvature of a patient specific recess 360. The reamer head 328 includes an aperture through which a first end 304 of the reamer shaft 300 can be inserted. FIG. 16 shows that the first end 304 can be inserted into the reamer head 328 and through the channel as indicated by the arrow 344. Thereafter the reamer head 328 can be secured to the first end 304. The reamer head 328 can be secured to the first end 304 such that the reamer head 328 can be rotated by the reamer shaft 300. In some methods, a second end 308 of an elongate body 312 of the reamer shaft 300 can be secured to a driver configured to rotate the elongate body 312 and to thereby rotate the reamer head 328. Such rotation can be performed while at the same time advancing the reamer shaft 300 and the reamer head 328 along the direction indicted by the arrow 348. Further advancement of the reamer shaft 300 and the reamer head 328 along the arrow 348 causes the cancellous bone to be removed. As a result a patient specific recess 360 is formed in the resection plane 290 of the humerus 12.

In one method the humeral stem 100 can be advanced into the humerus 12 at the resection plane 290. The humeral stem 100 can be advanced by securing a stem holder 380 to the humeral stem 100. The stem holder 380 can include a first end 384 and a second end 388. The first end 384 can be configured to mate with a portion of the mounting end 112. The first end 384 has a stem interface 398D configured to secure to the mounting end 112 of the humeral stem 100. The second end 388 can have a surgeon interface such as a handle that can be actuated to grasp and, later, release the grasp of the mounting end 112 of the humeral stem 100. The stem holder 380 includes an elongate body 392 enabling the surgeon to hold the humeral stem 100 remotely of the joint space and remotely of the humerus 12.

In one method, the stem holder 380 is advanced as indicated by the arrow 394 to position the first end 384 in the mounting end 112. The second end 388 can be actuated to engage a coupler 398A including the stem interface 398D if the coupler is removable from the stem holder 380. The stem holder 380 can have a stem interface 398D at the first end 384 for connection to the mounting end 112 of the humeral stem 100. The second end 388 can be manipulated to move the elongate body 392 and the humeral stem 100 as indicated by the arrow 396 to move the humeral stem 100 into the humerus 12. As indicted by the head of the arrow 346 the humeral stem 100 can be directed into the humerus 12 along a longitudinal axis of the humerus 12. FIG. 18 shows that the bone inferior of the patient specific recess 360 can be un-prepared. In other words, contrary to common practice further steps of preparing the interior of the humerus 12 inferior of the reamed area are not needed. For example, even though the humeral stem 100 includes the hollow shaft 104 the humeral stem 100 does not require a connection be made to the intramedullary canal of the humerus 12.

Rather, the sharp inferior edge 108 of the humeral stem 100 is configured to create access as it is being advanced into the cancellous bone. The sharp inferior edge 108 cuts a pathway for the humeral stem 100 into the interior of the humerus 12.

Figure 18A:
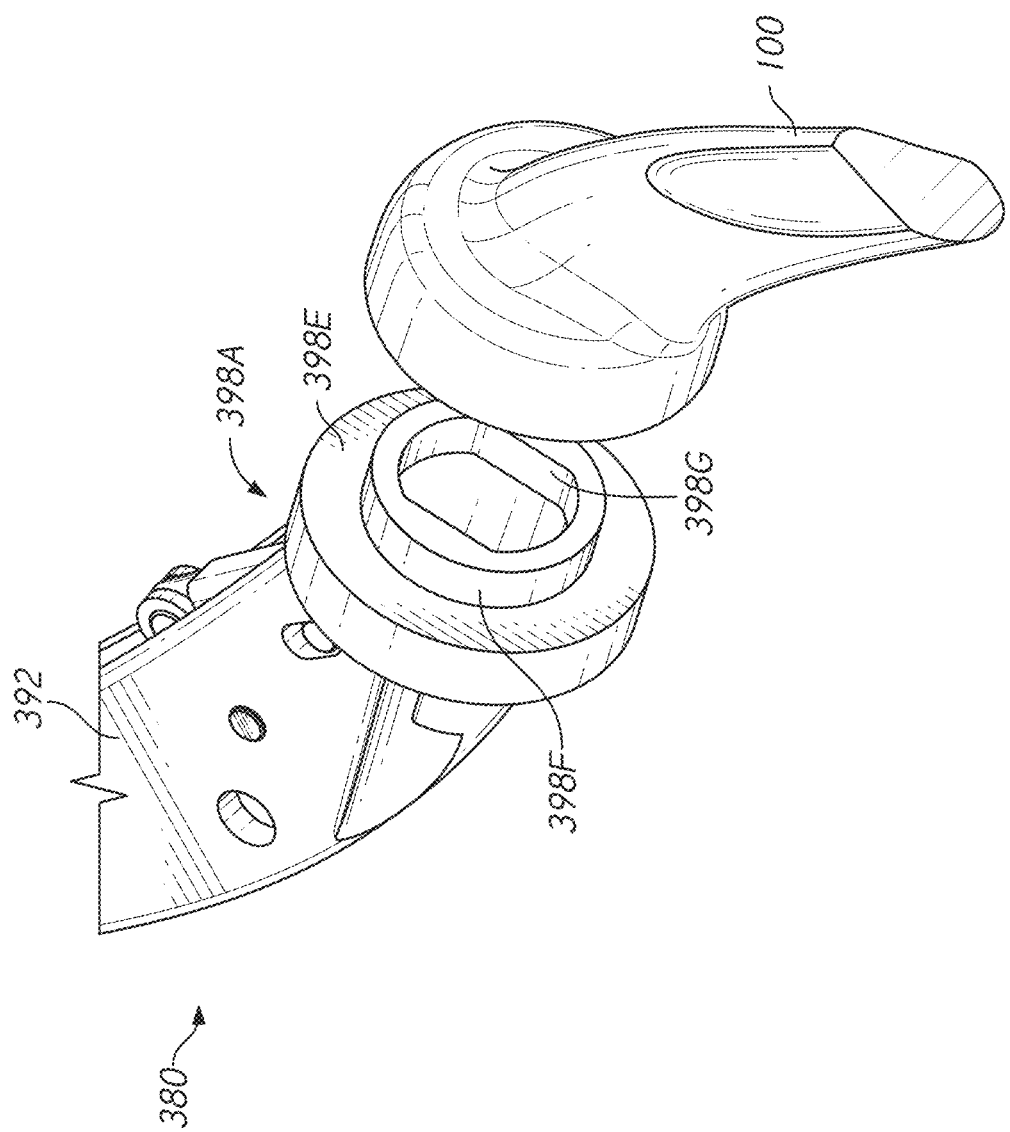
FIG. 18A is an exploded view of a humeral stem and a stem holder with a removable coupler for handling a humeral stem from a superior perspective.
Figure 18C:
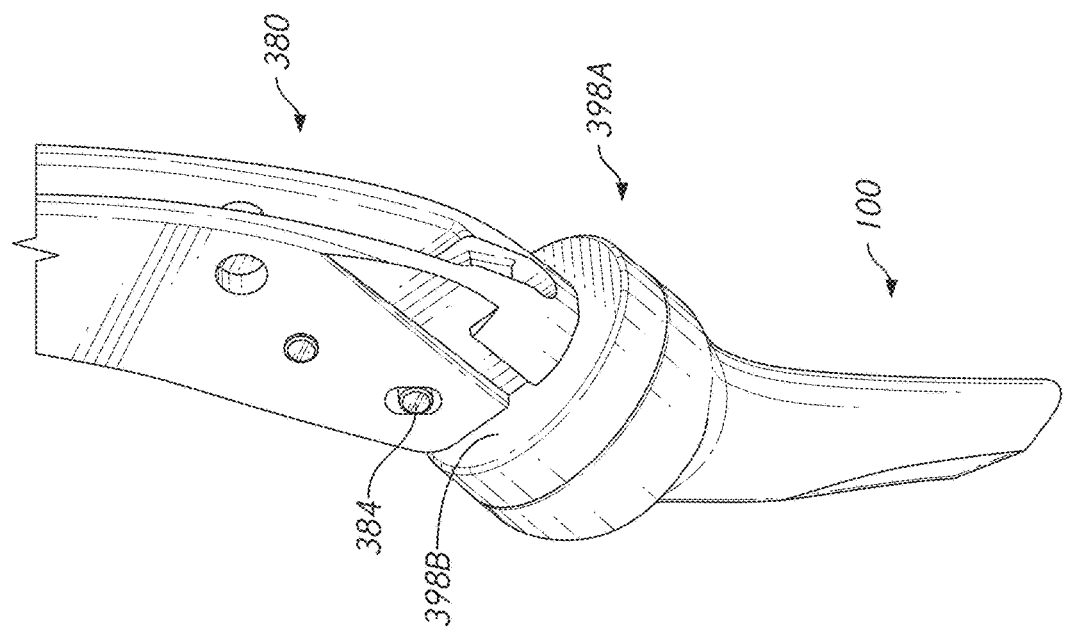
FIG. 18C is an assembled view of the humeral stem and the stem holder with the removable coupler shown in FIG. 18A.
Figure 18B:
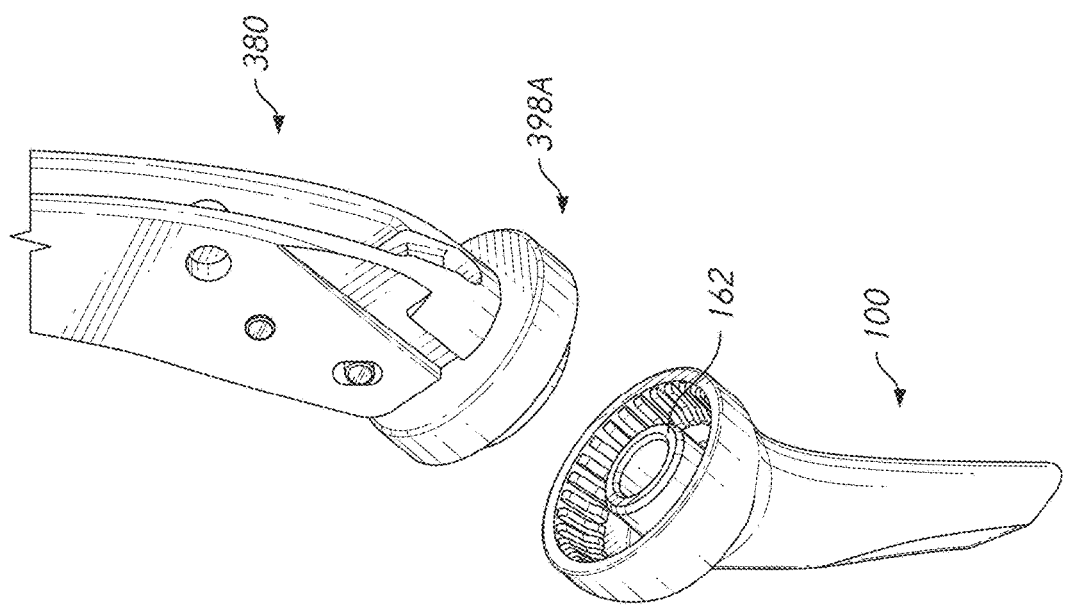
FIG. 18B is an exploded view of a humeral stem and a stem holder with a removable coupler for handling a humeral stem from an inferior perspective.

FIGS. 18-18C show various aspects of embodiments of the stem holder 380 and the coupler 398A, which can be removable. FIG. 18C shows that removable coupler 398A includes a superior end 398B that is configured to be coupled with the stem holder 380. The superior end 398B can include a tooling interface 398C. In one embodiment, the tooling interface 398C includes two apertures that are oriented away from each other. The stem holder 380 can have at the first end 384 prongs corresponding to the apertures. The prongs can be actuated to move into and out of engagement with the apertures in the tooling interface 398C of the removable coupler 398A.

FIG. 18A shows that the removable coupler 398A can have an annular projection 398E as part of the tooling interface 398C. The annular projection 398E can include an outer surface 398F and an inner surface 398G. The outer surface 398F can be configured to be received into the mounting end 112 such that the outer surface 398F is disposed within superior portions of the flexible flanges 162 by advancing the stem holder 380 as indicated by the arrow 394 (see FIG. 18). The outer surface 398F can be sized such that the diameter or width of the outer surface 398F is larger than the undeflected configuration of the flexible flanges 162 (e.g., as shown in FIG. 8). The outer surface 398F can be sized to deflect the flexible flanges 162 when received therein to the configuration shown in FIG. 9. The outer surface 398F preferably lacks a structure similar to the superior facing taper 262 in the annular projection 254 (See FIG. 10) such that the removable coupler 398A is not trapped inferior to the inferior edge of the flexible flanges 162. The outer surface 398F is sized such that when received in the flexible flanges 162 with the flexible flanges 162 in the deflected state friction between the flexible flanges 162 and the outer surface 398F securely holds the humeral stem 100 to the removable coupler 398A but does not prevent removal of the removable coupler 398A from the mounting end 112 of the humeral stem 100.

The inner surface 398G of the removable coupler 398A is sized to receive or not interfere with the inner wall 122. When the annular projection 398E is advanced into the mounting end 112 the annular projection 398E is disposed between the outer wall 121 and the inner wall 122. Thus the width of the annular projection 398E is less than the distance between the radially inward facing surface of the outer wall 121 and the radially outward facing surface of the inner wall 122. As noted above, the coupler 398A can be removable such that the stem holder 380 can be used with other types of stem or stemless humeral anchors. The coupler 398A can in other embodiments be part of the first end 384 of the stem holder 380 and not removeable from the inferior portions of the stem holder 380.

Although the humeral stem 100 can be patient specific, e.g., comprising a patient specific metaphyseal shape 140, the interior surface of the mounting end 112 can be generic. Accordingly, the coupler 398A can be generic to many or all patients. For example, even if the size and/or the shape of the humeral stem 100, e.g., the metaphyseal shape 140, is made patient specific, the size and/or the shape of the annular projection 398E can be the same for some or all humeral stems 100. The outer surface 398F can have a diameter that matches an inner diameter of the humeral stem 100, which can be generic to all patients even as portions of the humeral stem 100 to be disposed beneath the resection plane 290 are made patient specific.

The foregoing apparatuses, systems, and methods together enable placement of the humeral stem 100 in the humerus 12 with minimal tools and steps. Also, due to the patient specific nature of one or more aspects of the humeral stem 100 the stem provides excellent fit in the humerus 12 even under the streamlined process described above.

D. Patient Specific Shoulder Joint Implantation Kit

Figure 19:
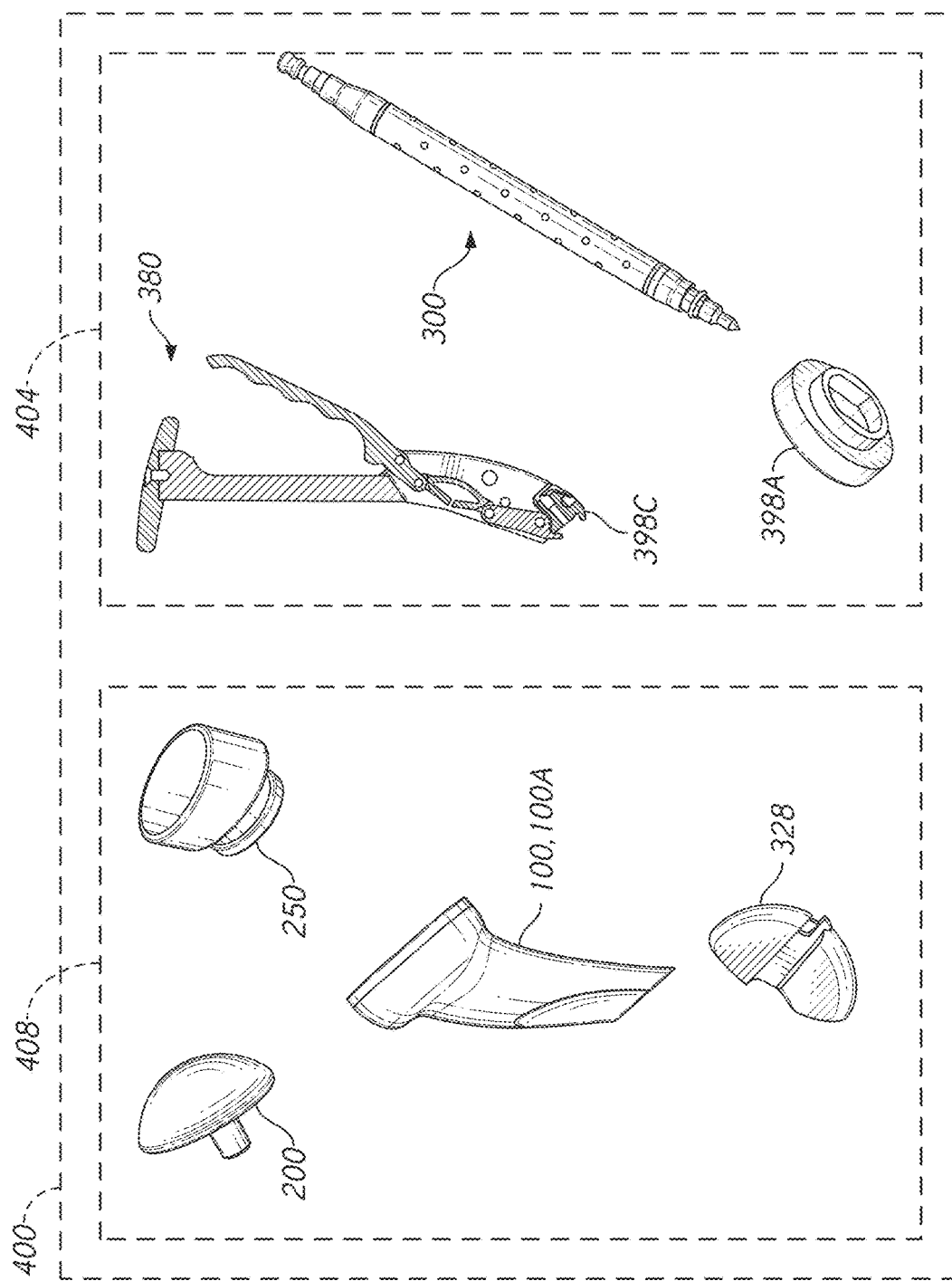
FIG. 19 illustrates various kits according to the present application.

FIG. 19 shows a kit 400 that includes various inventive components combined in inventive ways. The kit 400 includes a surgical kit 404 and a patient kit 408 in one embodiment. The surgical kit 404 can be used for more than one patient. The surgical kit 404 can include, among other components the reamer shaft 300 and the stem holder 380. These components of the surgical kit 404 can be configured for refurbishment and re-use.

The patient kit 408 can be a patient specific kit. The patient kit 408 can include the humeral stem 100 which can be made patient specific in one more aspects. The patient kit 408 can also include the reamer head 328. The reamer head 328 can be made patient specific in one or more aspects. For examples, Current surgical techniques for shoulder articulation replacement include several successive steps including reaming the humeral head, making an entry into the bone, preparing the bone including punching, compacting, fixing an implant, protecting the implant, making a trial articulation mounting and mounting the final implant. This results in a longer and more costly procedure than necessary. Moreover, the known techniques which use patient specific implants or ranges of implants also need patient specific or ancillary tools such as rasps, drills and cutting guides, whose manufacturing and shipping is costly.

A goal of the invention is to provide a new surgical method for shoulder articulation replacement which is more simple, and less costly than the techniques of the prior art.

III. Patient Specific Reverse Shoulder Implant

The foregoing embodiments can be made patient specific in some cases. Patient specific shoulder implants can improve the performance and the longevity of a shoulder replacement. In some cases, it is desirable to provide a reverse shoulder assembly that is not only patient specific in a single aspect but can be made specific and appropriate for a specific patient in a number of relevant aspect. Section III(A) discusses various methods for providing a patient specific reverse should joint humeral implant. Section III(B) discusses various examples of features of reverse should joint humeral implants that can be arranged in a patient specific manner. These sections are relevant to the humeral implants disclosed herein above and claimed herein.

A. Method of Providing Manufacturing Reverse Shoulder Assemblies

Figure 20:
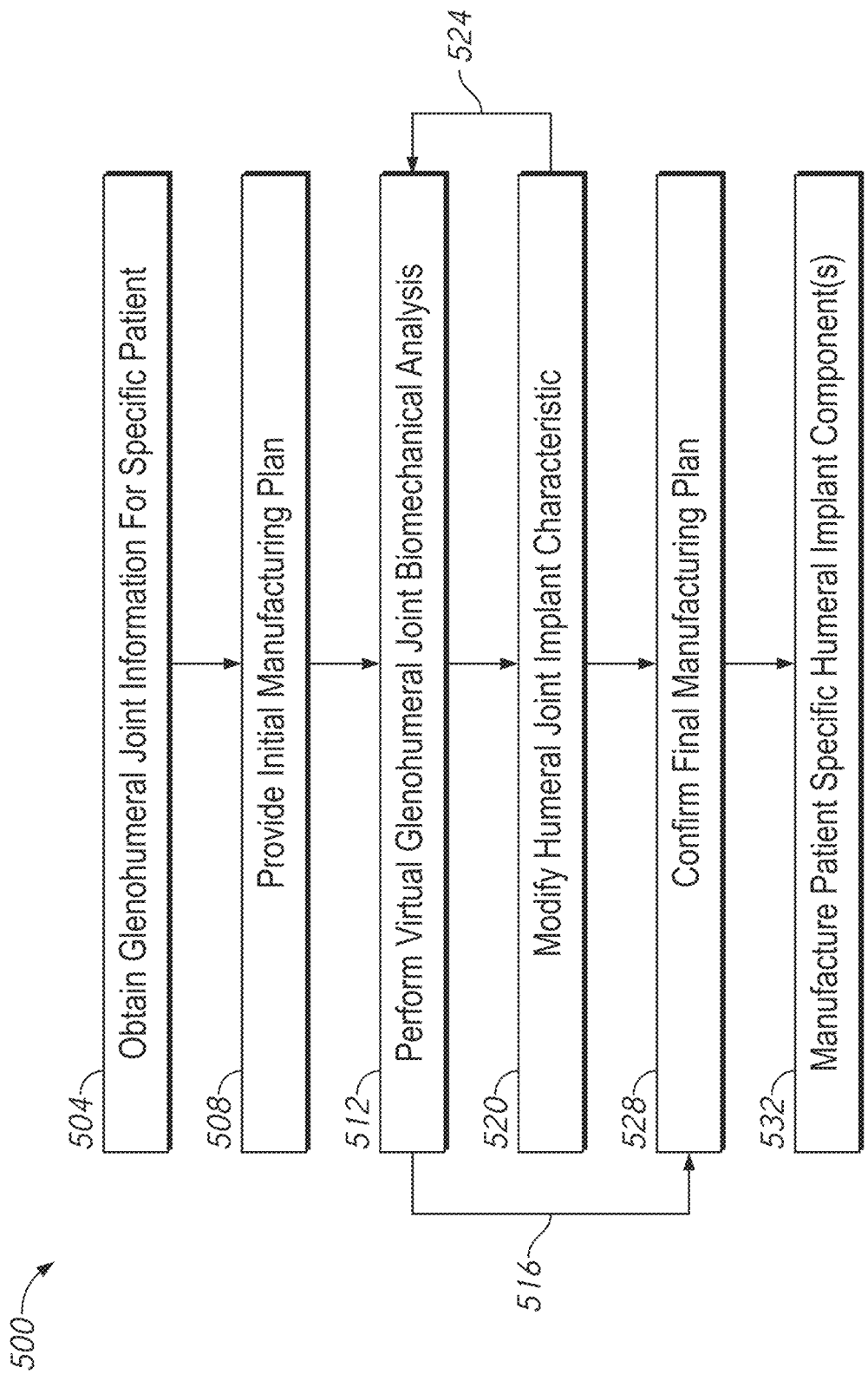
FIG. 20 is a flow chart illustrating a method of manufacturing at least a part of a humeral implant.

FIG. 20 shows a method 500 of providing a humeral implant. The method 500 can be directed to providing a reverse shoulder humeral implant. The reverse shoulder humeral implant can be similar to those discussed above, e.g., to the humeral implant 90 which includes the hollow humeral stem 100. The method 500 can be used to form a solid humeral anchor or stem as discussed below. The method 500 can be used to form other anchors. stems, articular bodies and other shoulder assembly components as well.

In an early portion of one embodiment of the method 500, a step 504 is performed in which glenohumeral joint information of a specific patient is obtained. Glenohumeral joint information can be obtained by any imaging modality, such as MRI, CT scan, Xray or other imaging techniques. Glenohumeral joint information can include a wide range of information, such as the size, shape and form of the humerus, the size, shape and form of the glenoid. Glenohumeral joint information can include the relative positions of portions of the humerus (e.g., the greater trochanter, the lesser trochanter, or other prominent landmarks), of portions of the scapula (e.g., the glenoid, the acromion, or other prominent landmarks), and of portions of other bone portions around the shoulder.

Figure 20A:
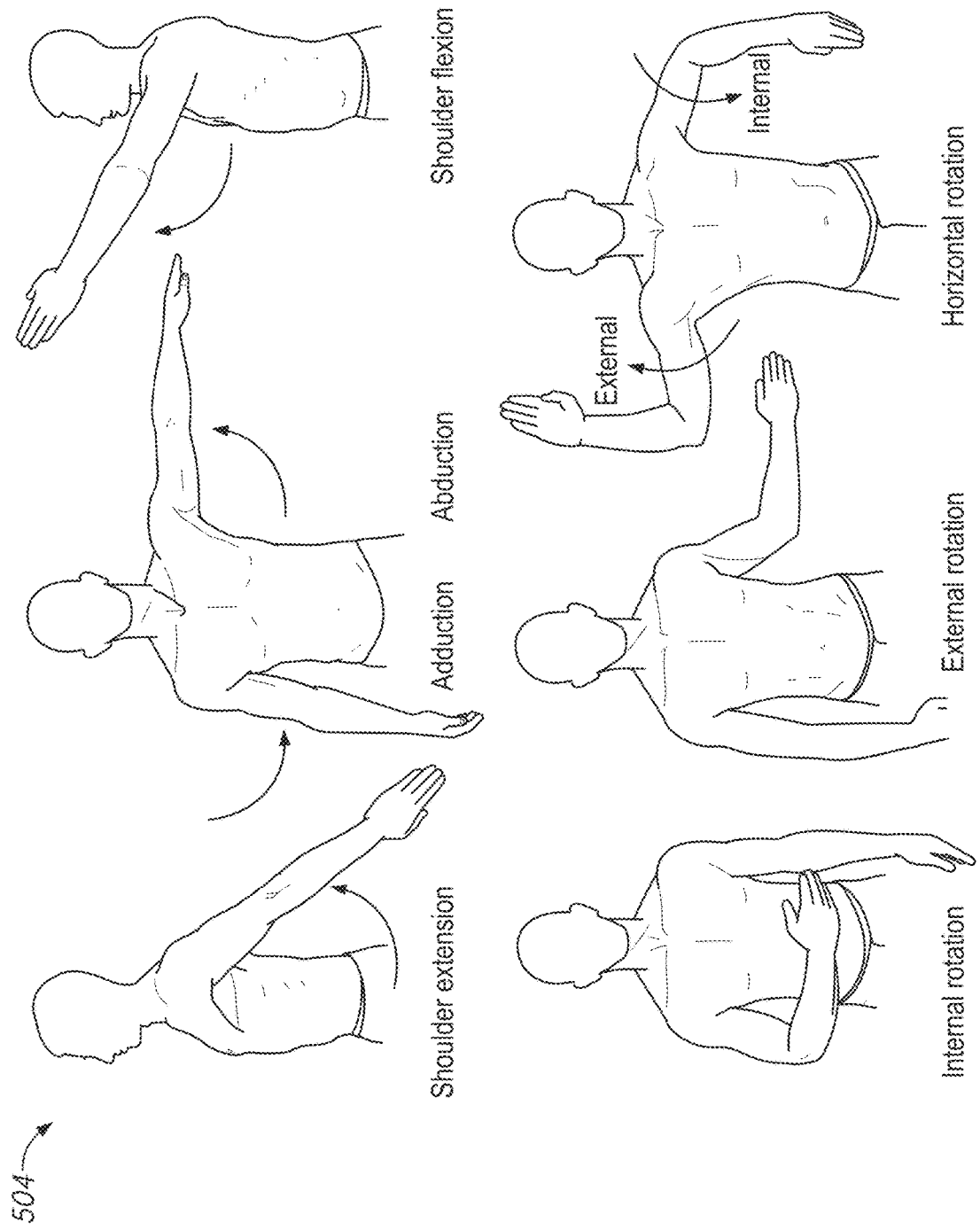
FIG. 20A is a schematic view showing how glenohumeral joint information can be obtained and aspects of biomechanical analyses that can be performed.

Glenohumeral joint information can include range of motion analysis. FIG. 20A shows an example of various forms of range of motion analysis that can be included in the step 504. For example, the patient can be instructed to move an arm of an affected shoulder joint to provide shoulder extension. The amount of extension, e.g., the angle between the arm and the medial-lateral-vertical plane of the body, can be determined. The patient can be instructed to move an arm of an affected shoulder joint to provide shoulder abduction and/or adduction. The amount of abduction, e.g., the angle between the arm and the anterior-posterior-vertical plane of the body, can be determined. The patient can be instructed to move an arm of an affected shoulder joint to provide shoulder flexion. The amount of flexion, e.g., the angle between the arm and the medial-lateral-vertical plane of the body, can be determined. The patient can be instructed to move an arm of an affected shoulder joint to provide shoulder internal or external rotation. The amount of internal or external rotation, e.g., the angle swept by the hand moving from a neutral position internally or from a neutral position externally can be determined. The patient can be instructed to move an arm of an affected shoulder joint to provide shoulder horizontal rotation. The amount of horizontal rotation, e.g., the angle swept by the hand moving upward or downward from a laterally extended horizontal position can be determined. FIG. 20A illustrates just some aspects of range of motion analysis that can be included in the step 504. For example, range of motion analysis can also be performed at least partially virtually to determine a desired range of motion based on the glenohumeral joint information (e.g., in step 512 described below). A virtual analysis can be performed iteratively with obtaining glenohumeral joint information in step 504.

Glenohumeral joint information can include interactions among, e.g., impingements between, the bones, among components coupled with the bones, or among a component coupled with one bone and a bone portion opposite the component following implantation.

Glenohumeral joint information can include an analysis of tension in soft tissues. For example, the humerus and the scapula are held in adjacency by soft tissues, e.g., muscles, tendons, ligaments and other soft tissues.

The method 500 can proceed to a step 508 in which an initial manufacturing plan is provided. The initial manufacturing plan can be based on a subset of glenohumeral joint information. For example, the step 508 can provide a manufacturing plan that sets the general size and shape of a component of the humeral implant 90 or another humeral implant. The step 508 can provide a manufacturing plan that sets the general size and shape of the humeral stem 100 or of a solid humeral anchor as discussed below in connection with FIGS. 21-29. The step 508 can involve providing an initial manufacturing plan to a surgeon preforming a pre-operative analysis of the patient to assess the proper shoulder implant arrangement. The step 508 can involve providing an initial manufacturing plan to a display for a user to evaluate the initial manufacturing plan.

Figure 20B:
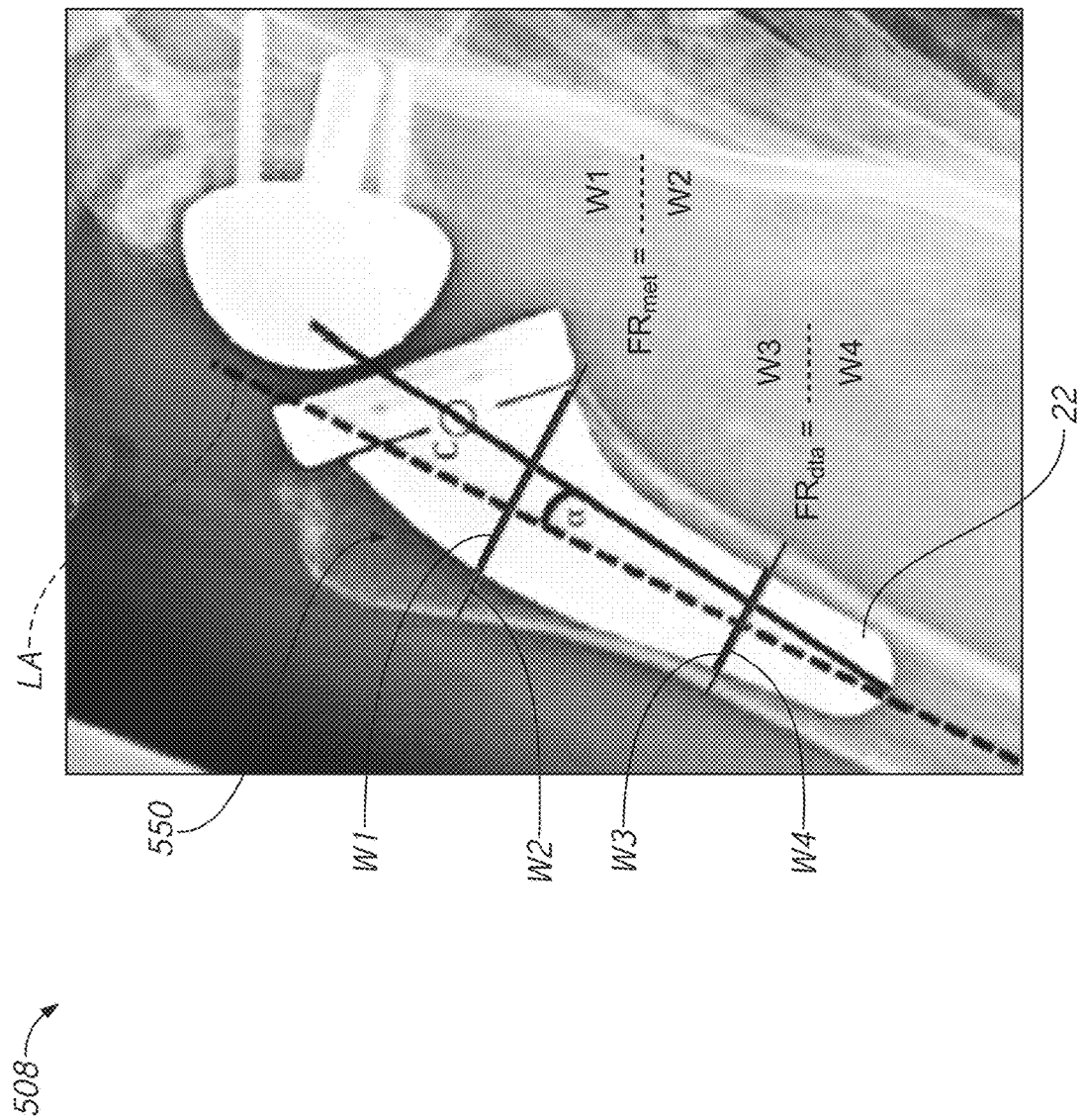
FIG. 20B shows analyses that can inform definition of an initial or final manufacturing plan.

FIG. 20B shows an example of some of the analyses that can be conducted to provide an initial manufacturing plan according to the step 508. The size of a humerus 12 can be determined as a width transverse to a central longitudinal axis LA of the humerus 12 and a size of a humeral anchor 550 can be determined accordingly. In one embodiment the step 508 determines a first width W1 with reference to a second width W2. The second width W2 can be the width of the humerus 12 in a metaphysis portion of the humerus. The Second width W2 can be found at a location superior to the neck of the humerus 12. The second width W2 can be measured form one edge of a resection plane of the humerus 12 to an opposite lateral cortical surface of the humerus 12. The first width W1 can be chosen in the initial manufacturing plan according to step 508 to not exceed a metaphysis filling ratio $FR_{met}$ which can be calculated as the ratio of first width W1 to second width W2 as shown. Preferably the metaphysis filling ratio $FR_{met}$ does not exceed 0.95 in some embodiments, does not exceed 0.9 in some embodiments does not exceed 0.85 in some embodiments, does not exceed 0.8 in some embodiments, does not exceed 0.75 in some embodiments, does not exceed 0.7 in some embodiments. The metaphysis filling ratio $FR_{met}$ preferably is in a range of 0.5 to 0.95 in some examples. The metaphysis filling ratio $FR_{met}$ preferably is in a range of 0.6 to 0.9 in some examples. The metaphysis filling ratio $FR_{met}$ preferably is in a range of 0.7 to 0.85 in some examples.

The size of a diaphysis portion of the humeral anchor 550 can also be specified in an initial manufacturing plan during the step 508. A third width W3 can be defined in the diaphysis region of the humeral anchor 550. The third width W3 can be measured transverse to a longitudinal axis of the humeral anchor 550 at a location spaced form the inferior end o the humeral anchor 550. The third width W3 can be initially selected during the step 508 as part of the initial manufacturing plan as a function of the bone of the humerus 12. For example, the diaphysis portion of the humerus 12 can have a fourth width W4 transverse to the central longitudinal axis LA of the humerus 12. The fourth width W4 can be measured at a location where the portion of the humeral anchor 550 intended to come to rest at the location of the measurement of the fourth width W4 is the portion having the third width W3. A diaphysis filling ratio $FR_{dia}$ can be defined as a ratio of the third width W3 to the fourth width W4. The third width W3 can be chosen in the initial manufacturing plan according to step 508 to not exceed a selected diaphysis filling ratio $FR_{dia}$ Preferably the diaphysis filling ratio $FR_{dia}$ does not exceed 0.95 in some embodiments, does not exceed 0.9 in some embodiments does not exceed 0.85 in some embodiments, does not exceed 0.8 in some embodiments, does not exceed 0.75 in some embodiments, does not exceed 0.7 in some embodiments. The diaphysis filling ratio $FR_{dia}$ preferably is in a range of 0.5 to 0.95 in some examples. The diaphysis filling ratio $FR_{dia}$ preferably is in a range of 0.6 to 0.9 in some examples. The diaphysis filling ratio $FR_{dia}$ preferably is in a range of 0.7 to 0.85 in some examples.

Other aspects of size and form can also be determined for at least one component of a humeral implant, such as the humeral implant 90. FIG. 20B shows that the humeral anchor 550 can be shaped to have an angular or an arcuate form. The superior portion can be disposed more medially than the inferior portion thereof when applied to the humerus 12. The outer surfaces can be curved. One measure of the degree of curvature of the humeral anchor 550 is an angle α as measured between the central longitudinal axis LA and a line L1 connecting a center of an inferior tip of the humeral anchor 550 and the geometric center C of a superior face of the humeral anchor 550. The greater the angle α the more medially spaced the superior face is from the inferior tip. The greater the angle α the closer the superior face of the humeral anchor 550 is to the cortical bone at the resection surface of the humerus 12. By minimizing exposed cancellous bone at the medial calcar the humeral anchor 550 can reduce, minimize or eliminate the chance for stress shielding at the medical calcar.

FIG. 20C shows other aspects of the method 500. The bones of an affected shoulder joint of a specific patient can be evaluated as part of obtaining glenohumeral joint information in the step 504 to determine how close the humerus 12 (or some portion thereof) is to the scapula 14 (or some portion thereof). For example a bone spacing S1 can be determined between the greater tuberosity 22 of the humerus 12 and the acromion 20 of the scapula 14. The bone spacing S1 gives a sense for the condition of the soft tissue tensioning the shoulder joint. This is just one example of a metric that can be used to assess the bones from preoperative imaging. FIG. 20C can also inform the step 508. Specifically, it may be determined that the bone spacing S1 suggests that to achieve improved soft tissue tensioning the humeral anchor 550 should be able to put more tension on the soft tissue given an anticipated location of a glenosphere in the bone. Then, the imaging illustrated in FIG. 20C can automatically or by the surgeon's selection begin the method 500 with a humeral anchor 550 having a greater thickness metaphysis portion, as discussed further below.

Figure 20D:
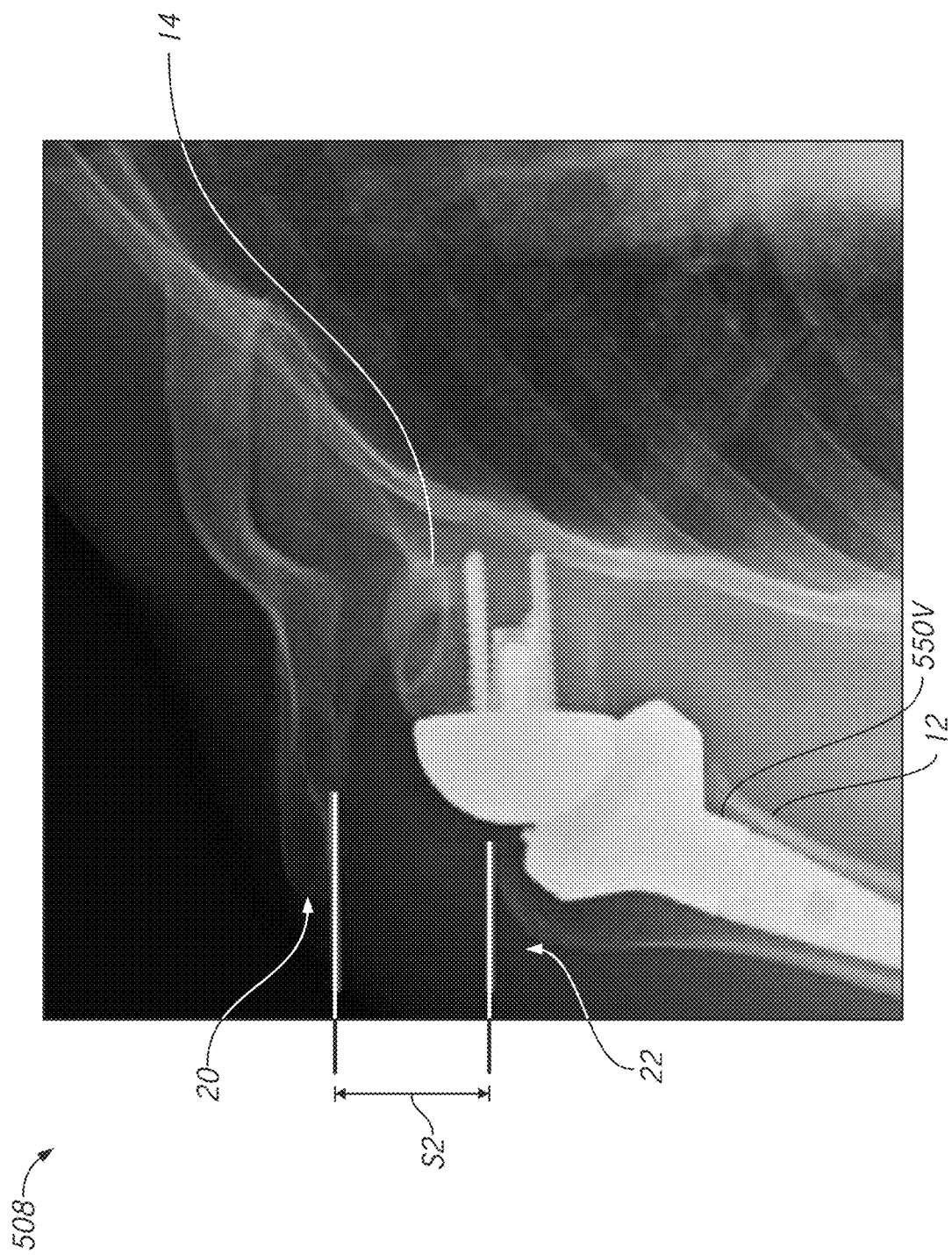
FIG. 20D is an example of a virtual model that can be used in the process of generating a final manufacturing plan.

The step 508 can involve providing an initial manufacturing plan to software able to create a virtual model of a specific patient's shoulder based on the step 504 of obtaining glenohumeral joint information. FIG. 20D shows an example of a virtual model. The model can include models of the humerus 12 and the scapula 14 and relevant portions thereof such as the greater tuberosity 22 and the acromion 20. Virtual components such as a virtual humeral anchor 550V can be constructed in the model to enable the method 500 to generate an initial and/or a final manufacturing plan. The manufacturing plan can take into account the bone spacing S2 that is desired as between relevant bone segments as a metric for suitable soft tissue tensions. The manufacturing plan can take into account the spacing S2 that is desired as between a bone segment and a component of shoulder implant to reduce, minimize or eliminate bone impingements that could lead to notching.

FIG. 20 shows that a step 512 involves performing a virtual glenohumeral joint biomechanical analysis. Software can modify one or all of a variety of parameters discussed below in connection with FIGS. 21-31 and more. The step 512 can confirm that the initial manufacturing plan provided in the step 508 is appropriate for a specific patient. An arrow 516 shows that if the initial manufacturing plan is confirmed one or more steps of the method 500 can be skipped. The arrow 516 shows that a step 528 can directly follow the step 512 in some embodiments, where the initial manufacturing plan provided in the step 508 is confirmed in the step 528.

In some variations and for some patients, the initial manufacturing plan provided in step 508 is not appropriate for the specific patient. As a result the method 500 involves modifying a humeral joint implant characteristic in a step 520. The step 520 can be followed as indicated by arrow 524 by repeating the step 512 in which virtual glenohumeral joint biomechanical analysis is performed on a manufacturing plan as modified from the initial manufacturing plan according to the step 520.

The step 512 can be performed in the same way in connection with the first modification of the initial manufacturing plan provided in the step 508 as provided in the step 520. In some cases the second instance of the step 512 following the modification of the initial manufacturing plan provided in step 508 is different potentially focusing on the aspect(s) that was or were modified.

The modification provided in the step 520 and the virtual analysis conducted in step 512 can be iterated as many times as beneficial for providing a well configured humeral implant.

An instance of the step 512 following the modification of the initial manufacturing plan concludes that a well configured virtual humeral implant has been identified. As a result the arrow 516 shows that the method 500 can follow to a step 528 in which a final manufacturing plan is confirmed. The final manufacturing plan provided in the step 528 can be provided in written or electronic form to enable humeral implant components to be made. The method 500 can follow to a step 532 in which one or more patient specific components can be manufactured.

During or after any step of the method 500, the method can include a step of outputting an indication to the user that a parameter that is selected or modified is selected or modified to provide a specific performance benefit, e.g., prior to or after the step 532.

As discussed further below the method 500 can be used to cause a humeral anchor, e.g., with a stem, or an articular body to be manufactured for a specific patient that is well configured for one or a number of characteristics of humeral joint implants.

B. Patient Specific Humeral Anchor Structures

As noted above, methods are disclosed herein for creating patient specific shoulder implants and components. The method can be used to create unique humeral anchor structures for specific patients in many different aspects.

1. Humeral Anchors with Patient Specific Inclination Angle Adjustments

Figure 21:
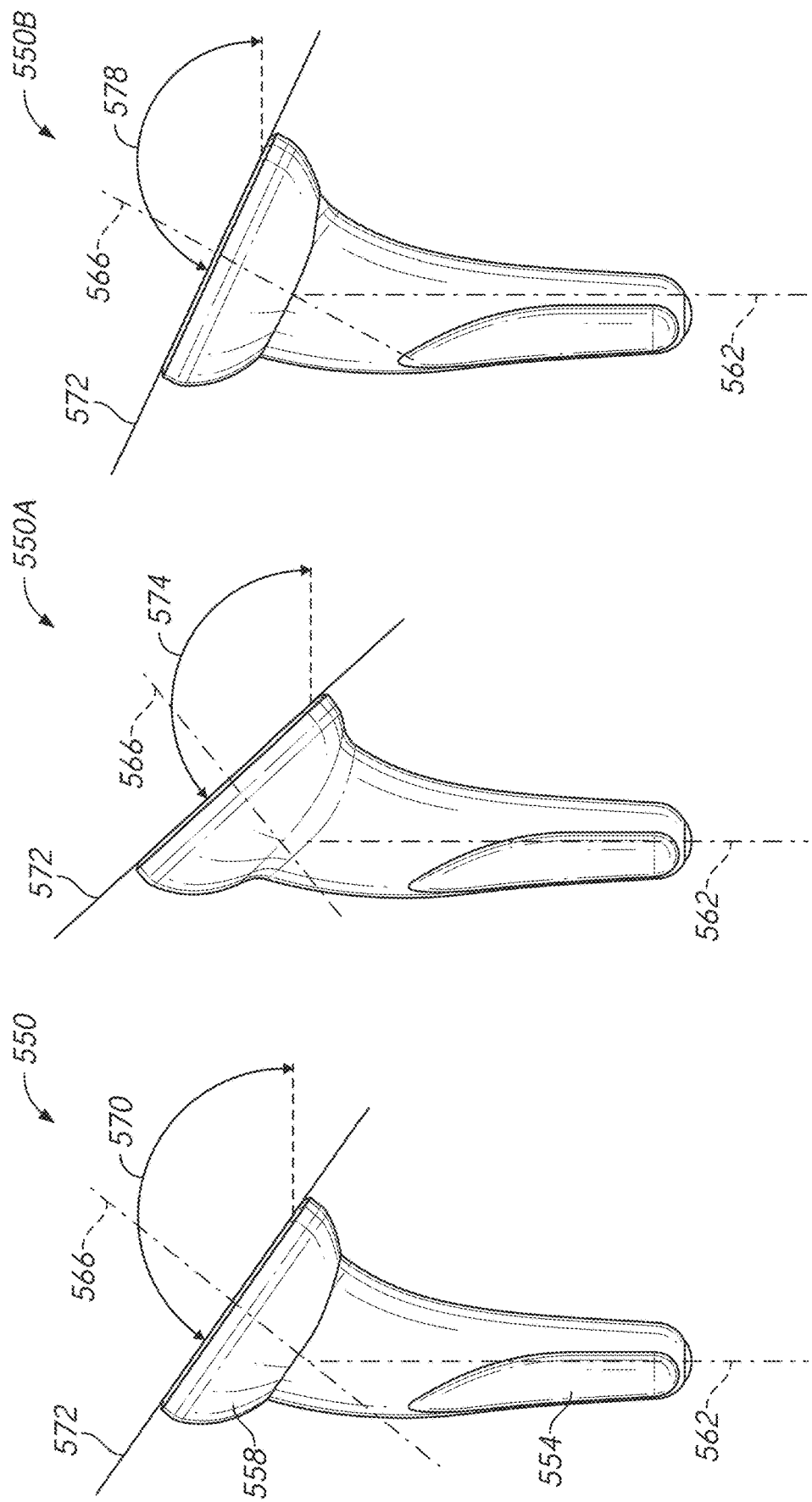
FIG. 21 is an anterior view of three embodiments of a humeral anchor, each having a different level of inclination.

FIG. 21 shows a humeral anchor 550 that can be applied to a patient at a superior humeral resection plane. The method 500 includes a stem portion 554 and a metaphysis portion 558. The stem portion 554 is located inferior of the metaphysis portion 558 when the humeral anchor 550 is applied to a humerus. The stem portion 554 comprises a generally slender member that can be sized as described above according to an analysis of the diaphysis portion of a humerus of a specific patient. The stem portion 554 can extend along a primary stem axis 562. The metaphysis portion 558 also can be similarly sized. As discussed in connection with the humeral stem 100 the metaphysis portion 558 can have a metaphyseal shape that is well suited for the metaphysis of the specific patient humerus. The metaphysis portion 558 can be oriented medially with a superior face extending transverse to a metaphyseal axis 566. An initial inclination angle 570 can be defined in at least two ways. The initial inclination angle 570 can be measured between a horizontal axis and an axis 572 dispose in the plane of the superior face of the metaphysis portion 558. The initial inclination angle 570 can also be defined as the angle between the primary stem axis 562 and the metaphyseal axis 566. In other case, the method 500 can proceed by defining the initial inclination angle 570 in the step 508. In one embodiment the initial inclination angle 570 is between 140 and 150 degrees, e.g., 145 degrees. The humeral anchor 550 can be defined to have the initial inclination angle according to the step 508 where a surgeon or a virtual analysis identifies the specific patient as benefiting from an initial reverse shoulder procedure. The step 512, the step 520, and the step 520 of the method 500 can modify the inclination angle upward or downward from this starting point for such patients. A surgeon or user of the method may modify the initial inclination angle to higher inclination angles to provide more stability of the implant in the humerus and less humeral lateralization. In some cases this is preferred even though taken alone the higher inclination angles may correspond to a higher risk of scapular notching. As discussed herein, scapular notching can arise from an articular body insert wearing on the scapula. The higher risk of notching arising from higher inclination angles can be countered by any of the other features herein that reduce notching risk, e.g., jump distance configurations. Lower inclination angles, e.g., reduced from an initial angle of 145 degrees in the step 520 can provide more humeral lateralization. Lower inclination angles can reduce the risk of scapular notching. Lower inclination angles may provide less stability, this potentially lower stability can be addressed by enhancing the humeral head filling configurations.

FIG. 21 shows that a humeral anchor 550A can be provided that has a reduced inclination angle 574. The reduced inclination angle 574 is reduced compared to the initial inclination angle 570. The reduced inclination angle 574 can correspond to a larger angle α as discussed above in connection with FIG. 20B. The reduced inclination angle 574 can be between 120 and 140 degrees, e.g., about 132.5 degrees. The humeral anchor 550A can be configured with these the initial inclination angle according to the step 508 where a surgeon or a virtual analysis identifies the specific patient as potentially needing a reverse shoulder revision procedure in the future, following an initial anatomic shoulder implant. The step 512, the step 520, and the step 528 of the method 500 can modify the inclination angle from this starting point and confirm the final manufacturing plan for such patients.

FIG. 21 also shows a humeral anchor 550B that includes an increased inclination angle 578. The increased inclination angle 578 is greater than that of the humeral anchor 550. The increased inclination angle 578 can be between 150 and 160 degrees, e.g., can be 155 degrees. The increased inclination angle 578 can correspond to a lesser angle α as discussed above in connection with FIG. 20B.

As discussed above, a wide range of flexibility can be provided form a plurality of starting points which can enable much improved fit for a specific patient based on pre-operative imaging. The result takes into account the specific patient's needs with regard to inclination angle and the specific patient anatomy, expedites the process by selecting among categories of patients such as leaving open the possibly of converting from anatomic to reverse or knowing that such conversion is not going to be useful. The result also simplifies the procedure by allowing the humeral anchor produced by the method 500 to have an inclination angle that well matches the humerus such that less resection and subsequent bone modification, e.g., reaming, is needed.

2. Humeral Anchors with Patient Specific Center of Rotation Offset Adjustment

Figure 22:
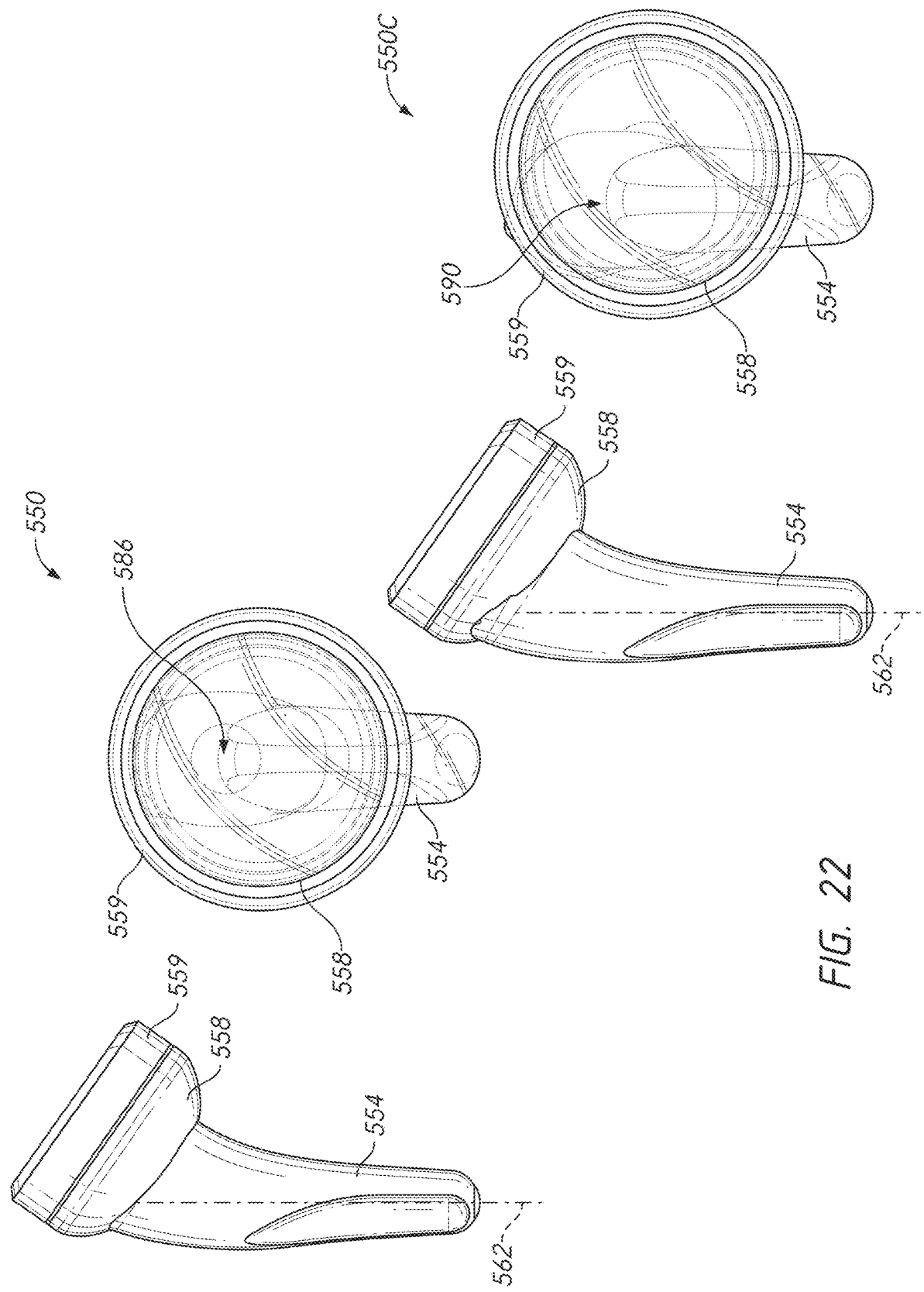
FIG. 22 includes anterior and superior views of two embodiments of humeral anchors with different levels of offset between a stem and a center of rotation of an articular body thereof.

FIG. 22 shows that for some patients the humeral anchor 550 can be adapted to be patient specific with regard to the center of offset of the center of rotation. The humeral anchor 550 can include the stem portion 554 and the metaphysis portion 558. The metaphysis portion 558 can be coupled with an articular body 559. The stem portion 554 can extend along the primary stem axis 562 as discussed above.

The humeral anchor 550 can be configured such that the center of rotation of the articular body 559 can be aligned in the posterior-anterior direction with the primary stem axis 562. In one embodiment, the metaphysis portion 558 can be configured with respect to the stem portion 554 such that the geometric center of the metaphysis portion 558 is aligned in the posterior-anterior direction with the primary stem axis 562. The method 500 can be used, e.g., in the step 520, to modify the humeral anchor to adjust the center of rotation of the articular body 559 relative to the stem portion 554. FIG. 22 shows that a posterior center of rotation offset 590 can be provided between the stem portion 554 and the metaphysis portion 558. The posterior center of rotation offset 590 provides that the center of rotation of the articular body 559 (large cross) can be disposed in a posterior direction (to the right on the page) relative to the posterior-anterior direction relative to the posterior-anterior location (small cross) of primary stem axis 562.

The posterior center of rotation offset 590 can be approximately 2 mm. The posterior center of rotation offset 590 can be approximately 4 mm. The posterior center of rotation offset 590 can be between 1 and 8 mm. The posterior center of rotation offset 590 can be between 2 and 6 mm.

Figure 23:
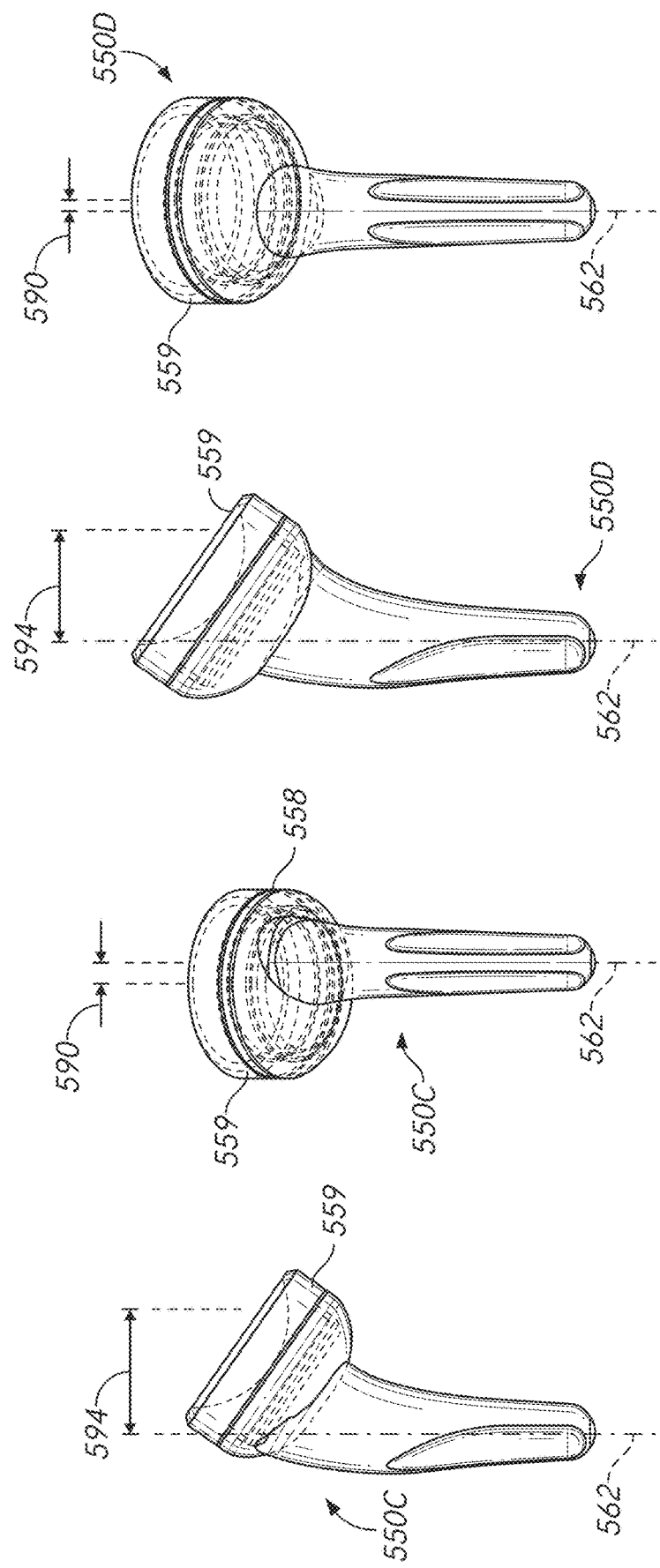
FIG. 23 includes anterior and lateral views of two embodiments having different levels of offset between a stem and a center of rotation of an articular body thereof.

FIG. 23, in the right-most image, shows the center of rotation offset 590 can also be provided in an anterior direction between the center of rotation of the articular body 559 and the posterior-anterior location of primary stem axis 562. An anterior offset of can be approximately 1 mm, can be approximately 2 mm, can be approximately 3 mm, can be approximately 4 mm in some embodiments. The anterior center of rotation offset 590 can be between 1 and 5 mm inclusive. The anterior center of rotation offset 590 can be between 2 and 4 mm inclusive.

FIG. 23 also shows that a medial center of rotation offset 594 can be provided that can be adjusted in a patient specific manner as well. The center of rotation of the articular body 559 can be off-set in a medial direction relative to the primary stem axis 562 by a first amount (left-most image) and can be off-set in a medial direction relative to the primary stem axis 562 by a second amount (third-from left image). The first amount can be within a range of 18-26 mm inclusive, or can be within a range of 19-25 mm inclusive, or can be within a range of 20-24 mm inclusive. The first amount can be about 22 mm. The second amount can be within a range of 10-19 mm inclusive, or can be within a range of 12-18 mm inclusive, or can be within a range of scapula 14-17 mm inclusive. The second amount can be about 17 mm.

Providing a patient specific posterior or anterior offset of the center of rotation of the articular body 559 relative to the primary stem axis 562 or another part of the stem portion 554 can advantageously allow the surgeon to better fit the humeral anchor to the specific patient's shoulder. Additional benefits of patient specific posterior-anterior offset adjustment can reduce, minimize or eliminate impingement risk and/or dislocation risk and can optimize range of motion, stability, and soft-tissue tensioning.

3. Humeral Anchors with Patient Specific Patient Specific Version Adjustment

Figure 24:
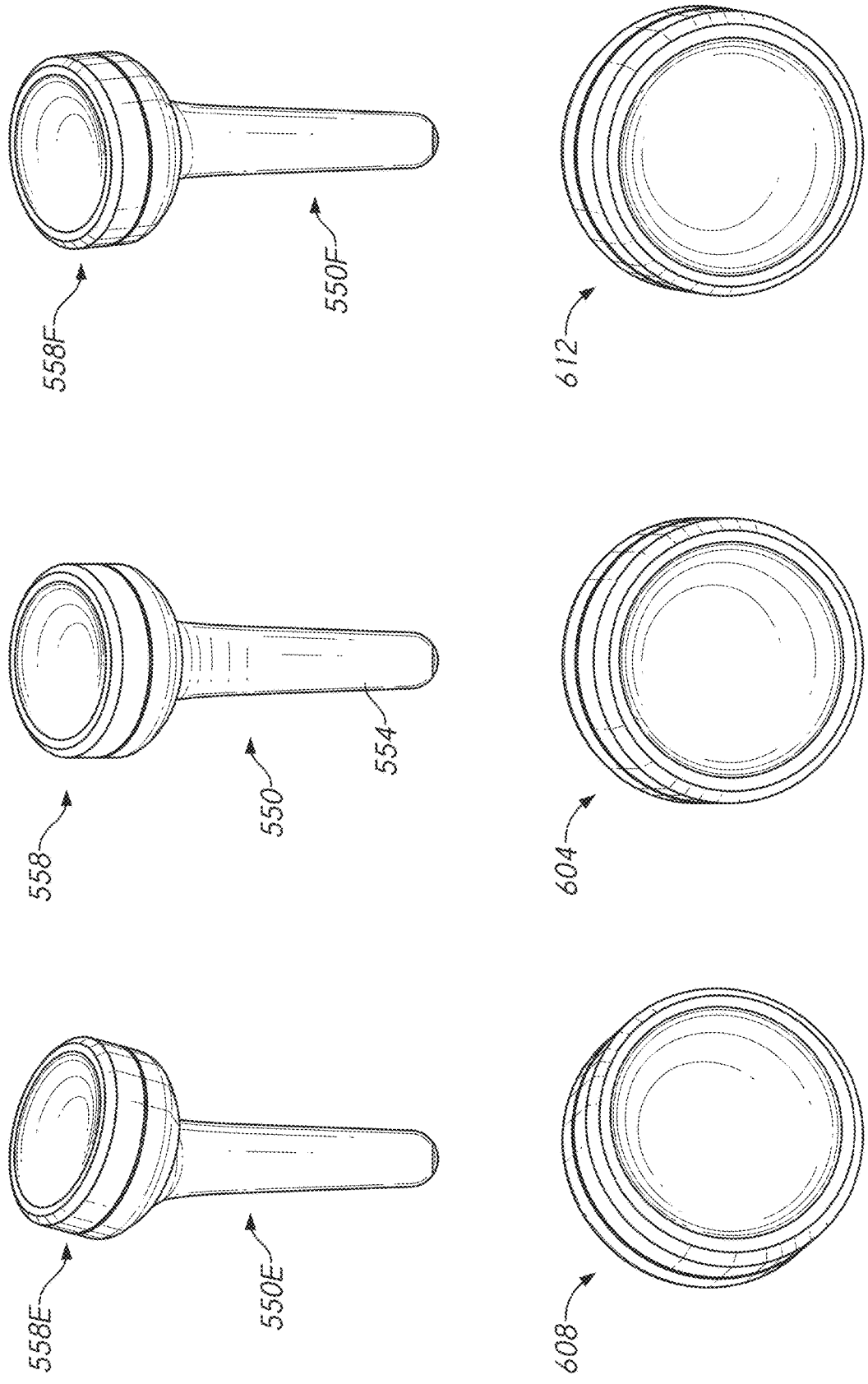
FIG. 24 includes lateral views of view of three embodiments of a humeral anchor, each having a different level of version.

FIG. 24 show another aspect in which the method 500 can confirm a manufacturing plan, potentially following a modification of an initial manufacturing plan wherein a patient specific version is provided. The humeral anchor 550 includes an initial version angle 604 as defined between the stem portion 554 and the metaphysis portion 558. As with other initial settings of the various parameters described herein the initial version angle 604 can be selected as a center of a distribution of suitable version settings for an expected population. In one approach the initial version angle 604 is selected as a neutral setting. This assumes that when the humerus is in a neutral position a scapula side articular surface (e.g., on a glenosphere) with which the articular body interacts will be entered on the articular body.

If the scapula side articular surface is angled anteriorly the initial version angle 604 can be adjusted in the step 520. For example a humeral anchor 550E can be provided in which a first version offset 608 is provided. The first version offset 608 is offset from the initial version angle 604. The first version offset 608 is well suited to a scapula side articular surface that is oriented anteriorly. For such a scapula side articular surface the first version offset 608 allows the center of the articular body 559 to be centered on the center of the scapula side articular surface. This allows for approximately equal amounts of motion in anterior and posterior directions for example. The first version offset 608 can be between 5 and 50 degrees inclusive, can be between 10 and 45 degrees inclusive, can be between 15 and 40 degrees inclusive, can be between 20 and 35 degrees inclusive, can be approximately 25 degrees in some embodiments. Arriving at a selected first version offset 608 for a specific patient can be through the iterative method 500, e.g., incrementally increasing the first version offset 608 until a patient specific arrangement is selected.

If the scapula side articular surface is angled posteriorly the initial version angle 604 can be adjusted in the step 520. For example a humeral anchor 550F can be provided in which a second version offset 612 is provided. The second version offset 612 can be measured in the same direction as the first version offset 608, for example a counter-clockwise angle from 12 o'clock. The second version offset 612 is offset form the initial version angle 604. The second version offset 612 is well suited for a scapula side articular surface that is oriented posteriorly. For such a scapula side articular surface the second version offset 612 allows the center of the articular body 559 to be centered on the center of the scapula side articular surface. This allows for approximately equal amounts of motion in anterior and posterior directions for example. The second version offset 612 can be between reamer shaft 300 and 355 degrees inclusive, can be between 320 and arrow 355 degrees inclusive, can be between 340 and 355 degrees inclusive, can be approximately 350 degrees in some embodiments. Arriving at a selected second version offset 612 for a specific patient can be through the iterative method 500, e.g., incrementally increasing the first version offset 608 until a patient specific arrangement is selected.

Additional benefits of patient specific version adjustment can reduce, minimize or eliminate impingement risk and/or dislocation risk and can optimize range of motion and stability.

4. Humeral Implant with Patient Specific Metaphysis Portion Thickness

Figure 25:
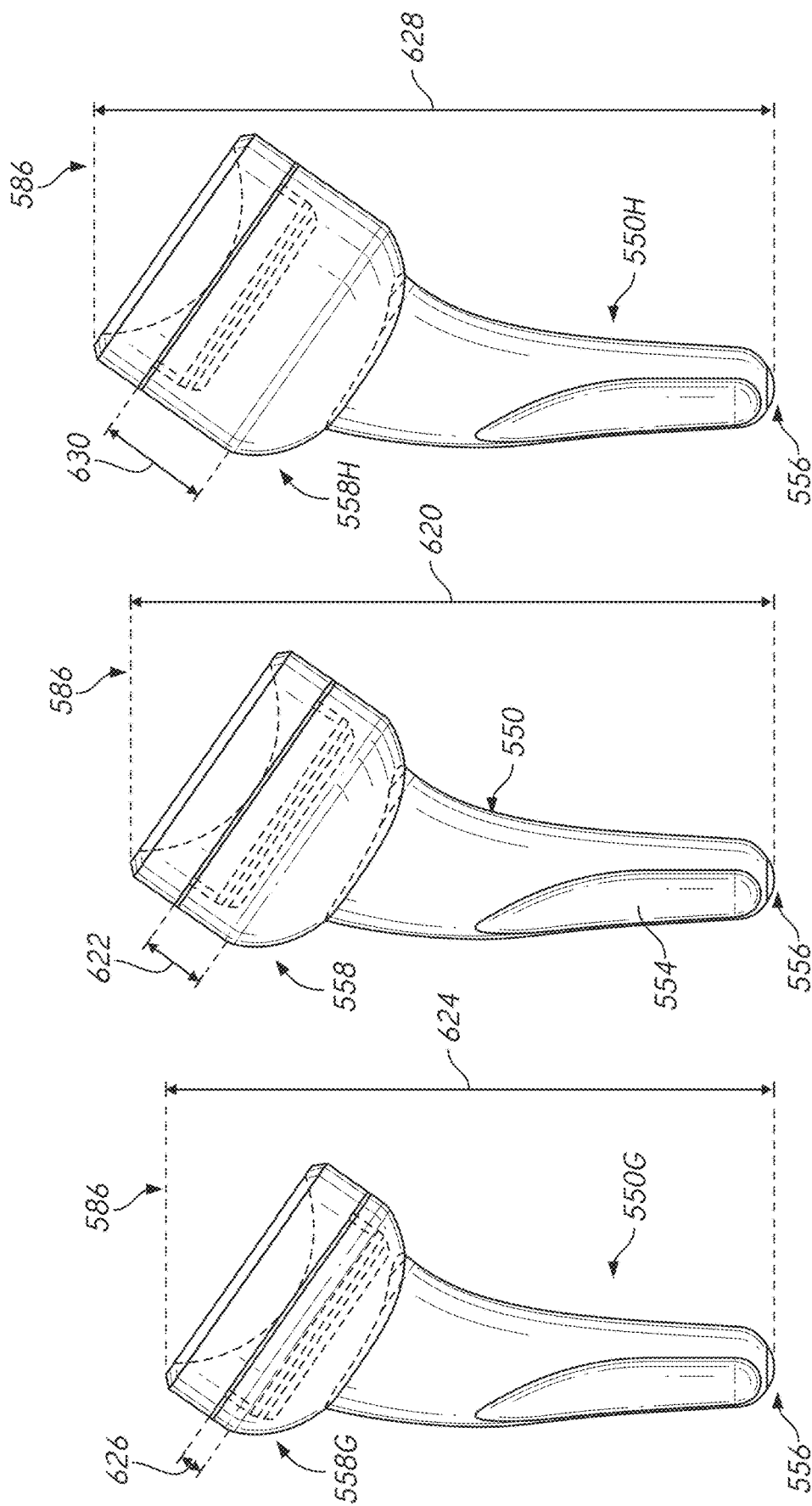
FIG. 25 includes anterior views of view of three embodiments of a humeral anchor, each having a different level of metaphysis thickness.

FIG. 25 show another aspect in which the method 500 can confirm a manufacturing plan, potentially following a modification of an initial manufacturing plan wherein a patient specific thickness of a humeral implant, e.g., a metaphyseal portion of a humeral anchor is provided. The humeral anchor 550 can have a metaphysis bowl thickness 622 that is initially selected and provided in the step 508 of the method 500. The metaphysis bowl thickness 622 can be selected initially based upon a relevant population of patients. The metaphysis bowl thickness 622 can be based on an evaluation such as described in connection with FIG. 20C.

FIG. 25 shows that a humeral implant length 620 is another parameter that can be made patient specific. In this context, humeral implant length 620 is defined as the superior-inferior distance from the inferior end 556 of the humeral anchor 550 to the initial center of rotation position 586. In one variation of the method 500 the step 520 adjusts the thickness of the metaphysis bowl. Humeral anchor 550G is an embodiment with a first modified metaphysis bowl thickness 626. The first modified metaphysis bowl thickness 626 has a thickness that is less than the thickness of the humeral anchor 550. The first modified metaphysis bowl thickness 626 corresponds to a first modified humeral implant length 624, one that is less than the humeral implant length 620 of humeral anchor 550.

In another embodiment, a humeral anchor 550H is provided that can be manufactured following the method 500. The humeral anchor 550H can include a second modified metaphysis bowl thickness 630 that is greater than the humeral implant length 620. The second modified metaphysis bowl thickness 630 can provide a second modified humeral implant length 628.

The second modified humeral implant length 628 has the benefit of moving the center of rotation of the humerus to which the humeral anchor 550H is a part to be moved further away from the mid-line of the patient. This can be useful in addressing a patient with lax soft tissue around the shoulder or with larger patients. The humeral anchor 550G has the benefit of moving the center of rotation of the humerus to which the humeral anchor 550G is a part to be moved toward the mid-line of the patient. This can be useful in addressing a patient with tight soft tissue around the shoulder or with smaller patients.

Additional benefits of patient specific humeral implant thickness can reduce, minimize or eliminate dislocation risk and optimize stability.

5. Humeral Anchors with Patient Specific Articular Body Lead Angle

FIG. 26 shows another aspect in which the method 500 can confirm a manufacturing plan, potentially following a modification of an initial manufacturing plan wherein a patient specific articular body lead angle is provided. In one embodiment the humeral anchor 550 is coupled with an articular body 559. The articular body 559 has a lead angle 642 which can be the angle disposed between an outer peripheral surface of the articular body 559 and a superior side of the articular body 559 as shown. The lead angle 642 can be modified in the method 500 from an initial lead angle 642 to a modified lead angle 646 that is advantageous from the perspective of one or more aspects of performance. For example, in the step 512 of the method 500 a biomechanical analysis can include confirming whether the articular body 559 impinges on any bone during the course of movement. If there is bone impingement is likely as indicated in the step 512, the method 500 can follow to the step 520 in which the lead angle can be modified. The lead angle can be decreased to reduce the likelihood of impingement, e.g., to the modified lead angle 646.

In at least one method, the lead angle can initially be defined in the step 508 as a relatively smaller angle, e.g., similar to the angle modified lead angle 646 and can be increased following the step 512 in which a lack of impingement is confirmed. For some patients where impingement is less likely the method 500 can be shorter if starting with a larger initial lead angle in the step 508. For some patients where impingement is more likely the method 500 can be shorter if starting with a smaller initial lead angle in the step 508.

Additional benefits of patient specific articular boy lead angle can reduce, minimize or eliminate notching risk.

6. Humeral Anchors with Patient Specific Metaphysis Portion Width

FIG. 27 shows another aspect in which the method 500 can confirm a manufacturing plan, potentially following a modification of an initial manufacturing plan wherein a patient specific metaphyseal portion and/or articular body width is provided. The width of the metaphysis portion 558 and/or the width of the articular body 559 can be set as corresponding to a first metaphysis width 662. The first metaphysis width 662 can be the same for the superior face of the humeral anchor 550 and for the superior edge of the articular body 559. The first metaphysis width 662 can be initially defined in the step 508. The initial width can be about 36 mm, and in some embodiments can be from 32-40 mm, in other embodiments between 28 and 44 mm.

In part of the method 500 the appropriateness of the width can be confirmed in the method 500, such as in the step 512. If a wider metaphysis portion 558 and/or a wider articular body 559 is deemed suitable, the step 520 can adjust the width upward. A humeral anchor 550I can be provided with a second metaphysis width 666 that is wider than the first metaphysis width 662. The second metaphysis width 666 can be about 42 mm in one embodiment. The second metaphysis width 666 can be in a range 38-46 mm or 32-50 mm in other embodiments.

To expedite the method 500 the initial width can be similar to the first metaphysis width 662 and then adjusted toward the second metaphysis width 666 or can initially be similar to the second metaphysis width 666 and adjusted to the first metaphysis width 662. Also, a middle width can be initially selected and the method 500 be used to adjust the width upward or downward.

Providing a patient specific metaphyseal portion and/or articular body width can advantageously allow the surgeon to better fit the humeral anchor to the specific patient's shoulder.

7. Humeral Anchors with Patient Specific Articular Body Center of Rotation Offset FIG. 28 shows another aspect in which the method 500 can confirm a manufacturing plan, potentially following a modification of an initial manufacturing plan wherein a patient specific articular body center of rotation offset is provided. For example, in one variant of the method 500 the articular body 559 is configured in the step 508 with a concave articular recess that is centered relative to, e.g., where a line connecting a center of rotation of the articular body 559 with the geometric center of the outer periphery of the superior face of the articular body 559 is normal to the superior face of the articular body 559. Said another way, in the step 508 where the initial manufacturing plan is defined projection of the center of rotation onto the plane of the superior face of the articular body 559 intersects the geometric center of the superior face of the articular body 559.

FIG. 28 shows an articular body 559B that can result from the step 512 and step 520, resulting in the center of rotation being offset from the geometric center of the articular body 559B. In particular, a first center of rotation position 682 can be provided, wherein the center of rotation is offset from the geometric center. The first center of rotation position 682 is illustrated by a small cross on the face of the articular body 559B. The geometric center is illustrated by a large cross on the face of the articular body 559B. As can be seen, the small cross is disposed to the left and above the center of the large cross in the figure for the first center of rotation position 682. The distance from the geometric center to the first center of rotation position 682 can be approximately 1 mm, can be approximately 2 mm, can be approximately 3 mm, can be approximately 4 mm in some embodiments. The distance from the geometric center to the first center of rotation position 682 can be between 1 and 5 mm inclusive. The distance from the geometric center to the first center of rotation position 682 can be between 2 and 4 mm inclusive.

FIG. 28 shows an articular body 559C that can result from the step 512 and step 520, resulting in the center of rotation being offset from the geometric center of the articular body 559C. In particular, a second center of rotation position 686 can be provided, wherein the center of rotation is offset from the geometric center. The second center of rotation position 686 is illustrated by a small cross on the face of the articular body 559C. The geometric center is illustrated by a large cross on the face of the articular body 559C. As can be seen, the small cross is disposed directly to the left of the center of the large cross in the figure for the second center of rotation position 686. The distance from the geometric center to the second center of rotation position 686 can be approximately 1 mm, can be approximately 2 mm, can be approximately 3 mm, can be approximately 4 mm in some embodiments. The distance from the geometric center to the second center of rotation position 686 can be between 1 and 5 mm inclusive. The distance from the geometric center to the second center of rotation position 686 can be between 2 and 4 mm inclusive.

In other variations, the center of rotation position can be to the left and below, directly to the right of, to the right and above, or to the right and below, the geometric center.

Providing a patient specific articular body center of rotation offset can advantageously allow the surgeon to better fit the humeral anchor to the specific patient's shoulder. Additional benefits of patient specific articular body center of rotation offset can reduce, minimize or eliminate impingement risk and dislocation risk and can optimize range of motion, stability, and soft tissue tensioning.

8. Humeral Anchors with Patient Specific Metaphysis Portion Inset Depth

Figure 29:
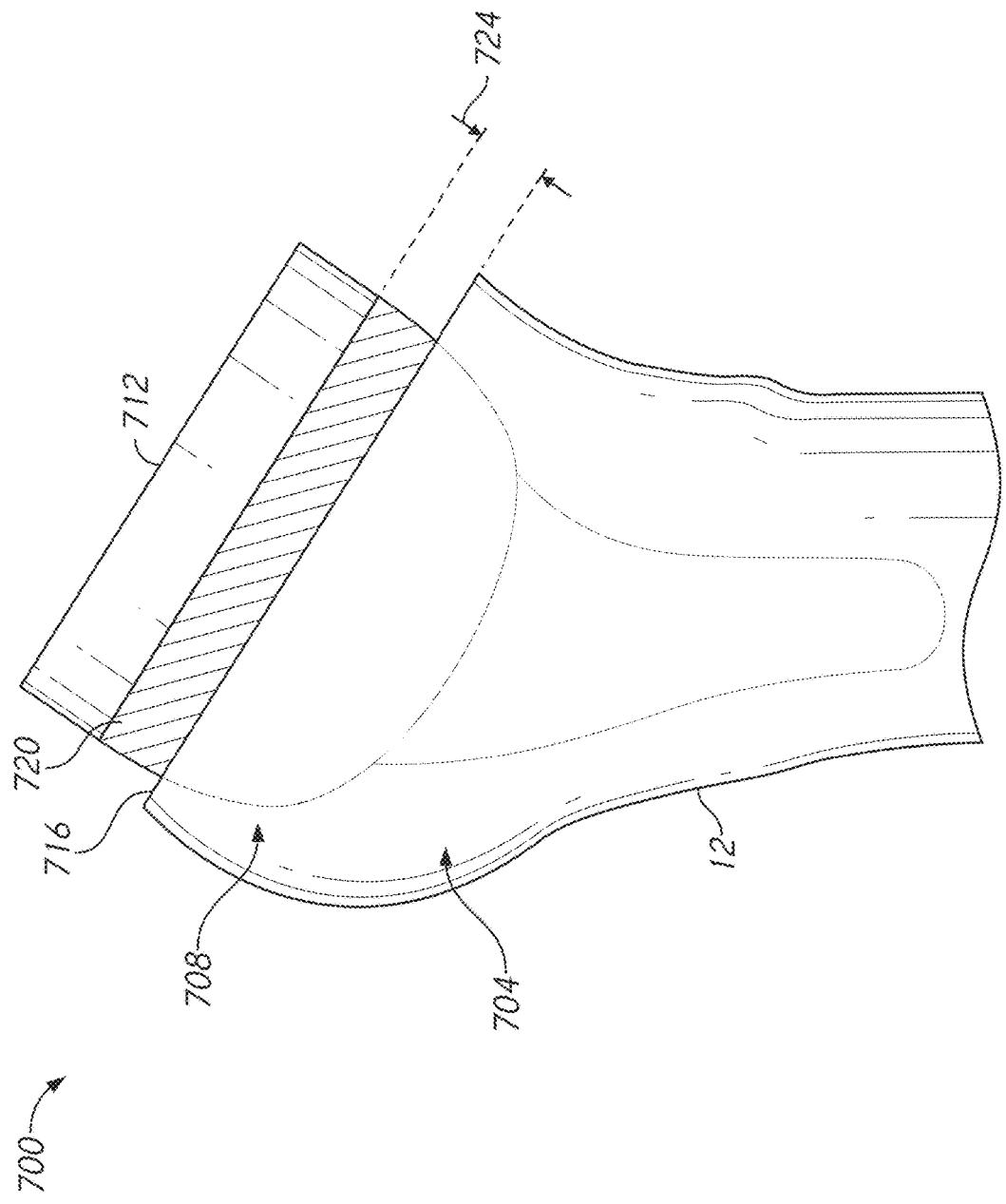
FIG. 29 includes anterior view of a humeral anchor and assembly placed in a humerus, the humeral anchor being configurable to provide different levels of inset positioning in the resected humerus.

FIG. 29 shows another aspect in which the method 500 can confirm a manufacturing plan, potentially following a modification of an initial manufacturing plan wherein a patient specific metaphysis portion inset depth is provided. The humeral implant 700 can have a metaphysis portion 708 inlay depth 724 that is initially selected and provided in the step 508 of the method 500. The inlay depth 724 can be selected initially based upon a relevant population of patients. The inlay depth 724 can be based on an evaluation such as described in connection with FIG. 20C.

FIG. 29 shows a humeral implant 700 that can result from the step 512 and step 520, resulting in the metaphysis portion 708 of the humeral anchor protruding superiorly of a resection surface 716 when the humeral anchor is implanted within the resected humerus. In particular, an inlay depth 724 can be provided wherein the metaphysis portion 708 extends in part above the resection surface 716. As can be seen, the inlay depth 724 relates to the depth that the metaphysis bowl is set into the metaphysis bone and is characterized by the distance from the resection surface 716 to the superior face 720 of the metaphysis portion 708. The inlay depth 724 can be between 0 and 20 mm, can be between 5 and 10 mm, can be between 7 and 18 mm, e.g., can be 12 mm.

An inlay depth 724 of 0 mm places the resection surface 716 and the superior face 720 of the metaphysis portion 708 in alignment. In other variations, the inlay depth 724 can be a negative value. For example, an inlay depth 724 can be provided wherein the entire metaphysis portion 708 sits below the resection surface 716. A negative inlay depth 724 places the superior face 720 of the metaphysis portion 708 below the resection surface 716. The inlay depth 724 can be between 0 and −10 mm, e.g. can be −3 mm.

As discussed above in connection with FIGS. 16 and 17, where the outer inferior surface is configured in a patient specific manner, it can be advantageous to provide a patient specific reamer head, such as the reamer head 328 discussed above.

Providing a patient specific metaphysis portion inset depth can advantageously allow the surgeon to better fit the humeral anchor to the specific patient's shoulder. Additional benefits of patient specific metaphysis portion inset depth can provide more appropriate levels of soft tissue tensioning for the specific patient.

9. Humeral Anchors with Patient Specific Articular Body Jump Distance

Figure 30:
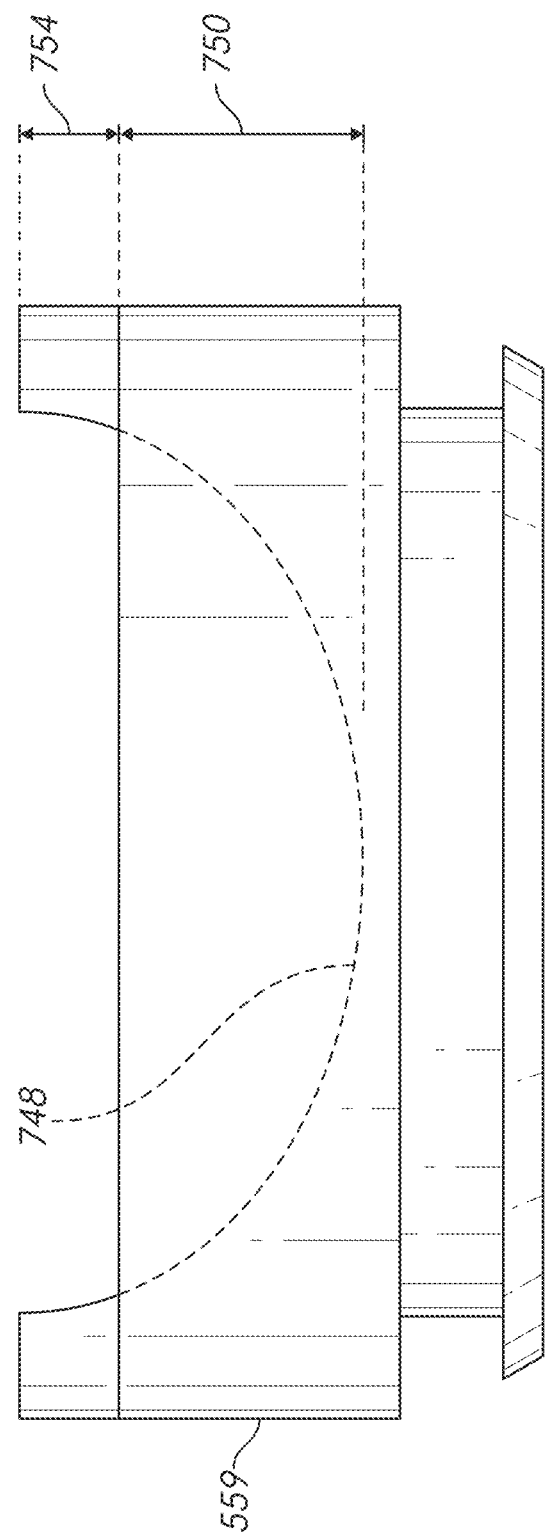
FIG. 30 is a side view of embodiments of inserts for reverse humeral assemblies, the insert embodiments having a patient specific modified jump distance.

FIG. 30 shows another aspect in which the method 500 can confirm a manufacturing plan, potentially following a modification of an initial manufacturing plan wherein a patient specific articular body jump distance is provided. The articular body 559 can have an initial jump distance 750 that is initially selected and provided in the step 508 of the method 500. The initial jump distance 750 can be selected initially based upon a relevant population of patients. The initial jump distance 750 can be based on an evaluation such as described in connection with FIG. 20C.

FIG. 30 shows that an articular body 559 initial jump distance 750 is another parameter of a humeral implant that can be made patient specific. In this context, jump distance is defined as the distance from the deepest portion of a concave articular surface 748 of the articular body 559 to a superior edge of the articular body 559. In part of the method 500 the appropriateness of the initial jump distance 750 can be confirmed in the method 500, such as in the step 512. If a modified jump distance 754 is deemed suitable, the step 520 can increase or decrease the initial jump distance 750.

In various embodiments, the initial jump distance dimension 750 can be increased by 1 mm to head 10 mm, can be increased by 2 mm to 8 mm, can be increased by 3 mm to 6 mm. In various embodiments the initial jump distance dimension 750 can be increased by 2, 4, 8, or 10 mm.

Additional benefits of patient specific articular body jump distance can reduce, minimize, or eliminate dislocation risk and can optimize stability.

Figure 31:
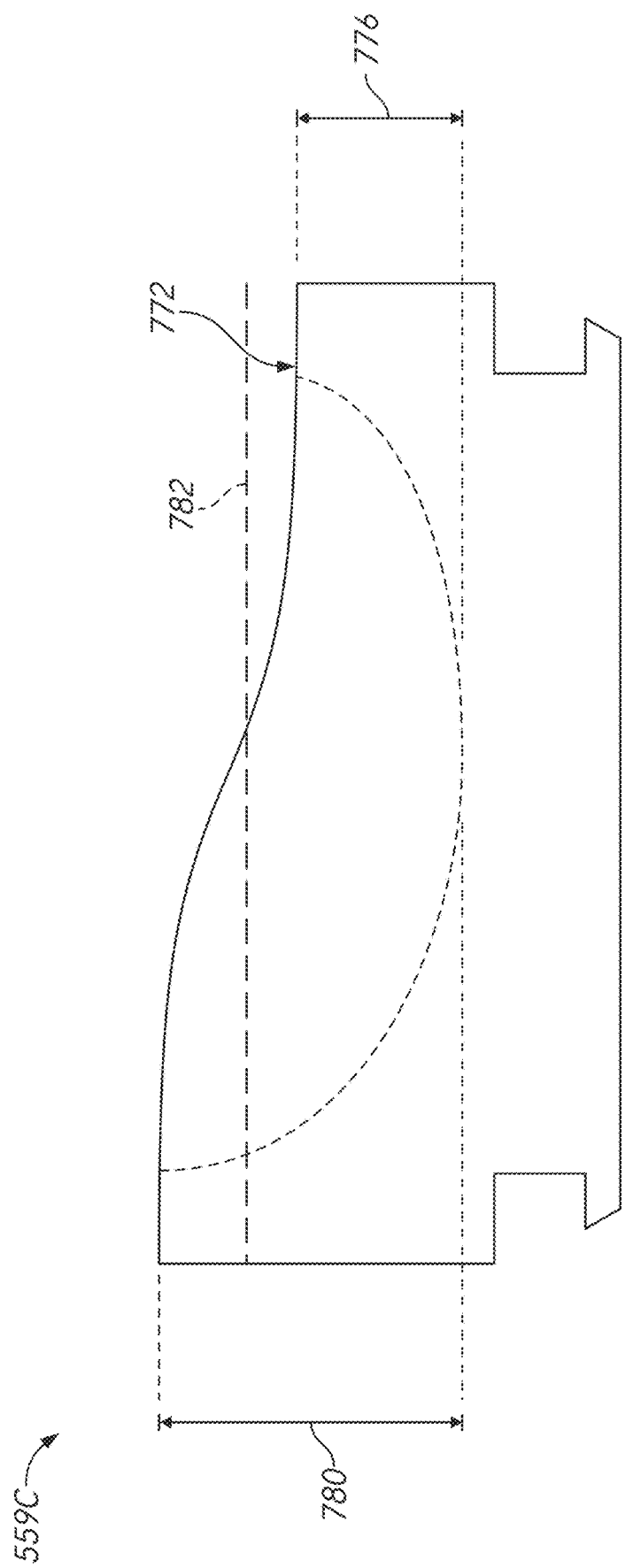
FIG. 31 is a side view of embodiments of inserts for reverse humeral assemblies, the insert embodiments having asymmetry in jump distance which can be provided in a patient specific manner.

10. Humeral Anchors with Patient Specific Articular Body Jump Distance Asymmetry FIG. 31 shows another aspect in which the method 500 can confirm a manufacturing plan, potentially following a modification of an initial manufacturing plan wherein a patient specific articular body jump distance asymmetry is provided. The articular body 559C can have jump distance asymmetry that is initially selected and provided in the step 508 of the method 500. The jump distance asymmetry can be selected initially based upon a relevant population of patients. The jump distance asymmetry can be based on an evaluation such as described in connection with FIG. 20C. In one variant, the articular body 559C can initially be configured in a symmetric manner without any asymmetry in the jump distance. Thereafter, the method 500 can define asymmetry as discussed below.

FIG. 31 shows an articular body 559C that can result from the step 512 and the step 520, resulting in an articular body 559C with patient specific jump distance asymmetry. In particular, an articular body 559C can be provided wherein the articular body 559C has an increased jump distance portion 780 and a decreased jump distance portion 776. In this context, jump distance asymmetry is defined as the jump distance difference between two portions of a superior edge 772 of an articular body 559C. In part of the method 500 the appropriateness of the initial jump distance asymmetry can be confirmed in the method 500, such as in the step 512. If a modified jump distance asymmetry is deemed suitable, the step 520 can increase or decrease the initial jump distance asymmetry. The methods herein provide for great flexibility in the configuring of the superior edge 772 to provide optimal jump distance and dislocation control. For example, there can be one high point compared to a neutral (initially defined) jump distance. A high point can be provided at the 12 o'clock position when viewing from the superior side and a low point can be provided at the 6 o'clock position when viewed from the superior side. The position of a high and a low point can be very flexibly defined, such that the high point can be anywhere and the low point also can be anywhere about the superior edge 772. Also, the low and high points can be opposite each other, e.g., 180 degrees apart, but can also be closer to each other, such as being 120 degrees from a high point to a low point, 90 degrees from a high point to a low point, 60 degrees from a high point to a low point, 45 degrees from a high point to a low point, or between about 5 degrees and 45 degrees spacing from a high point to a low point. The foregoing angular spacing can be either direction from the 12 o'clock position (e.g., anterior or posterior). Also, more than one high point and/or more than one low point can be provided in certain embodiments. For example, the method 500 can conclude at the step 528 with an increased height at the 12 o'clock position, a lower than neutral height at 3 o'clock, an increased height at 6 o'clock, and a lower than neutral height at the 9 o'clock position. Also, where more than one higher or more than one lower position is provided the degree of increase in the height of the superior edge 772 need not be the same for the portions that are increased. The degree of decrease in height of the superior edge need not be the same for the portions that are decreased. Thus, many adjustments can be made that better configure the articular body 559 for the specific patient.

Various embodiments can provide different jump distance asymmetry arrangements. For example the increased jump distance portion 780 can be disposed 1, 2, 4, or 6 mm above a neutral or symmetric jump distance level 782. The decreased jump distance portion 776 can be disposed 1, 2, 4, or 6 mm below a neutral or symmetric jump distance level 782. A superior-inferior distance from a decreased portion of the superior edge of the articular body 559C and an increased portion of the superior edge can be 1 mm, 2 mm, 4 mm, 8 mm, or 12 mm in various embodiments.

Providing a patient specific articular body jump distance asymmetry can advantageously allow the surgeon to better fit the humeral anchor to the specific patient's shoulder. Additional benefits of patient specific articular body jump distance asymmetry can reduce, minimize, or eliminate dislocation risk and/or notching risk.

IV. Soft Tissue Tension Adapted Humeral Positioning

The foregoing approaches to providing a humeral implant provide many advantages. These approaches can be used in combination with the following humeral positioning system. Likewise, the following systems and methods can be combined with the foregoing systems and methods to provide improved soft tissue tensioning for a patient.

In shoulder arthroplasty, and in particular in reverse shoulder arthroplasty, management of the position of the humerus 12 in relation to the glenoid 18 is important to the management of the soft-tissue around the shoulder joint. Soft-tissue management is important for range of motion, stability of the implant (from dislocation), for reducing notching and the chance of acromion stress fractures. FIGS. 32 and 33 shows aspects of soft tissue tension management. FIG. 32, left image, shows shoulder anatomy prior to surgery, including the center of rotation of the humerus 12 on the glenoid 18. The dimension "A" is a measure of lateral distance that relates to the tension in the rotator cuff bounding the humeral head. The dimension "B" is a measure of arm length or inferior-superior positioning of the humerus relative to the scapula and relates to the tension in the deltoid. Excessive tension in these soft tissues following implantation (e.g., the A' or B' dimensions in FIG. 32) can result in poor outcomes following the surgery. For example, excessive tension in the deltoid can result in an acromial fracture. A too small A' dimension (see FIG. 33, left image) may correspond to insufficient tension which can result in a dislocation. A too large A" dimension (see FIG. 33, right image) may result in excessive cuff tension that would overly restrict range of motion. To provide better outcomes, implant system should be able to adjust position, e.g., of the center of rotation of the humeral system, independently in the medial-lateral direction (e.g., parallel to the dimensions A, A', A") and in the inferior-superior direction (e.g., parallel to the dimensions B, B').

Figure 34:
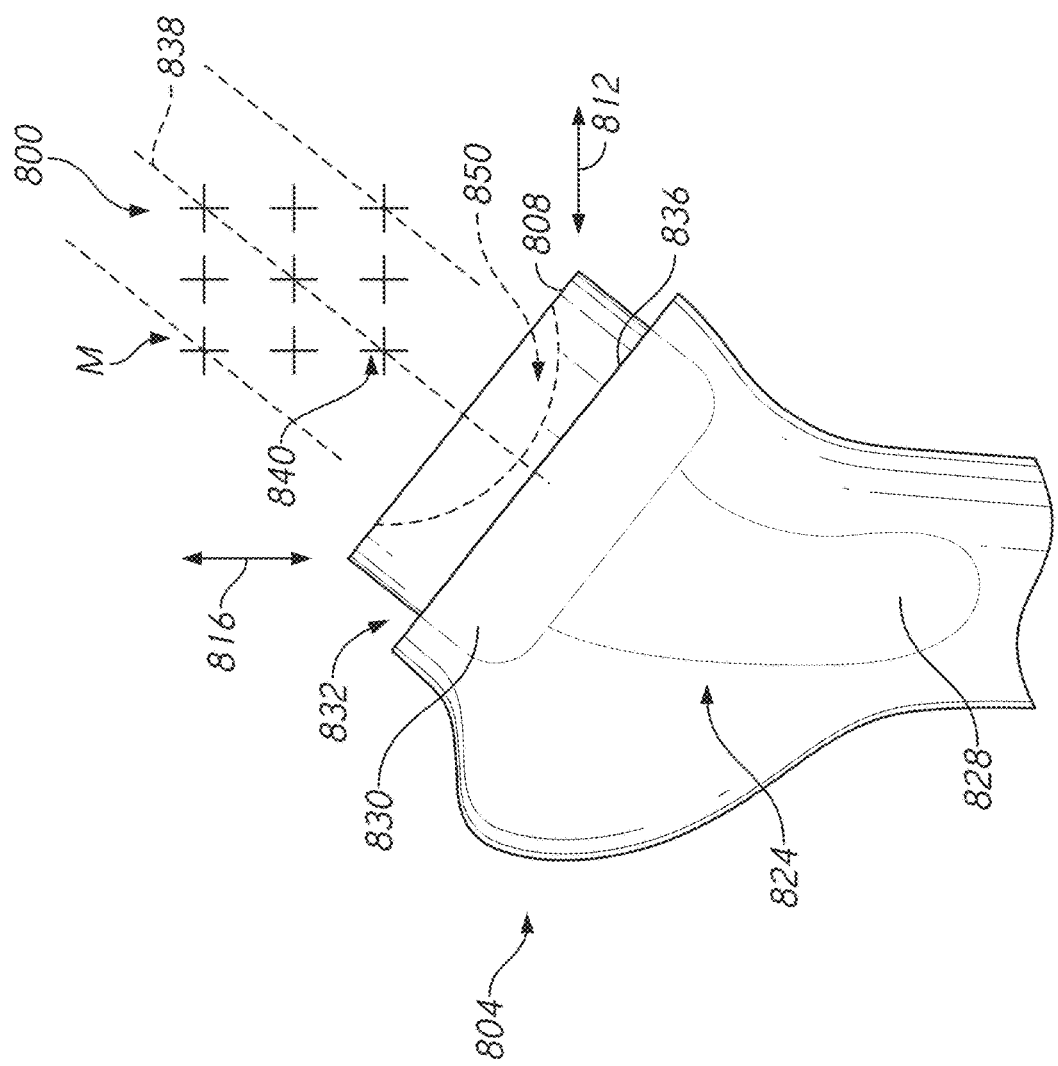
FIG. 34 illustrates a humeral positioning system and method that enables adjustment of the system to provide appropriate soft tissue tensioning.
Figure 35:
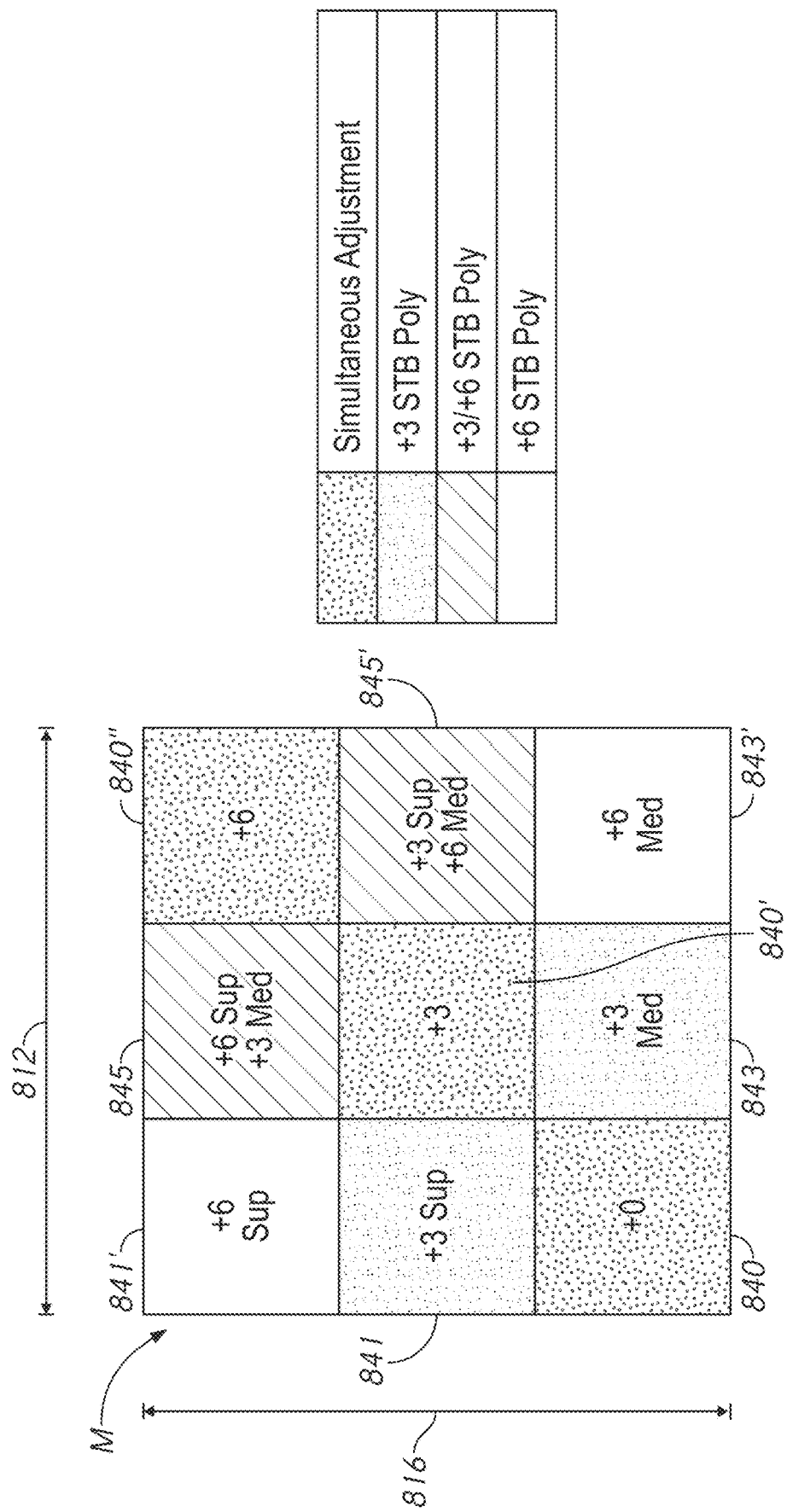
FIG. 35 illustrates a system and a kit to enable a surgeon to provide an appropriate humeral position for appropriate soft tissue tensioning.

FIGS. 34 and 35 illustrate a humeral positioning system 800 that facilitates managing soft tissue tensioning in a shoulder procedure, such as in reverse shoulder arthroplasty. The humeral positioning system 800 includes a humeral anchor 804 and an articular component 808. The humeral positioning system 800 is able to make adjustments in a medial-lateral direction 812 and to make adjustments in an inferior-superior direction 816 as discussed further below.

The humeral anchor 804 includes a stem 824 that extends to an inferior end 828 of the humeral anchor 804. The humeral anchor 804 includes a superior end 830 disposed opposite to the inferior end 828. The superior end 830 includes a mounting portion 832 disposed at the superior end 830. The mounting portion can be enlarged compared to the inferior end 828 of the stem 824. In other embodiments, the humeral anchor 804 can comprise a stemless anchor which does not include the stem 824 shown in FIG. 34.

The articular component 808 can include an articular surface 850 (shown in FIG. 34 schematically in dashed line). The articular surface 850 can be curved to have a center of rotation 840 that can be disposed at a position based on the configuration of the articular component 808. In one example, a neutral configuration of the humeral positioning system 800 can be provided in which a center of rotation 840 of the articular component 808 is located on an axis 838 disposed away from a mounting face 836 of the humeral anchor 804. The mounting face 836 of the humeral anchor 804 can be defined at or near the superior end of the mounting portion 832 and can have a component parallel to the resection surface of the humerus 12 in one embodiment. The axis 838 can be disposed perpendicular to the mounting face 836 in one embodiment. The configuration illustrated in FIG. 34 can provide a neutral configuration in that the center of rotation 840 is located on the axis 838, perpendicular to the mounting face 836. The mounting face 836 can have a complex structure, e.g., disposed about a mounting channel similar to the mounting channel 120 discussed above. The mounting face 836 can have rotational position features disposed therein, as discussed further below and shown schematically in FIG. 36.

FIG. 34 schematically illustrates a matrix M of centers of rotation, with each center of rotation illustrated with a "+" in FIG. 34. The matrix M of FIG. 34 is also illustrated in FIG. 35 in table format. The center of rotation 840 for the selected combination of the humeral anchor 804 and the articular component 808 shown in FIG. 34 is disposed at the lower left-hand portion of the matrix M (see also FIG. 35). The matrix M has nine positions, but in other embodiments, more or fewer positions may be provided. From the neutral position illustrated in FIG. 34 an additional configuration can be provided in which the center of rotation is disposed along the axis 838 farther away from the mounting face 836 than in the center of rotation 840. A first increment along this axis 838 can provide a second center of rotation 840' (see FIG. 35) of a humeral positioning system 800 including the humeral anchor 804 and a second, different articular component 808 that is thicker (as compared with the articular component that provides the center of rotation 40) along the direction of the axis 838. For example, the second articular component 808 can be thicker than the articular component 808 by the magnitude of the increment from the center of rotation 840 at the lower left position of the matrix M to a position in the center of the matrix M. A second increment along the axis 838 can provide a center of rotation 840" (see FIG. 35) of a humeral positioning system 800 including the humeral anchor 804 and a third, different articular component 808 that is thicker along the direction of the axis 838 by the magnitude of the increment from the center of rotation 840 at the lower left position of the matrix M to a position at the upper right of the matrix M. The position of the center of rotation 840 relative to the first and second increments provide simultaneous adjustment in both the medial-lateral direction 812 and the inferior-superior direction 816, as these first and second increments lie along the axis 838.

While these adjustments are useful, the matrix M illustrated in FIGS. 34 and 35 has additional positions in which the adjustment in the medial-lateral direction 812 and in the inferior-superior direction 816 are not one-to-one. For example, the matrix M illustrated in FIGS. 34 and 35 has an increment immediately superior to the location of the center of rotation 840 for the neutral configuration to define a first superior center of rotation 841. This increment provides an adjustment in only the inferior-superior direction 816 and no adjustment in the medial-lateral direction 812 relative to the position of the center of rotation 840. The matrix M can also include a second increment immediately superior to the first superior center of rotation 841 so as to define a second superior center of rotation 841'. The increments to the center of rotation 841 and the center of rotation 841 can be equal, e.g., 3 mm. In some embodiments, the increments can be in increments other than 3 mm, but may be in otherwise generally equal increments. In various embodiments, the increments can be in a range of 0.5 mm to 5 mm, in a range of 1 mm to 5 mm, in a range of 1.5 mm to 4.5 mm, or in a range of 2 mm to 4 mm.

Figure 36:
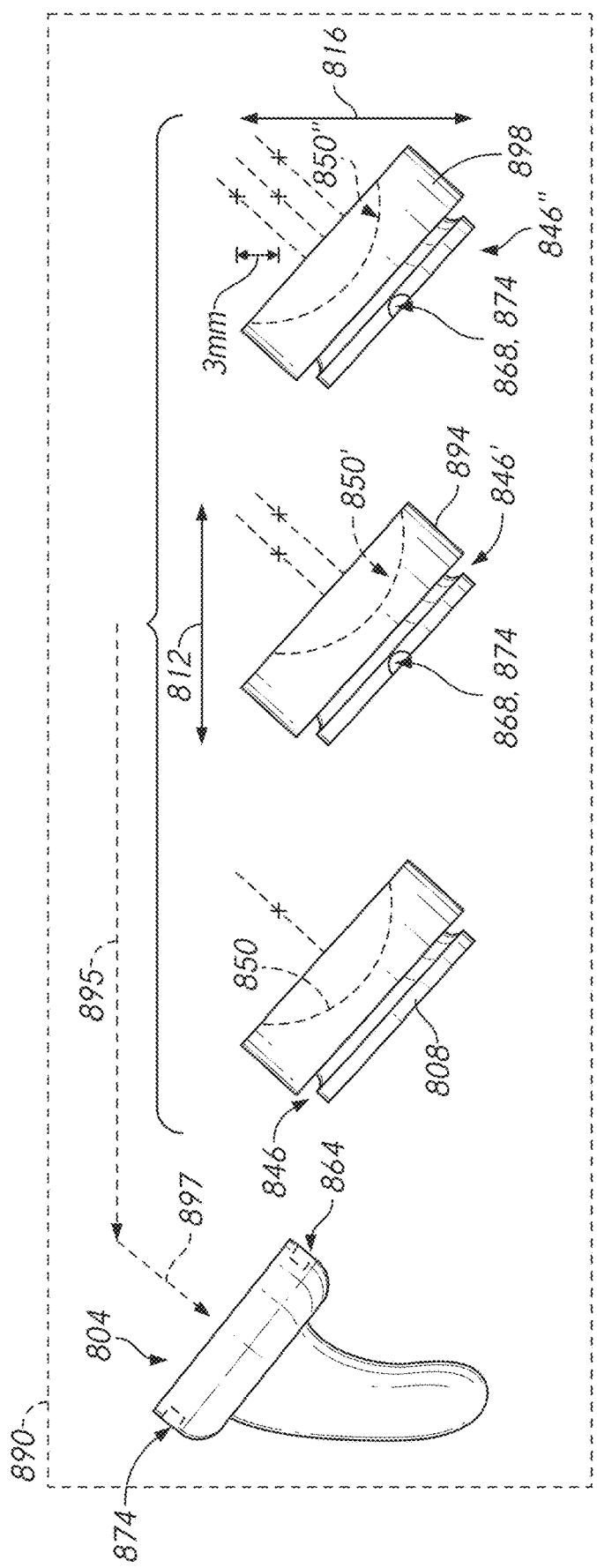
FIG. 36 illustrates three articular components that illustrate how the systems herein can provide adjustment in a medial-lateral direction without adjustment in an inferior-superior direction and can provide adjustment in an inferior-superior direction without adjustment in a medial-lateral direction.

Similarly, the matrix M illustrated in FIGS. 34 and 35 has a third increment immediately lateral to the location of the center of rotation 840 for the neutral configuration to define a first lateral center of rotation 843. This third increment provides an adjustment in only the medial-lateral direction 812 and no adjustment in the superior-inferior direction 816 relative to the position of the center of rotation 840. The matrix M can also include a fourth increment immediately lateral to the first lateral center of rotation 843 to define a second lateral center of rotation 843'. Further, as shown in the matrix M, fifth and sixth increments can provide both lateral and superior adjustments relative to the center of rotation 840 shown in FIG. 35, such that centers of rotation 845, 845' may be offset along both the lateral-medial axis 812 and the superior-inferior axis 816. FIG. 36 shows that the increments to the centers 845, 845' can be by different amounts in the medial-lateral direction 812 than in the inferior-superior direction 816 The center 845 can be disposed superiorly from the center of rotation 840 by a greater amount, e.g., by twice as much, in the inferior-superior direction 816 than in the medial-lateral direction 812. The center 845' can be disposed laterally from the center of rotation 840 by a greater amount, e.g., by twice as much, in the medial-lateral direction 812 than in the inferior-superior direction 816.

As described above, the humeral positioning system 800 can include a humeral anchor 804 and an articular component that when mated to the humeral anchor 804 locates the center of rotation at any one of the increments in FIGS. 34 and 35. The humeral positioning system 800 can be provided by selecting an articular component that provides the appropriate increment and coupling the selected body with the humeral anchor 804 to provide an increment that yields the desired soft tissue tension.

FIG. 36 illustrates a kit 890 that can include the humeral anchor 804 (which may be a stemmed or stemless anchor) and one or more of the articular components 808. In the illustrated embodiment, the kit 890 includes the humeral anchor 804, the articular component 808, a second adjusted articular component 894 configured for adjustment along the medial-lateral direction 812, and a third adjusted articular component 898 for an adjustment along the inferior-superior direction 816. The articular component 808 includes an engagement portion 846 and an articular surface 850 disposed on opposite sides thereof. The engagement portion 846 is configured to engage the mounting face 836 of the humeral anchor 804 in any suitable manner, such as by a c-ring, interference fit or any of the configurations disclosed above, all of which shall supplement the disclosure provided here. Similarly, the second adjusted articular component 894 can comprise an engagement portion 846' and an articular surface 850' opposite from the engagement portion 846'. The articular surface 850' in the second adjusted articular component 894 is shifted relative to the position of the articular surface 850 in the articular component 808. The shifted position causes the center of rotation of the second adjusted articular component 894 to be correspondingly shifted. The third adjusted articular component 898 can comprise an engagement portion 846" and an articular surface 850" opposite from the engagement portion 846". The articular surface 850" in the second adjusted articular component 898 is shifted relative to the position of the articular surface 850 in the articular component 808. The shifted position causes the center of rotation of the second adjusted articular component 898 to be correspondingly shifted.

In some embodiments, the number of articular bodies to provide a plurality of increments, such as are illustrated in the matrix M of FIGS. 34 and 35 can be less than the number of increments in the matrix M. In one approach, at least one of the second adjusted articular component 894 and the third adjusted articular component 898 can be configured to be coupled with the humeral anchor 804 in a plurality of (e.g., two) positions to provide two distinct increments in the matrix M of FIGS. 34 and 35. For example, the second adjusted articular component 894 can be configured to be coupled with the humeral anchor 804 in a first position to provide an increment of adjustment in the medial-lateral direction 812, such that the center of rotation may correspond to the first lateral center of rotation 843 of FIG. 35. The humeral anchor 804 can have a first rotational positioning feature 864. The second adjusted articular component 894 can have a second rotational position feature 868. The first rotational positioning feature 864 and the second rotational position feature 868 can engage with one another to enable the humeral anchor 804 to be secured to each other in a discrete pre-defined position. The position can be one that provides a desired position, e.g., a desired increment in the medial-lateral direction 812 without any adjustment in the inferior-superior direction 816. For example, referring to the matrix M of FIG. 35, when the first rotational positioning feature 864 is engaged with the second rotational position feature 868, the center of rotation can correspond to the first lateral center of rotation 843, as explained above. Thus, the second and third articular components 894, 898 can include clocking or rotational figures to place one or both of the components 894, 898 in two positions, e.g., two positions 180 degrees apart, so as to provide inferior-superior and lateral-medial adjustment. In other embodiments, however, one or more of the second and third articular components 894, 898 can include clocking or rotational features configured to place the components 894, 898 in more than two positions, e.g., in three, four, five, six, seven, eight, nine, ten, or more positions so as to provide adjustment along interior-superior and lateral-medial directions. In various embodiments, the different clocking positions may be evenly spaced.

In one embodiment, the mounting face 836 of the humeral anchor 804 can have a third rotational positioning feature 874. The third rotational positioning feature 874 can be secured or positioned relative to the first rotational positioning feature 864 such that the second adjusted articular component 894 is rotated 180 degrees from the position in which the first rotational positioning feature 864 is coupled to the second rotational position feature 868. For example, the second rotational positioning feature 868 of the second adjusted articular component 894 can engage with the first rotational positioning feature 864 of the anchor 864 to provide the 180 degree rotation. In some embodiments, the second and third rotational positioning features can be disposed 180 degrees circumferentially from one another. The rotation by 180 degrees can enable the second adjusted articular component 894 to provide an increment in the inferior-superior direction 816 without providing any increment in the medial-lateral direction 812. For example, when the first and third rotational positioning features 864 are engaged, the center of rotation can correspond to the first superior center of rotation 841 shown in FIG. 35. Thus, one modified embodiment of the kit 890 provides the second adjusted articular component 894 able to provide the centers of rotation 841, 843. In this embodiment, the third adjusted articular component 898 could be provided to offer the centers of rotation 841', 843'.

Because the second adjusted articular component 894 can have two positions, the second adjusted articular component 894 can include a marking adjacent to the second rotational position feature 868 or the third rotational positioning feature 874 so that the surgeon is advised of whether the adjustment is being made in the medial-lateral direction 812 or in the inferior-superior direction 816 by coupling of the second rotational position feature 868 with the first rotational positioning feature 864 or by the coupling of the third rotational positioning feature 874 with the first rotational positioning feature 864. The rotational positioning features 864, 868, 874 described in connection with FIG. 36 can comprise any suitable type of rotational orientation device, e.g., a lock-and-key mechanism, a projection-recess mechanism, etc.

In some embodiments, a third adjusted articular component can be shaped to provide a first incremental offset of a center of rotation of the articular surface relative to the center of rotation 840 of the neutral configuration in a medial-lateral direction 812 and a second incremental offset of the center of rotation relative to the center of rotation 840 of the neutral configuration in an inferior-superior direction 816 when the engagement portion is coupled with the mounting surface 836 of the humeral anchor 804. For example, in some embodiments, the articular surface can be shaped to provide a center of rotation 845 or 845' (see FIG. 35) that provides rotational offset in both the medial-lateral direction 812 and the inferior-superior direction 816. For example, the thickness and/or curved profile of the articular surface can be designed to provide both lateral and superior offsets, as shown in FIG. 35. In one embodiment, the thickness of the articular component 808 can be increased in a direction corresponding to the axis 838 and the position of the articular surface 850 can be shifted as illustrated in the articular surface 850' to provide a greater increment in the medial-lateral direction 812 than in the inferior-superior direction 816. In one embodiment, the thickness of the articular component 808 can be increased in a direction corresponding to the axis 838 and the position of the articular surface 850 can be shifted as illustrated in the articular surface 850" to provide a greater increment in the inferior-superior direction 816 than in the medial-lateral direction 812.

Figure 37:
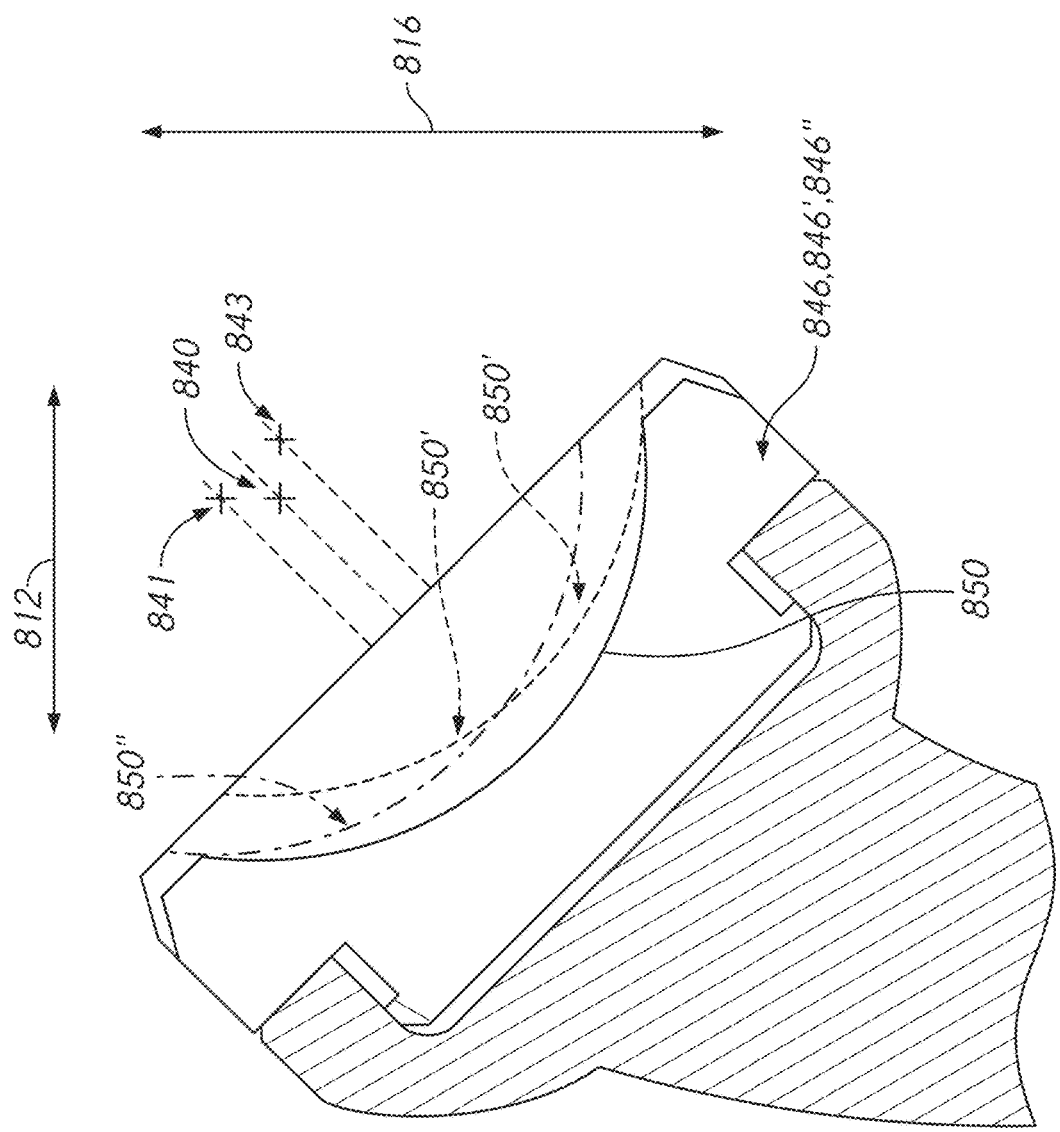
FIG. 37 shows a cross-section of a humeral positioning system that enables positioning a center of rotation of an articular surface at a neutral position, at a medial-lateral adjusted position, or at an inferior-superior adjusted position.

FIG. 37 provides a cross-section schematic in which three articular surfaces 850, 850', 850" and the corresponding centers of rotation are illustrated. FIG. 37 is schematic only and is intended to show the articular surfaces and their corresponding centers of rotation. The humeral positioning system 800 and the kit 890 enable any of these three surfaces 850, 850', 850" and centers of rotation to be provided based on selection and, in some cases orientation, of the appropriate articular component 808. For example, as explained above, the articular surface 850 can be disposed such that the center of rotation 840 is along the axis 838. The articular surface 850' can be disposed and shaped such that the first lateral center of rotation 843 is laterally offset relative to the center of rotation 840. Similarly, the articular surface 850" can be disposed and shaped such that the first superior center of rotation 841 is offset along the superior direction relative to the center of rotation 840.

FIG. 36 also illustrates a method of selecting and implanting a humeral positioning system 800 in a patient. The method can commence with an assessment of soft tissue of the patient to determine what degrees of off-set should be provided post-operatively in the patient. The surgeon can access a shoulder joint of a patient in any suitable manner and can remove a humeral head from a distal humerus H. The surgeon can secure the humeral anchor 840 to the distal humerus H. For example, in some embodiments, the surgeon can bore out or compress a portion of the humerus H, and can insert a stem of the anchor 840 into the opening. In some embodiments, the surgeon can assess a position of the scapula and/or the humerus 12 to determine a desired position of an articular surface 850 (or 850' or 850") of the humeral positioning system 800.

The surgeon can select an articular component 808 from a plurality of pre-made humeral components including at least one humeral components capable of independently adjusting medial-lateral and inferior-superior offsets, as explained above in connection with FIG. 35, for example. The selected articular component 808 can provide the desired position of the articular surface 850 (or 850' or 850") when the articular component 808 is coupled with the humeral anchor 840 and is in contact with an articular component 808 coupled with the scapula.

The surgeon can then bring the selected articular component to the humeral anchor 804 as indicated by the arrow 895. In some embodiments, as explained in connection with, for example, FIG. 36, surgeon can align the first rotational position feature 864 of the humeral anchor 840 with the second rotational position feature 874 of the articular component, e.g., by rotating the component about the axis 897. The surgeon can secure the engagement portion 846 of the articular component 808 (or articular component 894 or articular component 898) to the mounting portion of the humeral anchor 840 with the first rotation position feature 864 aligned with the second rotational position feature 874.

In some embodiments, assessing the position of the scapula relative to the humerus can be performed pre-operatively on the basis of imaging of the patient.

After the articular component is aligned, e.g., rotationally aligned, with the humeral anchor 804 the humeral positioning system 800 can be fully assembled to provide the desired soft tissue tensioning.

Terminology

Although certain embodiments have been described herein, the implants and methods described herein can interchangeably use any articular component, as the context may dictate.

As used herein, the relative terms "proximal" and "distal" shall be defined from the perspective of the humerus. Thus, proximal refers to the direction of the end of the humerus adjacent to the scapula and forming part of the shoulder joint, which may be referred to herein as the superior direction, end or portion, and distal refers to the direction away from proximal, which can be the end of the humerus forming part of the elbow joint and which may be referred to herein as the inferior direction, end or portion of the humerus.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a humeral stem into a humerus" include "instructing insertion of a humeral head into a humerus."

What is claimed is:

1. A method, comprising:
   accessing a shoulder joint of a patient and removing a humeral head from a distal humerus so that cancellous bone of the distal humerus is exposed;
   securing a humeral anchor into the cancellous bone of the distal humerus, wherein the humeral anchor comprises a stem having a curvature along its length from an inferior end to a superior end, the length and the curvature of the stem configured for a specific patient, the stem including an enlarged mounting portion disposed at the superior end of the stem, the enlarged mounting portion having a mounting surface defining a mounting hole, a mounting channel surrounding the mounting hole between an outer wall and an inner wall, and an axis that extends perpendicular to the mounting surface, wherein the humeral anchor has a first rotational position feature and a third rotational position feature that are positioned 180 rotational degrees apart from one another about the axis,
   wherein the stem comprises bone integration features for enhancing bone integration within the cancellous bone, wherein the axis intersects a center of rotation of a neutral configuration for an articular surface of a humeral component that is configured to be coupled with the mounting surface;
   assessing a position of the scapula and/or the numerus to determine a desired position of an articular surface of a humeral positioning system;
   selecting one humeral component from a plurality of pre-made humeral components, wherein the plurality of pre-made humeral components includes:
      at least one humeral component comprising:
         an engagement portion configured to connect to the mounting surface of the humeral anchor, and
         an articular surface opposite the engagement portion, wherein the articular surface has a center of rotation at the center of rotation for the neutral configuration when the engagement portion is coupled with the mounting surface of the humeral anchor; and
      at least another humeral component that comprises:
         an engagement portion configured to connect to the mounting surface of the humeral anchor, and
         an articular surface opposite the engagement portion, wherein the articular surface has a center of rotation that is offset relative to the center of rotation of the neutral configuration in at least one of a medial-lateral direction and an inferior-superior direction when the engagement portion is coupled with the mountig surface of the humeral anchor,
      wherein the selected humeral component has a second rotational position feature;
   coupling the selected humeral component to the mounting surface of the humeral anchor, such that the selected humeral component provides the desired offset relative to the center of rotation of the neutral configuration in a desired one of the medial-lateral direction or the inferior-superior direction when the humeral component is in contact with an articular component coupled with the scapula;

aligning the second rotational position feature of the selected humeral component with the first rotational position feature or the third rotational position feature of the humeral anchor; and securing the engagement portion of the humeral component to the mounting portion of the humeral anchor with the rotational position features aligned.

2. The method of claim 1, wherein assessing the position of the scapula relative to the humerus is performed pre-operatively on the basis of imaging of the patient.

3. The method of claim 1, wherein the humeral anchor and the humeral component are configured for a specific patient based on pre-operative imaging with respect to one or more of inclination angle, center of rotation offset, version angle, tensioning dimension, lead angle, metaphysis transverse size, articular surface offset, inlay depth, jump distance, jump distance asymmetry, or humeral anchor shape.

4. The method of claim 1, wherein the humeral anchor comprises a locking mechanism including a plurality of flexible flanges disposed within the mounting channel on an inner surface of the outer wall.

5. The method of claim 1, wherein the bone integration features comprise a plurality of apertures.

6. The method of claim 5, wherein each of the apertures of the plurality of apertures includes an interior portion, a superior portion, and a space disposed therethrough between the inferior portion and the superior portion.

7. The method of claim 5, wherein the stem has a curved longitudinal axis and the apertures of the plurality of apertures are aligned with the longitudinal axis of the stem.

8. The method of claim 5, wherein the stem includes a hollow shaft portion and the apertures of the plurality of apertures can each be angled relative to a curved longitudinal axis of the hollow shaft portion.

* * * * *